United States Patent
Pavletich et al.

(10) Patent No.: US 6,824,971 B1
(45) Date of Patent: Nov. 30, 2004

(54) METHODS OF INHIBITING OR ENHANCING THE TGFβ-SMAD SIGNALING PATHWAY

(75) Inventors: Nikola Pavletich, New York, NY (US); Yigong Shi, New York, NY (US); Joan Massagué, New York, NY (US)

(73) Assignee: Sloan-Kettering Institute for Cancer Research, New York, NY (US)

(*) Notice: Subject to any disclaimer, the term of this patent is extended or adjusted under 35 U.S.C. 154(b) by 0 days.

(21) Appl. No.: 09/107,779

(22) Filed: Jun. 30, 1998

Related U.S. Application Data

(60) Provisional application No. 60/065,113, filed on Nov. 12, 1997, now abandoned, and provisional application No. 60/052,774, filed on Jul. 1, 1997, now abandoned.

(51) Int. Cl.[7] .............................................. C12Q 1/00
(52) U.S. Cl. ....................................................... 435/4
(58) Field of Search ............................................ 435/4

(56) References Cited

PUBLICATIONS

Liu et al, Genes Dev., 1997, 11:3157–3167.*
Massague et al (TICB, 7:187–191), 1997.*
Gura (Science, 278:1041–1042), 1997.*
Jain (Sci. Am., 271:58–65), 1994.*
Curti (Crit. Rev. in Oncology/Hematology, 14:29–39), 1993.*
Bowie et al (Science, 257:1306–1310), 1990.*
Burgess et al (J. Cell. Biol., 111: 2129–2138), 1990.*
Lazar et al (Mol and Cell Biol., 8:1247–1252), 1988.*

* cited by examiner

*Primary Examiner*—Susan Ungar
(74) *Attorney, Agent, or Firm*—Benjamin Aaron Adler

(57) ABSTRACT

Signal transduction by the TGF-β family involves sets of receptor serine/threonine kinases, Smad proteins that act as receptor substrates, and Smad-associated transcription factors that target specific genes. Discrete structural elements were identified that dictate the selective interactions between receptors and Smads and between Smads and transcription factors in the TGF-β and BMP pathways. A cluster of four residues in the L45 loop of the type I receptor kinase domain, and a matching set of two residues in the L3 loop of the Smad C-terminal domain establish the specificity of receptor-Smad interactions. A cluster of residues in the highly exposed α-helix 2 of the Smad C-terminal domain specify the interaction with the DNA-binding factor Fast1 and, as a result, the gene responses mediated by the pathway. By establishing specific interactions, these determinants keep the TGF-β and BMP pathways segregated from each other.

1 Claim, 44 Drawing Sheets

(10 of 44 Drawing Sheet(s) Filed in Color)

Fig. 21A

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 234 amino acids
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: no (iv) ANTI-SENSE: no (v) FRAGMENT TYPE: internal (vi) ORIGINAL SOURCE:

(vii) IMMEDIATE SOURCE:

(viii) POSITION IN GENOME:

-continued (ix) FEATURE:

(x) PUBLICATION INFORMATION:

(xi) SEQUENCE DESCRIPTION:SEQ ID NO: 1:

Ala Pro Glu Tyr Trp Cys Ser Ile Ala Tyr Phe Glu Met Asp Val
                 5                  10                  15

Gln Val Gly Glu Thr Phe Lys Val Pro Ser Ser Cys Pro Ile Val
             20                  25                  30

Thr Val Asp Gly Tyr Val Asp Pro Ser Gly Gly Asp Arg Phe Cys
             35                  40                  45

Leu Gly Gln Leu Ser Asn Val His Arg Thr Glu Ala Ile Glu Arg
             50                  55                  60

Ala Arg Leu His Ile Gly Lys Gly Val Gln Leu Glu Cys Lys Gly
             65                  70                  75

Glu Gly Asp Val Trp Val Arg Cys Leu Ser Asp His Ala Val Phe
             80                  85                  90

Val Gln Ser Tyr Tyr Leu Asp Arg Glu Ala Gly Arg Ala Pro Gly
             95                 100                 105

Asp Ala Val His Lys Ile Tyr Pro Ser Ala Tyr Ile Lys Val Phe
            110                 115                 120

Asp Leu Arg Gln Cys His Arg Gln Met Gln Gln Gln Ala Ala Thr
            125                 130                 135

Ala Gln Ala Ala Ala Ala Gln Ala Ala Val Ala Gly Asn
            140                 145                 150

Ile Pro Gly Pro Gly Ser Val Gly Gly Ile Ala Pro Ala Ile Ser
            155                 160                 165

Leu Ser Ala Ala Gly Ile Gly Val Asp Asp Leu Arg Arg Leu
            170                 175                 180

Cys Ile Leu Arg Met Ser Phe Val Lys Gly Trp Gly Pro Asp Tyr
            185                 190                 195

Pro Arg Gln Ser Ile Lys Glu Thr Pro Cys Trp Ile Glu Ile His
            200                 205                 210

Leu His Arg Ala Leu Gln Leu Leu Asp Glu Val Leu His Thr Met
            215                 220                 225

Pro Ile Ala Asp Pro Gln Pro Leu Asp
            230

(2) INFORMATION FOR SEQ ID NO:2:

(i) SEQUENCE CHARACTERISTICS:
        (A) LENGTH: 197 amino acids
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: no (iv) ANTI-SENSE: no (v) FRAGMENT TYPE: internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   2:

Lys His Trp Cys Ser Ile Val Tyr Tyr Glu Leu Asn Asn Arg Val
                 5                  10                  15

Gly Glu Ala Phe His Ala Ser Ser Thr Ser Val Leu Val Asp Gly
                20                  25                  30

Phe Thr Asp Pro Ser Asn Asn Lys Asn Arg Phe Cys Leu Gly Leu
                35                  40                  45

Leu Ser Asn Val Asn Arg Asn Ser Thr Ile Glu Asn Thr Arg Arg
                50                  55                  60

His Ile Gly Lys Gly Val His Leu Tyr Tyr Val Gly Gly Glu Val
                65                  70                  75

Tyr Ala Glu Cys Leu Ser Asp Ser Ser Ile Phe Val Gln Ser Arg
                80                  85                  90

Asn Cys Asn Tyr His His Gly Phe His Pro Thr Thr Val Cys Lys
                95                 100                 105

Ile Pro Ser Gly Cys Ser Leu Lys Ile Phe Asn Asn Gln Glu Phe
               110                 115                 120

Ala Gln Leu Leu Ala Gln Ser Val Asn His Gly Phe Glu Thr Val
               125                 130                 135

Tyr Glu Leu Thr Lys Met Cys Thr Ile Arg Met Ser Phe Val Lys
               140                 145                 150

Gly Trp Gly Ala Glu Tyr His Arg Gln Asp Val Thr Ser Thr Pro
               155                 160                 165

Cys Trp Ile Glu Ile His Leu His Gly Pro Leu Gln Trp Leu Asp
               170                 175                 180

Lys Val Leu Thr Gln Met Gly Ser Pro His Asn Pro Ile Ser Ser
               185                 190                 195

Val Ser (2) INFORMATION FOR SEQ ID NO:3:

(i) SEQUENCE CHARACTERISTICS:
        (A) LENGTH:   196 amino acids
        (B) TYPE:  amino acid
        (C) STRANDEDNESS:
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   3:

Ala Phe Trp Cys Ser Ile Ala Tyr Tyr Glu Leu Asn Gln Arg Val
                 5                  10                  15

-continued

```
Gly Glu Thr Phe His Ala Ser Gln Pro Ser Leu Thr Val Asp Gly
             20                  25                  30

Phe Thr Asp Pro Ser Asn Ser Glu Arg Phe Cys Leu Gly Leu Leu
             35                  40                  45

Ser Asn Val Asn Arg Asn Ala Thr Val Glu Met Thr Arg Arg His
             50                  55                  60

Ile Gly Arg Gly Val Arg Leu Tyr Tyr Ile Gly Gly Glu Val Phe
             65                  70                  75

Ala Glu Cys Leu Ser Asp Ser Ala Ile Phe Val Gln Ser Pro Asn
             80                  85                  90

Cys Asn Gln Arg Tyr Gly Trp His Pro Ala Thr Val Cys Lys Ile
             95                 100                 105

Pro Pro Gly Cys Asn Leu Lys Ile Phe Asn Asn Gln Glu Phe Ala
            110                 115                 120

Ala Leu Leu Ala Gln Ser Val Asn Gln Gly Phe Glu Ala Val Tyr
            125                 130                 135

Gln Leu Thr Arg Met Cys Thr Ile Arg Met Ser Phe Val Lys Gly
            140                 145                 150

Trp Gly Ala Glu Tyr Arg Arg Gln Thr Val Thr Ser Thr Pro Cys
            155                 160                 165

Trp Ile Glu Leu His Leu His Gly Pro Leu Gln Trp Leu Asp Lys
            170                 175                 180

Val Leu Thr Gln Met Gly Ser Pro Ser Val Arg Cys Ser Ser Met
            185                 190                 195

Ser
```

(2) INFORMATION FOR SEQ ID NO:4:

(i) SEQUENCE CHARACTERISTICS:
        (A) LENGTH: 196 amino acids
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: no (iv) ANTI-SENSE: no (v) FRAGMENT TYPE: internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 4:

```
Ala Phe Trp Cys Ser Ile Ser Tyr Tyr Glu Leu Asn Gln Arg Val
              5                  10                  15

Gly Glu Thr Phe His Ala Ser Gln Pro Ser Met Thr Val Asp Gly
             20                  25                  30

Phe Thr Asp Pro Ser Asn Ser Glu Arg Phe Cys Leu Gly Leu Leu
             35                  40                  45

Ser Asn Val Asn Arg Asn Ala Ala Val Glu Leu Thr Arg Arg His
             50                  55                  60
```

-continued

```
Ile Gly Arg Gly Val Arg Leu Tyr Tyr Ile Gly Gly Glu Val Phe
                65                  70                  75

Ala Glu Cys Leu Ser Asp Ser Ala Ile Phe Val Gln Ser Pro Asn
                80                  85                  90

Cys Asn Gln Arg Tyr Gly Trp His Pro Ala Thr Val Cys Lys Ile
                95                 100                 105

Pro Pro Gly Cys Asn Leu Lys Ile Phe Asn Asn Gln Glu Phe Ala
               110                 115                 120

Ala Leu Leu Ala Gln Ser Val Asn Gln Gly Phe Glu Ala Val Tyr
               125                 130                 135

Gln Leu Thr Arg Met Cys Thr Ile Arg Met Ser Phe Val Lys Gly
               140                 145                 150

Trp Gly Ala Glu Tyr Arg Arg Gln Thr Val Thr Ser Thr Pro Cys
               155                 160                 165

Trp Ile Glu Leu His Leu His Gly Pro Leu Gln Trp Leu Asp Lys
               170                 175                 180

Val Leu Thr Gln Met Gly Ser Pro Ser Ile Arg Cys Ser Ser Val
               185                 190                 195

Ser (2) INFORMATION FOR SEQ ID NO:5:

(i) SEQUENCE CHARACTERISTICS:
        (A) LENGTH:  198 amino acids
        (B) TYPE:  amino acid
        (C) STRANDEDNESS:
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   5:

Pro Lys His Trp Cys Ser Ile Val Tyr Tyr Glu Leu Asn Asn Arg
                 5                  10                  15

Val Gly Glu Ala Phe His Ala Ser Ser Thr Ser Val Leu Val Asp
                20                  25                  30

Gly Phe Thr Asp Pro Ser Asn Asn Lys Ser Arg Phe Cys Leu Gly
                35                  40                  45

Leu Leu Ser Asn Val Asn Arg Asn Ser Thr Ile Glu Asn Thr Arg
                50                  55                  60

Arg His Ile Gly Lys Gly Val His Leu Tyr Tyr Val Gly Gly Glu
                65                  70                  75

Val Tyr Ala Glu Cys Leu Ser Asp Ser Ser Ile Phe Val Gln Ser
                80                  85                  90

Arg Asn Cys Asn Phe His His Gly Phe Gln Ser Thr Ser Val Cys
```

```
                      95                  100                 105
Lys Ile Pro Ser Ser Cys Ser Leu Lys Ile Phe Asn Asn Gln Glu
                 110                 115                 120
Phe Ala Gln Leu Leu Ala Gln Ser Val Asn His Gly Phe Glu Ala
                 125                 130                 135
Val Tyr Glu Leu Thr Lys Met Cys Thr Ile Arg Met Ser Phe Val
                 140                 145                 150
Lys Gly Trp Gly Ala Glu Tyr His Arg Gln Asp Val Thr Ser Thr
                 155                 160                 165
Pro Cys Trp Ile Glu Ile His Leu His Gly Pro Leu Gln Trp Leu
                 170                 175                 180
Asp Lys Val Leu Thr Gln Met Gly Ser Pro Leu Asn Pro Ile Ser
                 185                 190                 195
Ser Val Ser (2) INFORMATION FOR SEQ ID NO:6:

(i) SEQUENCE CHARACTERISTICS:
        (A) LENGTH:  197 amino acids
        (B) TYPE:  amino acid
        (C) STRANDEDNESS:
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   6:

Ala Phe Trp Ala Ser Ile Ala Tyr Tyr Glu Leu Asn Cys Arg Val
                   5                  10                  15
Gly Glu Val Phe His Cys Asn Asn Ser Val Leu Val Asp Gly
                  20                  25                  30
Phe Thr Asn Pro Ser Asn Ser Asp Arg Cys Cys Leu Gly Gln
                  35                  40                  45
Leu Ser Asn Val Asn Arg Asn Ser Thr Ile Glu Asn Thr Arg Arg
                  50                  55                  60
His Ile Gly Lys Gly Val His Leu Tyr Tyr Val Thr Gly Glu Val
                  65                  70                  75
Tyr Ala Glu Cys Leu Ser Asp Ser Ala Ile Phe Val Gln Ser Arg
                  80                  85                  90
Asn Cys Asn Tyr His His Gly Phe His Pro Ser Thr Val Cys Lys
                  95                 100                 105
Ile Pro Pro Gly Cys Ser Leu Lys Ile Phe Asn Asn Gln Glu Phe
                 110                 115                 120
Ala Gln Leu Leu Ser Gln Ser Val Asn Asn Gly Phe Glu Ala Val
                 125                 130                 135
```

-continued

```
Tyr Glu Leu Thr Lys Met Cys Thr Ile Arg Met Ser Phe Val Lys
            140                 145                 150

Gly Trp Gly Ala Glu Tyr His Arg Gln Asp Val Thr Ser Thr Pro
            155                 160                 165

Cys Trp Ile Glu Ile His Leu His Gly Pro Leu Gln Trp Leu Asp
            170                 175                 180

Lys Val Leu Thr Gln Met Gly Ser Pro His Asn Ala Ile Ser Ser
            185                 190                 195

Val Ser (2) INFORMATION FOR SEQ ID NO:7:

(i) SEQUENCE CHARACTERISTICS:
        (A) LENGTH:  199 amino acids
        (B) TYPE:  amino acid
        (C) STRANDEDNESS:
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   7:

Gln Phe Trp Ala Thr Val Ser Tyr Tyr Glu Leu Asn Thr Arg Val
              5                  10                  15

Gly Glu Gln Val Lys Val Ser Ser Thr Thr Ile Thr Ile Asp Gly
             20                  25                  30

Phe Thr Asp Pro Cys Ile Asn Gly Ser Lys Ile Ser Leu Gly Leu
             35                  40                  45

Phe Ser Asn Val Asn Arg Asn Ala Thr Ile Glu Asn Thr Arg Arg
             50                  55                  60

His Ile Gly Asn Gly Val Lys Leu Thr Tyr Val Arg Ser Asn Gly
             65                  70                  75

Ser Leu Phe Ala Gln Cys Glu Ser Asp Ser Ala Ile Phe Val Gln
             80                  85                  90

Ser Ser Asn Cys Asn Tyr Ile Asn Gly Phe His Ser Thr Thr Val
             95                 100                 105

Val Lys Ile Ala Asn Lys Cys Ser Leu Lys Ile Phe Asp Met Glu
            110                 115                 120

Ile Phe Arg Gln Leu Leu Glu Asp Cys Ser Arg Arg Gly Phe Asp
            125                 130                 135

Ala Ser Phe Asp Leu Gln Lys Met Thr Phe Ile Arg Met Ser Phe
            140                 145                 150

Val Lys Gly Trp Gly Ala Glu Tyr Gln Arg Gln Asp Val Thr Ser
            155                 160                 165

Thr Pro Cys Trp Ile Glu Ile His Leu His Ala Pro Leu Ala Trp
            170                 175                 180
```

-continued

```
Leu Asp Arg Val Leu Ser Thr Met Gly Pro Thr Pro Arg Pro Ile
            185                 190                 195

Ser Ser Ile Ser
```

(2) INFORMATION FOR SEQ ID NO:8:

(i) SEQUENCE CHARACTERISTICS:
        (A) LENGTH: 198 amino acids
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: no (iv) ANTI-SENSE: no (v) FRAGMENT TYPE: internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 8:

```
Lys Ser Trp Ala Gln Ile Thr Tyr Phe Glu Leu Asn Ser Arg Val
                 5                  10                  15

Gly Glu Val Phe Lys Leu Val Asn Leu Ser Ile Thr Val Asp Gly
                20                  25                  30

Tyr Thr Asn Pro Ser Asn Ser Asn Thr Arg Ile Cys Leu Gly Gln
                35                  40                  45

Leu Thr Asn Val Asn Arg Asn Gly Thr Ile Glu Asn Thr Arg Met
                50                  55                  60

His Ile Gly Lys Gly Ile Gln Leu Asp Asn Lys Glu Asp Gln Met
                65                  70                  75

His Ile Met Ile Thr Asn Asn Ser Asp Met Pro Val Phe Val Gln
                80                  85                  90

Ser Lys Asn Thr Asn Leu Met Met Asn Met Pro Leu Val Lys Val
                95                  100                 105

Cys Arg Ile Pro Pro His Ser Gln Leu Cys Val Phe Glu Phe Asn
                110                 115                 120

Leu Phe Phe Gln Met Leu Glu Gln Ser Cys Asn Asp Ser Asp Gly
                125                 130                 135

Leu Asn Glu Leu Ser Lys His Cys Phe Ile Arg Ile Ser Phe Val
                140                 145                 150

Lys Gly Trp Gly Glu Asp Tyr Pro Arg Gln Asp Val Thr Ser Thr
                155                 160                 165

Pro Cys Trp Leu Glu Leu Arg Leu Asn Val Pro Leu Ala Tyr Ile
                170                 175                 180

Asp Gln Lys Met Lys Gln Thr Pro Arg Thr Asn Leu Met Pro Asn
                185                 190                 195

Ser Met Thr
```

(2) INFORMATION FOR SEQ ID NO:9:

```
    (i) SEQUENCE CHARACTERISTICS:
        (A) LENGTH:  224 amino acids
        (B) TYPE:  amino acid
        (C) STRANDEDNESS:
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   9:
```

```
Leu Asp Asn Trp Cys Ser Ile Ile Tyr Tyr Glu Leu Asp Thr Pro
                 5                  10                  15

Ile Gly Glu Thr Phe Lys Val Ser Ala Arg Asp His Gly Lys Val
             20                  25                  30

Ile Val Asp Gly Gly Met Asp Pro His Gly Glu Asn Glu Gly Arg
             35                  40                  45

Leu Cys Leu Gly Ala Leu Ser Asn Val His Arg Thr Glu Ala Ser
             50                  55                  60

Glu Lys Ala Arg Ile His Ile Gly Arg Gly Val Glu Leu Thr Ala
             65                  70                  75

His Ala Asp Gly Asn Ile Ser Ile Thr Ser Asn Cys Lys Ile Phe
             80                  85                  90

Val Arg Ser Gly Tyr Leu Asp Tyr Thr His Gly Ser Glu Tyr Ser
             95                 100                 105

Ser Lys Ala His Arg Phe Thr Pro Asn Glu Ser Ser Phe Thr Val
            110                 115                 120

Phe Asp Ile Arg Trp Ala Tyr Met Gln Met Leu Arg Arg Ser Arg
            125                 130                 135

Asp Ser Asn Glu Ala Val Arg Ala Gln Ala Ala Ala Val Ala Gly
            140                 145                 150

Tyr Ala Pro Met Ser Val Met Pro Ala Ile Met Pro Ser Ser Gly
            155                 160                 165

Val Asp Arg Met Arg Arg Asp Phe Cys Thr Ile Ala Ile Ser Phe
            170                 175                 180

Val Lys Ala Trp Gly Asp Val Tyr Gln Arg Lys Thr Ile Lys Glu
            185                 190                 195

Thr Pro Cys Trp Ile Glu Val Thr Leu His Arg Pro Leu Gln Ile
            200                 205                 210

Leu Asp Gln Leu Leu Lys Asn Ser Ser Gln Phe Gly Ser Ser
            215                 220
```

```
(2) INFORMATION FOR SEQ ID NO:10:

(i) SEQUENCE CHARACTERISTICS:
        (A) LENGTH:  50 amino acids
        (B) TYPE:  amino acid
```

```
            (C) STRANDEDNESS:
            (D) TOPOLOGY:  linear (ii) MOLECULE TYPE:
            (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:  10:

Phe Val Lys Gly Trp Gly Ala Glu Tyr Arg Arg Gln Thr Val Thr
                 5                  10                  15

Ser Thr Pro Cys Trp Ile Glu Leu His Leu His Gly Pro Leu Gln
                20                  25                  30

Trp Leu Asp Lys Val Leu Thr Gln Met Gly Ser Pro Ser Val Arg
                35                  40                  45

Cys Ser Ser Met Ser
                50

(2) INFORMATION FOR SEQ ID NO:11:

(i) SEQUENCE CHARACTERISTICS:
            (A) LENGTH:  50 amino acids
            (B) TYPE:  amino acid
            (C) STRANDEDNESS:
            (D) TOPOLOGY:  linear (ii) MOLECULE TYPE:
            (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:  11:

Phe Val Lys Gly Trp Gly Ala Glu Tyr Arg Arg Gln Thr Val Thr
                 5                  10                  15

Ser Thr Pro Cys Trp Ile Glu Leu His Leu His Gly Pro Leu Gln
                20                  25                  30

Trp Leu Asp Lys Val Leu Thr Gln Met Gly Ser Pro Ser Ile Arg
                35                  40                  45

Cys Ser Ser Met Ser
                50
```

(2) INFORMATION FOR SEQ ID NO:12:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: no (iv) ANTI-SENSE: no (v) FRAGMENT TYPE: internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 12:

Phe Val Lys Gly Trp Gly Ala Glu Tyr His Arg Gln Asp Val Thr
         5                    10                  15

Ser Thr Pro Cys Trp Ile Glu Leu His Leu His Gly Pro Leu Gln
        20                  25               30

Trp Leu Asp Lys Val Leu Thr Gln Met Gly Ser Pro His Asn Ala
        35                  40               45

Ile Ser Ser Met Ser
        50

(2) INFORMATION FOR SEQ ID NO:13:

(i) SEQUENCE CHARACTERISTICS:
        (A) LENGTH: 50 amino acids
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: no (iv) ANTI-SENSE: no (v) FRAGMENT TYPE: internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 13:

Phe Val Lys Gly Trp Gly Ala Glu Tyr His Arg Gln Asp Val Thr
         5                    10                  15

Ser Thr Pro Cys Trp Ile Glu Leu His Leu His Gly Pro Leu Gln
        20                  25               30

Trp Leu Asp Lys Val Leu Thr Gln Met Gly Ser Pro His Asn Pro
        35                  40               45

```
Ile Ser Ser Met Ser
            50

(2) INFORMATION FOR SEQ ID NO:14:

(i) SEQUENCE CHARACTERISTICS:
        (A) LENGTH:  50 amino acids
        (B) TYPE:  amino acid
        (C) STRANDEDNESS:
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   14:

Phe Val Lys Gly Trp Gly Ala Glu Tyr His Arg Gln Asp Val Thr
              5                  10                  15

Ser Thr Pro Cys Trp Ile Glu Leu His Leu His Gly Pro Leu Gln
             20                  25                  30

Trp Leu Asp Lys Val Leu Thr Gln Met Gly Ser Pro Leu Asn Pro
             35                  40                  45

Ile Ser Ser Met Ser
            50

(2) INFORMATION FOR SEQ ID NO:15:

(i) SEQUENCE CHARACTERISTICS:
        (A) LENGTH:  48 amino acids
        (B) TYPE:  amino acid
        (C) STRANDEDNESS:
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   15:

Phe Val Lys Gly Trp Gly Pro Asp Tyr Pro Arg Gln Ser Ile Lys
              5                  10                  15
```

```
Glu Thr Pro Cys Trp Ile Glu Leu His Leu His Arg Ala Leu Gln
                20                  25                  30

Leu Leu Asp Glu Val Leu His Thr Met Pro Ile Ala Asp Pro Gln
            35                  40                  45

Pro Leu Asp
```

(2) INFORMATION FOR SEQ ID NO:16:

(i) SEQUENCE CHARACTERISTICS:
        (A) LENGTH: 29 amino acids
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: no (iv) ANTI-SENSE: no (v) FRAGMENT TYPE: internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 16:

```
Phe Ala Lys Gly Trp Gly Pro Cys Tyr Ser Arg Gln Phe Ile Thr
                 5                  10                  15

Ser Cys Pro Cys Trp Leu Glu Ile Leu Leu Asn Asn Pro Arg
                20                  25
```

(2) INFORMATION FOR SEQ ID NO:17:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: no (iv) ANTI-SENSE: no (v) FRAGMENT TYPE: internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 17:

```
Phe Val Lys Gly Trp Gly Gln Cys Tyr Thr Arg Gln Phe Ile Ser
                 5                  10                  15

Ser Cys Pro Cys Trp Leu Glu Val Ile Phe Asn Ser Arg
                20                  25
```

```
(2) INFORMATION FOR SEQ ID NO:18:

(i) SEQUENCE CHARACTERISTICS:
        (A) LENGTH:  25 amino acids
        (B) TYPE:  amino acid
        (C) STRANDEDNESS:
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   18:

Leu Gly Phe Ile Ala Ala Asp Asn Lys Asp Asn Gly Thr Trp Thr
                  5                  10                  15

Gln Leu Trp Leu Val Ser Asp Tyr His Glu
                 20                  25

(2) INFORMATION FOR SEQ ID NO:19:

(i) SEQUENCE CHARACTERISTICS:
        (A) LENGTH: 25 amino acids
        (B) TYPE:  amino acid
        (C) STRANDEDNESS:
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   19:

Leu Gly Phe Ile Ala Ala Asp Ile Lys Gly Thr Gly Thr Trp Thr
                  5                  10                  15

Gln Leu Tyr Leu Ile Thr Asp Tyr His Glu
                 20                  25

(2) INFORMATION FOR SEQ ID NO:20:

(i) SEQUENCE CHARACTERISTICS:
        (A) LENGTH: 25 amino acids
        (B) TYPE:  amino acid
```

```
            (C) STRANDEDNESS:
            (D) TOPOLOGY:  linear (ii) MOLECULE TYPE:
            (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   20:

Leu Gly Phe Ile Ala Ala Asp Ile Lys Gly Asn Gly Thr Trp Thr
                 5                  10                  15

Gln Met Leu Leu Ile Thr Asp Tyr His Glu
             20                  25

(2) INFORMATION FOR SEQ ID NO:21:

(i) SEQUENCE CHARACTERISTICS:
            (A) LENGTH: 25 amino acids
            (B) TYPE:  amino acid
            (C) STRANDEDNESS:
            (D) TOPOLOGY:  linear (ii) MOLECULE TYPE:
            (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   21:

Leu Gly Phe Ile Ala Ser Asp Met Thr Ser Arg Asn Ser Ser Thr
                 5                  10                  15

Gln Leu Trp Leu Ile Thr His Tyr His Glu
             20                  25

(2) INFORMATION FOR SEQ ID NO:22:

(i) SEQUENCE CHARACTERISTICS:
            (A) LENGTH:  25 amino acids
            (B) TYPE:  amino acid
            (C) STRANDEDNESS:
            (D) TOPOLOGY:  linear (ii) MOLECULE TYPE:
            (A) DESCRIPTION:  peptide (iii) HYPOTHETICAL:  no
```

(iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   22:

Leu Gly Phe Ile Ala Ser Asp Met Thr Ser Arg His Ser Ser Thr
                 5                  10                  15

Gln Leu Trp Leu Ile Thr His Tyr His Glu
                20                  25

(2) INFORMATION FOR SEQ ID NO:23:

(i) SEQUENCE CHARACTERISTICS:
             (A) LENGTH:  25 amino acids
             (B) TYPE:  amino acid
             (C) STRANDEDNESS:
             (D) TOPOLOGY:  linear (ii) MOLECULE TYPE:
             (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   23:

Leu Gly Phe Ile Gly Ser Asp Met Thr Ser Arg Asn Ser Cys Thr
                 5                  10                  15
Gln Leu Trp Leu Met Thr His Tyr Tyr Pro
                20                  25

(2) INFORMATION FOR SEQ ID NO:24:

(i) SEQUENCE CHARACTERISTICS:
             (A) LENGTH:  199 amino acids
             (B) TYPE:  amino acid
             (C) STRANDEDNESS:
             (D) TOPOLOGY:  linear (ii) MOLECULE TYPE:
             (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   24:

Glu Pro Lys His Trp Cys Ser Ile Val Tyr Tyr Glu Leu Asn Asn
                  5                  10                  15

Arg Val Gly Glu Ala Phe His Ala Ser Ser Thr Ser Val Leu Val
                 20                  25                  30

Asp Gly Phe Thr Asp Pro Ser Asn Asn Lys Asn Arg Phe Cys Leu
                 35                  40                  45

Gly Leu Leu Ser Asn Val Arg Asn Ser Thr Ile Glu Asn Thr
                 50                  55                  60

Arg Arg His Ile Gly Lys Gly Val His Leu Tyr Tyr Val Gly Gly
                 65                  70                  75

Glu Val Tyr Ala Glu Cys Leu Ser Asp Ser Ser Ile Phe Val Gln
                 80                  85                  90

Ser Arg Asn Cys Asn Tyr His His Gly Phe His Pro Thr Thr Val
                 95                 100                 105

Cys Lys Ile Pro Ser Gly Cys Ser Leu Lys Ile Phe Asn Asn Gln
                110                 115                 120

Glu Phe Ala Gln Leu Leu Ala Gln Ser Val Asn His Gly Phe Glu
                125                 130                 135

Thr Val Tyr Glu Leu Thr Lys Met Cys Thr Ile Arg Met Ser Phe
                140                 145                 150

Val Lys Gly Trp Gly Ala Glu Tyr His Arg Gln Asp Val Thr Ser
                155                 160                 165

Thr Pro Cys Trp Ile Glu Ile His Leu His Gly Pro Leu Gln Trp
                170                 175                 180

Leu Asp Lys Val Leu Thr Gln Met Gly Ser Pro His Asn Pro Ile
                185                 190                 195

Ser Ser Val Ser (2) INFORMATION FOR SEQ ID NO:25:

(i) SEQUENCE CHARACTERISTICS:
       (A) LENGTH:  198 amino acids
       (B) TYPE:  amino acid
       (C) STRANDEDNESS:
       (D) TOPOLOGY:  linear (ii) MOLECULE TYPE:
       (A) DESCRIPTION:  peptide (iii) HYPOTHETICAL:  no (iv) ANTI-SENSE:  no (v) FRAGMENT TYPE:  internal (vi) ORIGINAL SOURCE:

(vii) IMMEDIATE SOURCE:

(viii) POSITION IN GENOME:

(ix) FEATURE:

(x) PUBLICATION INFORMATION:

-continued (xi) SEQUENCE DESCRIPTION:SEQ ID NO: 25:

```
Glu Pro Ala Phe Trp Cys Ser Ile Ala Tyr Tyr Glu Leu Asn Gln
                  5                  10                  15

Arg Val Gly Glu Thr Phe His Ala Ser Gln Pro Ser Leu Thr Val
                 20                  25                  30

Asp Gly Phe Thr Asp Pro Ser Asn Ser Glu Arg Phe Cys Leu Gly
                 35                  40                  45

Leu Leu Ser Asn Val Asn Arg Asn Ala Thr Val Glu Met Thr Arg
                 50                  55                  60

Arg His Ile Gly Arg Gly Val Arg Leu Tyr Tyr Ile Gly Gly Glu
                 65                  70                  75

Val Phe Ala Glu Cys Leu Ser Asp Ser Ala Ile Phe Val Gln Ser
                 80                  85                  90

Pro Asn Cys Asn Gln Arg Tyr Gly Trp His Pro Ala Thr Val Cys
                 95                 100                 105

Lys Ile Pro Pro Gly Cys Asn Leu Lys Ile Phe Asn Asn Gln Glu
                110                 115                 120

Phe Ala Ala Leu Leu Ala Gln Ser Val Asn Gln Gly Phe Glu Ala
                125                 130                 135

Val Tyr Gln Leu Thr Arg Met Cys Thr Ile Arg Met Ser Phe Val
                140                 145                 150

Lys Gly Trp Gly Ala Glu Tyr Arg Arg Gln Thr Val Thr Ser Thr
                155                 160                 165

Pro Cys Trp Ile Glu Leu His Leu His Gly Pro Leu Gln Trp Leu
                170                 175                 180

Asp Lys Val Leu Thr Gln Met Gly Ser Pro Ser Val Arg Cys Ser
                185                 190                 195

Ser Met Ser
```

METHODS OF INHIBITING OR ENHANCING THE TGFβ-SMAD SIGNALING PATHWAY

CROSS-REFERENCED TO RELATED APPLICATIONS

This non-provisional application claims the benefit of priority of provisional applications U.S. Ser. Nos. 60/052,774 filed on Jul. 1, 1997, now abandoned, and 60/065,113 filed on Nov. 12, 1997, now abandoned.

FEDERAL FUNDING LEGEND

This invention was created in part using funds from the National Institutes of Health under grant R37-CA34610. The federal government, therefore, has certain rights in this invention.

BACKGROUND OF THE INVENTION

1. Field of the Invention

The present invention relates generally to the fields of molecular biology and cellular biology of cytokines. More specifically, the present invention relates to a methods of inhibiting or enhancing the TGF-β-Smad signaling pathway.

2. Description of the Related Art

The TGF-β family of polypeptide growth factors regulate cell division, differentiation, motility, adhesion and death in virtually all metazoan tissues[39,44,46,51,53,56]. Members of this family include the TGF-βs, the activins, the bone morphogenetic proteins (BMPs) and other related factors. Signal transduction by these factors involves three classes of molecules: a family of membrane receptor serine/threonine kinases, a family of cytoplasmic proteins, the Smad family, that serve as substrates for these receptors, and nuclear DNA-binding factors that associate with Smads forming transcriptional complexes[43,52]. Signaling is initiated by binding of the growth factor to a specific pair of receptor kinases, an event that induces the phosphorylation and activation of one kinase, known as the "type I receptor", by the other kinase or "type II receptor"[65]. The activated type I receptor phosphorylates a subset of Smads, known as "receptor-regulated Smads" (R-Smads), which then move into the nucleus[43,52]. On their way to the nucleus, R-Smads associate with the related protein Smad4[9], a tumor suppressor gene product[1]. In the nucleus, this complex may associate with specific DNA-binding proteins that direct it to the regulatory region of target genes. The first identified Smad-associated DNA-binding factor was the forkhead family member Fast1, which mediates activation of Mix.2 in response to activin-type signals during Xenopus embryogenesis[36]. The integrity of this signaling network is essential for normal development and tissue homeostasis, and its disruption by mutation underlies several human inherited disorders and cancer[43,52].

Because of the diversity of processes controlled by different TGF-β family members, there is an intense interest in elucidating the basis for the specificity of their signal transduction pathways. The TGF-β and activin type I receptors, which have nearly identical kinase domains[31,60], interact with and phosphorylate Smad2 (or the closely related Smad3)[16,40,30,54,8] which then interacts with DNA-binding factors such as Fast1[34,33,49]. The BMP receptors interact with Smad1 (or the closely related Smads 5, 8 or, in Drosophila, Mad)[35,40,11,14,18,10] which do not recognize Fast1[36]. Although the TGF-β and BMP pathways are well segregated from each other, their receptors and R-Smads are structurally very similar. The specificity of the receptor and Smad interactions in each pathway may therefore be dictated by discrete structural elements.

The Smad4/DPC4 tumor suppressor[1] is inactivated in nearly one half of pancreatic carcinomas[2] and to a lesser extent in a other cancers[2-4]. Smad4/DPC4, and the related tumor suppressor Smad2, belong to the Smad family of proteins which mediate TGFβ/activin/bone morphogenetic protein (BMP)-2/4 cytokine superfamily signaling from the receptor serine/threonine protein kinases at the cell surface to the nucleus[5-7]. Smad proteins, which get phosphorylated by the activated receptor, propagate the signal, in part, through homo-oligomeric and hetero-oligomeric interactions[8,3]. Smad4/DPC4 plays a central role as it is the shared hetero-oligomerization partner of the other Smads. The conserved C-terminal domains of Smads are sufficient for inducing most of the ligand-specific effects, and are the primary targets of tumorigenic inactivation.

The conserved C-terminal domain of Smad family members is the likely effector domain, whereas the conserved N-terminal domain is the likely negative regulator of activity[14]. When overexpressed in a Smad4/DPC4–/– cell line, the Smad4/DPC4 C-terminal domain activates the transcription of TGF-β responsive genes and results in growth arrest in a ligand-independent manner, paralleling the effects of the TGF-β ligand[9]. In addition, microinjection of mRNAs encoding the C-terminal domain of Smad2 into Xenopus embryos can induce a mesoderm response that mimics the effects of the full-length protein[16]. Furthermore, the Smad4/DPC4-C-terminal domain fused to a heterologous DNA-binding domain can activate gene expression from a reporter construct[14]. Consistent with the Smad C-terminal domain being the main effector domain, the majority (10 out of 13) of the tumorigenic missense mutations in Smad4/DPC4 and Smad2, as well as mutations isolated from Drosophila and C. elegans genetic screens map to the C-terminal domain.

The prior art is deficient in the lack of effective means of inhibiting or enhancing the TGF-β-Smad signaling pathway. The present invention fulfills this longstanding need and desire in the art.

SUMMARY OF THE INVENTION

It is an object of the present invention to use the L3 loop of the Smad proteins 1, 2, 3, 4, 5 or 6 or the C-terminal tail of Smad proteins 1, 2, 3, 4 or 5 in protein-interaction assays to screen for agents that increase or decrease Smad interactions via these regions.

It is another object of the present invention to provide a method of screening for drugs that interfere with or enhance signaling by TGF-β or other members of the TGF-β family that signal through Smad proteins.

It is another object of the present invention to provide a screening method that utilizes high specificity peptide-Smad interactions and peptide receptor interactions and is suitable for adaptation to high throughput assays.

In one embodiment of the present invention, there is provided a method of screening for drugs which enhance or inhibit Smad binding to a complementary Smad via the L3 loop region, comprising the steps of: a) producing a synthetic Smad polypeptide encompassing the L3 loop region; b) attaching a detectable label onto this polypeptide; c) contacting the synthetic L3 loop polypeptide with a complementary Smad protein immobilized on a solid support; d) measuring the amount of labeled L3 loop polypeptide bound; e) in parallel to steps (c) and (d), conducting these same steps in the presence of a test substance; and f)

comparing the amount of L3 loop polypeptide bound in the presence of a test substance with the amount bound in the absence of test substance so as to identify test substances that either increase L3 loop polypeptide binding to the Smad protein or decrease L3 loop polypeptide binding to the Smad protein.

In another embodiment of the present invention, there is provided a method of screening for drugs which enhance or inhibit Smad binding to a complementary Smad via the L3 loop region, comprising the steps of: a) producing a synthetic Smad polypeptide, encompassing the L3 loop region as defined by the crystal structure of the Smad4/DPC4 C-terminal domain; b) producing this polypeptide containing a chemical group that allows immobilization; c) contacting this L3 loop polypeptide with a labeled complementary Smad protein; d) measuring the amount of labeled Smad protein bound to the L3 loop polypeptide; e) in parallel to steps (c) and (d), conducting these same steps in the presence of a test substance; and f) comparing the amount of Smad protein bound in the presence of a test substance with the amount bound in the absence of test substance in order to identify test substances that either increase L3 loop polypeptide binding to the Smad protein or decrease L3 loop polypeptide binding to the Smad protein.

In yet another embodiment of the present invention, there is provided a method of screening for drugs which enhance or inhibit Smad4 binding to a complementary Smad via the C-terminal phosphorylated tail ("C-tail") of this Smad, comprising the steps of: a) producing a synthetic polypeptide corresponding to the C-terminal tail of a given Smad encompassing the C-terminal tail that follows the H5 alpha-helix as defined by the crystal structure of the Smad4/DPC-terminal domain; b) attaching a detectable label onto this polypeptide; c) contacting this C-tail polypeptide with Smad4 protein immobilized on a solid support; d) measuring the amount of labeled C-tail polypeptide that is bound to Smad4; e) in parallel to steps (c) and (d), conducting these same steps in the presence of a test substance; and f) comparing the amount of C-tail bound in the presence of a test substance with the amount bound in the absence of the substance in order to identify test substances that either increase C-tail polypeptide binding to the Smad protein or decrease C-tail polypeptide binding to the Smad protein.

In yet another embodiment of the present invention, there is provided a method of screening for drugs which enhance or inhibit Smad4 binding to a complementary Smad via the C-terminal phosphorylated tail ("C-tail") of this Smad, comprising the steps of: a) producing a synthetic polypeptide corresponding to the C-terminal tail of a given Smad encompassing the C-terminal tail that follows the H5 alpha-helix as defined by the crystal structure of the Smad4/DPC4 C-terminal domain; b) producing this polypeptide containing a chemical group that allows immobilization; c) contacting this derivative C-tail polypeptide with the labeled Smad4 protein; d) measuring the amount of labeled Smad4 bound to the C-tail polypeptide; e) in parallel to steps (c) and (d), conducting these same steps, in the presence of a test substance; f) comparing the amount of Smad4 bound in the presence of a test substance, with the amount bound in the absence of test substance in order to identify test substances that either increase Smad4 binding to the C-tail polypeptide or decrease Smad4 binding to the C-tail polypeptide.

In yet another embodiment of the present invention, there is provided a method of screening for drugs which enhance or inhibit Smad binding to a receptor of the TGF-β family, comprising the steps of: a) producing a synthetic polypeptide corresponding to the amino acid sequence of a given Smad encompassing the L3 loop region as defined by the crystal structure of the Smad4/DPC4 C-terminal domain; b) attaching a detectable label onto this polypeptide; c) contacting this L3 loop polypeptide with a receptor cytoplasmic domain protein such as a Smad1-derived L3 loop polypeptide with the bone morphogenetic protein receptor cytoplasmic domain, or contacting a Smad2-derived L3 loop polypeptide with the TGF-β receptor cytoplasmic domain) immobilized on a solid support; d) measuring the amount of labeled L3 loop polypeptide; e) in parallel to steps (c) and (d), conducting these same steps, in the presence of a test substance; and f) comparing the amount of L3 loop polypeptide bound in the presence of a test substance with the amount bound in the absence of test substance in order to identify test substances that either increase L3 loop polypeptide binding to the receptor or decrease L3 loop polypeptide binding to the receptor.

In yet another embodiment of the present invention, there is provided a method of screening for drugs which enhance or inhibit binding of a Smad N-terminal domain to the C-terminal domain of the same Smad protein, comprising the steps of: a) producing recombinant forms of the N-terminal domain and C-terminal domain polypeptides, with one containing a detectable label and the other containing a moiety allowing immobilization onto a solid support; b) contacting the recombinant N-terminal domain polypeptide with the C-terminal domain polypeptide; c) measuring the amount of labeled domain polypeptide bound; d) in parallel to steps (b) and (c), conducting these same steps, in the presence of a test substance; e) comparing the amount of labeled polypeptide bound in the presence of a test substance with the amount bound in the absence of a test substance so as to identify test substances that either increase N-terminal domain binding to the C-terminal domain or decrease N-terminal domain binding to the C-terminal domain.

Smad2 and Smad4 are related tumor suppressors that, in response to TGF-β, form a complex that mediates transcriptional and growth inhibitory responses. The effector function of Smad2 and Smad4 is located in their conserved C-terminal domain (C domain) and inhibited by the presence of their N-terminal domains (N domain). The inhibitory function of the N domain is shown herein to involve a physical interaction with the C domain, preventing the association of Smad2 with Smad4. This inhibitory function is increased in tumor derived forms of Smad2 and 4 that carry a missense mutation in a conserved N domain arginine. The mutant N domains have increased affinity for their respective C domains, inhibit Smad2-Smad4 interaction and prevent TGF-β-induced Smad2-Smad4 association and signaling. Whereas mutations in the C domain disrupt the effector function of the Smads, the N domain arginine mutations inhibit Smad signaling through a gain of autoinhibitory function. Gain of autoinhibitory function provides a novel mechanism of tumor suppressor inactivation.

In the present invention, the crystal structure of the C-terminal domain (CTD) of the Smad4/DPC4 tumor suppressor, was determined at 2.5 Å resolution and revealed that the Smad4/DPC4-C-terminal domain forms a crystallographic trimer through a conserved protein-protein interface to which the majority of the tumor-derived missense mutations map. These mutations disrupt homo-oligomerization in vitro and in vivo, suggesting that the trimeric assembly of the Smad4/DPC4 C-terminal domain is a critical function in signaling that is targeted by tumorigenic mutations.

Other and further aspects, features, and advantages of the present invention will be apparent from the following description of the presently preferred embodiments of the invention given for the purpose of disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the matter in which the above-recited features, advantages and objects of. the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 2A–2B show the sequence alignment of C-terminal domains of five human Smads[1,8,10] (Smad1, 2, 3, 5 and Smad4/DPC4) and homologues from Drosophila[18] (Mad) and C. elegans[19] (Sma-2, 3, 4), with the Smad4/DPC4-C-terminal domain secondary structure elements indicated below the sequences. Residues that are more than 40% solvent-exposed, have no significant structural roles, and are conserved in at least 6 out of the 9 aligned sequences are highlighted in gray. The 14 missense mutations (boxed) tabulated above the alignment include tumor-derived Smad4/DPC4 and Smad2 mutations[1,2,4,12,17,28], as well as mutations from Drosophila and C. elegans genetic screens[18,19] (developmental mutations, double underlined). The residues where these mutations occur are in bold face and underlined. FIG. 2C shows the mapping of both the missense mutations and the highly conserved and solvent-exposed residues identifies the three-helix bundle and the three-loop/helix region as regions likely to be important for macromolecular recognition events that mediate Smad function. Color coding is the same as in FIGS. 2A–2B. The amino acid substitution and the residue number from the mutated Smad family members other than Smad4/DPC4 are shown in parentheses. The three structural mutations (Arg441Pro from Smad4/DPC4, Leu440Arg and Pro445H from Smad2) are not shown.

FIG. 3 shows that in the crystals, the Smad4/DPC4 C-terminal domain forms a trimer that is targeted by tumorigenic mutations and is likely to be important for Smad function.

FIG. 4 shows the the size exclusion chromatography indicating that the wild type full-length Smad4/DPC4, but not the tumor-derived mutants, has an apparent molecular weight consistent with that of a trimer.

FIG. 5 shows that one face of the disk-like trimer structure may mediate hetero-oligomerization.

FIG. 6 shows an analysis of Smad4 and Smad2 domain interactions.

FIG. 8 shows the effect of N domain deletion and agonist-induced phosphorylation on Smad2-Smad4 interaction.

FIG. 9 shows the biological activity of Smad2 and Smad4 containing tumor-derived N domain mutations.

FIG. 10 shows the gain of autoinhibitory function of Smad4 and Smad2 N domain mutants.

FIG. 12 shows the Smad2 association with the TGF-β receptor does not require its C-tail and is affected by Smad2 phosphorylation.

FIG. 14 shows that the L3 loop specifies Smad-receptor interaction.

FIG. 15A: The L3 loop of Smad2 is necessary for Smad2 phosphorylation in response to TGF-β. FIG. 15B: The L3 loop of Smad2 allows Smad1 to be phosphorylated in response to TGF-β, and the Smad2 C-tail supports optimal phosphorylation. FIG. 15C: The L3 loop and C-tail of Smad1 allows Smad2 to be phosphorylated in response to BMP. Smad expression level was demonstrated by anti-Flag immunoblotting prior to inducibility determinations (data not shown). To determine inducibility of Smad phosphorylation by TGF-β1 or BMP4, R1B/L17 cells were transfected with the indicated Flag-tagged Smad constructs alone (−) or together (+) with either TβR-I or BMPR-IB and BMPR-II. Cells were labeled with [$^{32}$P]orthophosphate for 2 hours and then incubated with (+) or without (−) TGF-β1 or BMP4 for 30 minutes. In parallel transfections, Smad proteins immunoprecipitated from cell lysates using anti-Flag antibody were resolved by SDS-PAGE and transferred onto membrane for western blotting using anti-Flag antibody. Arrow indicates Smad proteins.

FIG. 19 shows that exchanging the L45 loops switches the signaling specificity of TβR-I and BMPR-IB.

FIG. 21A shows the sequence alignment of the MH2 domains of Smad1, 2 and 4, with the Smad4 MH2 domain secondary structure elements indicated below. Identical residues are boxed. Subtype-specific residues map to α-helix 1 (yellow), α-helix 2 and its vicinity (purple), the L3 loop (red), and immediately upstream of the C-terminal receptor phosphorylation motif SS(V/M)S (green). The remaining subtype-specific residues (gray) are scattered in the primary sequence but clustered in the crystal structure near the point of connection to the N-terminal half of the molecule[57].

FIG. 23 shows the α-helix 2 of Smad2 specifies the interaction with the DNA-binding factor Fast1.

DETAILED DESCRIPTION OF THE INVENTION

Definitions

Figure 1:
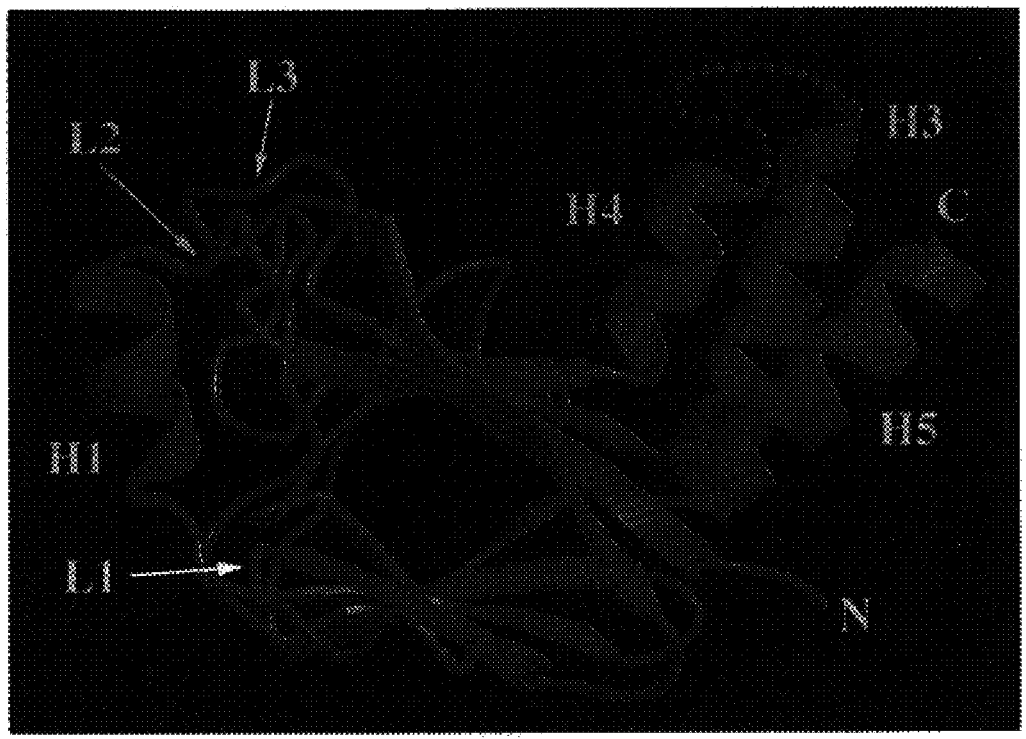
FIG. 1 shows the structure of the Smad4/DPC4-C-terminal domain consists of a β-sandwich with a three-helix bundle on one end and a collection of three large loops and an α helix on the other end. Schematic representation of the structure is viewed along the edge of the β-sandwich. The dotted line represents the disordered region between the H3 and H4 helices. Figures were prepared with the programs MOLSCRIPT[26] and RASTER3D[27].

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specicif gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the -10 and -35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA molecule or gene can be used to transform a host using any of the techniques commonly known to those of ordinary skill in the art. One preferred embodiment is the use of a vectors containing coding sequences for a gene for purposes of prokaryotic transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and more preferentially, plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous' region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

In addition, the invention may also include fragments (e.g., antigenic fragments or enzymatically functional fragments) of a gene. As used herein, "fragment," as applied to a polypeptide, will ordinarily be at least 10 residues, more typically at least 20 residues, and preferably at least 30 (e.g., 50) residues in length, but less than the entire, intact sequence. Fragments can be generated by methods known to those skilled in the art, e.g., by enzymatic digestion of naturally occurring or recombinant proteins, by recombinant DNA techniques using an expression vector that encodes a defined fragment, or by chemical synthesis. The ability of a candidate fragment to exhibit a characteristic (e.g., binding to a specific antibody, or exhibiting partial enzymatic or catalytic activity) can be assessed by methods described herein. Purified fragments or antigenic fragments can be used to generate new regulatory enzymes using multiple functional fragments from different enzymes, as well as to generate antibodies, by employing standard protocols known to those skilled in the art.

A standard Northern blot assay can be used to ascertain the relative amounts of mRNA in a cell or tissue obtained from plant or other transgenic tissue, in accordance with conventional Northern hybridization techniques known to those persons of ordinary skill in the art. Alternatively, a standard Southern blot assay may be used to confirm the presence and the copy number of the gene in transgenic systems, in accordance with conventional Southern hybridization techniques known to those of ordinary skill in the art. Both the Northern blot and Southern blot use a hybridization probe, e.g. radiolabelled cDNA, either containing the full-length, single stranded DNA or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

The following specific definitions are given for the purposes of describing the art to which the present invention pertains specifically and distinctly. Any terms not specifically defined herein have the meaning generally known in this art.

As used herein, the term "Smad4/DPC4 and Smad2" shall refer to two related cytoplasmic proteins of known amino acid sequence that mediate the effects of TGF-β and that form a complex with each other in response to stimulation with TGF-β.

As used herein, the term "receptor-regulated Smad polypeptide" or "receptor-regulated Smad protein" shall refer to a minimum of seven cytoplasmic proteins of known amino acid sequence that mediate the effects of TGF-β and are contacted by the TGF-β receptors.

As used herein, the term "TGFβ/activin/bone morphogenetic protein (BMP)-2/4 cytokine superfamily" shall refer to a family of related polypeptide growth factors of known amino acid sequence.

As used herein, the term "protein-interaction assay" shall refer to an assay that measures, or depends upon, the specific association of one protein with another. The association may occur between these proteins in solution or inside cells.

As used herein, the term "effector function" shall refer to the ability to generate or activate specific cellular responses.

As used herein, the term "autoinhibitory function" shall refer to the ability of one portion of the Smad protein to inhibit or repress the effector function of another portion of the same protein.

As used herein, the term "tumor-derived missense mutation" shall refer to an amino acid change originated by a single base mutation found in a human tumor sample.

As used herein, the term "homo-oligomerization and hetero-oligomerization" shall refer to the process and ability of a Smad protein to associate with itself, i.e., homo-oligomerize, or to associate with another Smad protein, i.e., hetero-oligomerize.

As used herein, the term "L3 loop region" shall refer to a region in the carboxy-terminal domain of Smad proteins whose 10 length and boundries are defined by the crystal structure of the Smad4/DPC4 C-terminal domain and is expressed on the surface of this domain. Mutation of the L3 loop region prevents Smad hetero-oligomerization and receptor association without preventing Smad homo-oligomerization.

As used herein, the term "loop/helix region" shall refer to a Smad C-terminal domain region defined by the crystal structure of Smad4/DPC4 and involved in Smad homo-oligomerization by interaction with the three helix bundle.

As used herein, the term "L45 loop region" shall refer to a region of known amino acid sequence in the TGF-β receptors that is required for these receptors to contact and recognize receptor-regulated Smads.

As used herein, the term "α-helix 2 of the MH2 domain" shall refer to a region of known amino acid sequence in the Smad proteins that is required by these proteins to contact and recognize DNA binding factors.

As used herein, solid support shall refer to a matrix to which a protein or nucleic acid molecule may be attached, for example, by covalent means. For purposes of example, a solid support may comprise matrices consisting of agarose, sepharose, polyacrylamide, nitrocellulose, polystyrene and PVDF.

As used herein, the term "β-sandwich" shall refer to the core structure of the C-terminal domain of the Smad protein as defined by the crystal structure of Smad4.

As used herein, the term "three-helix bundle" shall refer to a region of the Smad protein C-terminal domain defined by the crystal structure of Smad4/DPC4 and is involved in Smad-homo-oligomerization by interaction with the loop/helix region.

As used herein, the term "invariant" shall refer to an amino acid residue that remains the same in all Smad proteins at a given position in their amino acid sequence.

Mediation of growth inhibitory responses (such as cell cycle arrest, terminal differentiation and/or apoptosis) and the induction of extracellular matrix proteins (such as collagens, fibronectin, proteoglycan) are important biochemical events. In cancer, mutation in the Smad2 or Smad4 receptor is known to inactivate certain biochemical pathways which deprive the cell of growth inhibitory mechanisms. In fibrotic disorders of the kidney, liver and lung, the TGFβ-Smad pathway is hyperactive. Thus, agents which enhance the function of the pathway would be beneficial in the treatment of cancer whereas agents that inhibit the pathway would be beneficial in the treatment of fibrosis. The present invention discloses that such manipulation of the TGFβ-Smad pathway is possible by focusing on the interaction between specific receptor-activated Smads. These Smads interact with the receptor through specific contacts as described in detail below. Upon phosphorylation by the receptor, these Smads dissociate and form a complex with Smad4. Smad4 itself is not a receptor substrate but its association with Smads 1, 2 or others is essential for the transcriptional activity of these complexes.

The present invention discloses which regions of the Smad protein are involved in the Smad1-receptor or Smad2-receptor interaction and which regions of the Smad protein are involved in the Smad1-Smad4 interation. Discrete differences in the amino acid sequence of specific regions within these domains dictate whether a Smad protein will interact with a given TFGβ family receptor. Structures within this domain also mediate the crucial interaction between Smad4 and Smads 1, 2, 3 or 5.

The present invention discloses that the L3 loop region of the Smad4 protein is exposed on the surface of Smad4 and is conserved in all other Smads. However, certain amino acid residues within this loop vary in each Smad. Furthermore, of several mutations previously identified in inactive alleles of Smad, three fall in the L3 loop of these Smads. The L3 loop mutations do not affect the homotrimeric contacts between the Smad subunits but do eliminate the Smad4 interaction with other Smads. Thus, the L3 loop is the structural motif that mediates Smad4 contact with Smads 1, 2, 3 and 5. The L3 loop is also required for Smad 1, 2, 3 or 5 interaction with the receptor. As discussed below, the crystal structure of Smad4 reveals how the C-terminal tail containing the last few amino acids of a Smad emerges from the globular structure. In Smads 1, 2, 3 and 5, this tail contains the receptor phosphorylation sites. The crystal structure of Smad4 illustrates exactly where this tail starts.

The present invention is directed to the use of specfic L3 loop peptides or C-tail peptides as ligands for recombinant forms of other Smads, e.g., the Smad1 L3 loop as a ligand of Smad4, the Smad4 L3 loop as a ligand of Smad1, or the L3 loop as a ligand of type I receptors. Using the loop region alone as a ligand affords greater specificity in the assays. This assay can be used to screen for drugs which either enhance or inhibit Smad binding.

Thus, the present invention provides a method of testing compounds, comprising the steps of: a) providing (i) a Smad4 polypeptide comprising the L3 loop region, (ii) a complementary Smad polypeptide, and (iii) a compound to be tested; (b) contacting said Smad4 polypeptide with said complementary Smad polypeptide under conditions where binding can take place, wherein said contacting is performed in the presence and absence of said compound; and c) detecting an increase or decrease in binding of said Smad4 polypeptide to said complementary Smad polypeptide in the presence of said compound. Preferably, the complementary Smad polypeptide is selected from the group consisting of Smad1, Smad2, Smad3, Smad5 and Smad8.

The present invention also provides a method of testing compounds, comprising the steps of: a) providing (i) two Smad polypeptides from the same Smad family comprising the C-terminal domains of each, and (ii) a compound to be tested; b) contacting said Smad polypeptides under conditions where binding can take place, wherein said contacting is performed in the presence and absence of said compound; and c) detecting an increase or decrease in binding of said Smad polypeptides to each other in the presence of said compound. Preferably, the families of Smad polypeptides are selected from the group consisting of Smad1, Smad2, Smad3, Smad4, Smad5, Smad6, Smad7 and Smad8.

The present invention also provides a method of testing compounds, comprising the steps of: a) providing (i) a Smad polypeptide comprising the C-terminal domain, (ii) a polypeptide comprising the L45 loop of the kinase domain corresponding to a receptor of the TGF-_ or BMP family, and (iii) a test compound; b) contacting said Smad polypeptide with said receptor polypeptide under conditions where phosphorylation can take place, wherein said contacting is performed in the presence and absence of said compound; and c) detecting an increase or decrease in the phosphorylation of said Smad polypeptide in the presence of said compound. Preferably, the Smad polypeptide is selected from the group consisting of Smad1, Smad2, Smad3, Smad5 and Smad8.

The present invention also provides a method of testing compounds, comprising the steps of: a) providing (i) a Smad polypeptide comprising the α-helix 2 of the MH2 domain, (ii) a DNA binding polypeptide, and (iii) a compound to be tested; b) contacting said Smad polypeptide with said DNA binding polypeptide under conditions where binding can take place, wherein said contacting is performed in the presence and absence of said compound; and c) detecting whether there is an increase in binding of said Smad polypeptide to said DNA binding polypeptide in the presence of said compound. Preferably, the Smad polypeptide is selected from the group consisting of Smad1, Smad2, Smad3, Smad4, Smad5 and Smad8. Preferably, the DNA binding polypeptide is selected from the group consisting of FAST1 and homologues of FAST1.

The present invention also provides a method of testing compounds, comprising the steps of: a) providing (i) two Smad polypeptides comprising the C-terminus of each, (ii) a Smad polypeptide comprising the N-terminal domain, and (iii) a compound to be tested; b) contacting said Smad C-terminus polypeptides in the presence of said Smad N-terminal domain under conditions where binding can take place, wherein said contacting is performed in the presence and absence of said compound; and c) detecting whether there is an increase or decrease in binding of said Smad C-terminus domains in the presence of said compound due to inhibition of the autoinhibitory function of the N-terminal domain by said compound. Preferably, the Smad polypeptide is selected from the group consisting of Smad1, Smad2, Smad3, Smad4, Smad5 and Smad8.

The present invention also provides a method of testing compounds, comprising the steps of: a) providing (i) a Smad polypeptide comprising the C-terminal domain, (ii) a polypeptide comprising the L45 loop of the kinase domain corresponding to a receptor of the TGF-_ or BMP family, and (iii) a test compound; b) contacting said Smad polypeptide with said receptor polypeptide under conditions where binding can take place, wherein said contacting is performed in the presence and absence of said compound; and c) detecting an increase or decrease in the binding of said Smad polypeptide to said kinase domain in the presence of said compound. Preferably, the Smad polypeptide is selected from the group consisting of Smad1, Smad2, Smad3, Smad5 and Smad8.

The compounds tested in the methods of the present invention may be used to treat a variety of ailments. Representative ailments include pancreatic cancer, breast cancer, ovarian cancer, colon cancer, esophageal cancer, head and neck cancers, fibrosis of the kidney, fibrosis of the liver, fibrosis of the lung, Alzheimer's disease, memory loss, inflammation, wound healing, bone growth, immunoregulation, blood cell formation and atherosclerosis.

A person having ordinary skill in this art would readily recognize that a variety of detection techniques may be utilized in the methods of the present invention. Representative detection techniques include solid support immobilization of one or the other polypeptides, labeling of one or the other polypeptides, scintillation proximity, homogeneous time resolved fluorescence, fluorescence resonance energy transfer and fluorescence polarization.

The following examples are given for the purpose of illustrating various embodiments of the invention and are not meant to limit the present invention in any fashion.

EXAMPLE 1

Protein Expression and Purification

Recombinant Smad4/DPC4-C-terminal domain, corresponding to residues 319–552 (SEQ ID NO:1), was overexpressed at room temperature in *Escherichia coli* using a pET vector (Novagen). The Smad4/DPC4-C-terminal domain in the soluble fraction of the *E. coli* lysate was partially purified on a Q-Sepharose column, was concentrated by ultrafiltration and was further purified by gel filtration chromatography (Superdex75 column) and by anion-exchange chromatography (Source 15Q column).

EXAMPLE 2

Crystallization

Initial crystals were grown at 4° C. by the hanging-drop vapour-diffusion method, by mixing the 10–15 mg/ml protein solution with an equal volume of the reservoir solution containing 100 mM MES, 25% monomethylether PEG5000 (MPEG5000), and 200 mM $(NH_4)_2SO_4$(pH6.5). Crystals suitable for diffraction studies were grown using streak-seeding and macroseeding methods[20]. The crystals form in the cubic space group $F4_132$ with a=b=c=199.6 Å, and contain one molecule in the asymmetric unit.

EXAMPLE 3

Data Collection and Processing

Diffraction data were collected using an R-AXISIIC imaging plate detector mounted on a Rigaku 200HB generator. Native1 and derivative data were collected at 8° C., and native2 data were collected at −170° C. with a crystal flash frozen in a buffer containing 20% glycerol and 25% MPEG5000. Heavy-atom soaks were performed in 50 mM HEPES, 25% MPEG, 160 mM $(NH_4)_2SO_4$, 100 mM NaCl, pH 6.1, containing one of the following heavy-atom solutions: 1.2 mM thimerosal for 12 hours, 3.0 mM $(CH_3)_3PbCOOCH_3$ for 3 days, and 2.0 mM uranyl acetate for 19 hours.

EXAMPLE 4

MIR Analysis, Model Building and Refinement

The heavy atom sites of the thimerosal derivative were determined by direct methods with the program SHELXS-90[21], and the heavy atom sites of the other derivatives were identified by difference fourier methods. Initial MIR phases calculated with the program MLPHARE[22] had a mean figure of merit of 0.62 to 3.2 Å, and they were improved with solvent flattening and histogram matching with the program SQUASH[23]. The MIR electron density maps had continuous electron density for the majority of the Smad4/DPC4-C-terminal domain polypeptide, with the exception of a 34 amino acid region between helices H3 and H4. A model was built into MIR electron density maps with the program O[24], it was refined by simulated annealing with the program X-PLOR[25], and it was checked by calculating X-PLOR omit maps in which 5–7% of the structure was deleted in each calculation and simulated annealing was used to reduce model bias. The refined model contains residues 319–543 (part of SEQ ID NO.:1) of human Smad4/DPC4 and 129 water molecules. Residues 544–552 (part of SEQ ID NO:1) at the C-terminus, and residues 457–491 (part of SEQ ID NO.:1) between helices H3 and H4 have no electron density in the maps and it is likely that these regions were disordered in the crystals.

EXAMPLE 5
In vivo Oligomerization Assays

The full-length Smad4/DPC4 and Smad2, Smad4/DPC4-C-terminal domain encoding amino acids 294–552 (SEQ ID NO.:1) and the Smad2-C-terminal domain encoding amino acids 248–467 (SEQ ID NO.:3) were subcloned into the mammalian expression vector pCMV5. All Smad4/DPC4 point mutations were generated by a polymerase chain reaction (PCR)-based method and were confirmed by DNA sequencing. Mammalian COS-1 cells were transiently transfected with the indicated FLAG- and HA-tagged constructs by the DEAE-dextran method. Two days after transfection, cells were incubated with 200 pM TGF-β1 for one hour. Cells were lysed and subjected to immunoprecipitation followed by immunoblot as described[9]. The wash buffers contained 150 mM NaCl for all immunoprecipitation experiments except for the homo-oligomerization assays of the full-length wild-type Smad4/DPC4 and point mutants, where 250 mM NaCl was employed to better differentiate the WT and mutant activities.

EXAMPLE 6
In vitro Oligomerization Assays

The full-length Smad4/DPC4 proteins, both wild-type and point mutants, were overexpressed at room temperature in E.coli using a pET vector (Novagen). Smad4/DPC4 protein in the soluble fraction of the E. coli lysate was partially purified by ion exchange chromatography (Q-Sepharose) and was applied to a gel filtration column (Superdex200) in 50 mM Tris, 200 mM NaCl, 5 mM DTT, pH 8.0. Aliquots from the fractions corresponding to molecular weight standards between 440 kDa and 25 kDa were taken for immunoblots with a rabbit polyclonal antibody raised against the Smad4/DPC4-C-terminal domain. The results were visualized with the ECL Western analysis and detection system (Amersham). In addition, the WT full-length Smad4/DPC4 was also cloned as a GST-fusion protein and purified to near homogeneity over a glutathione column. The fusion protein was then cleaved with Thrombin and the. Smad4/DPC4 protein was futher purified by anion-exchange chromatography (Source 15Q column).

To help understand how the Smad C-terminal domain functions in mediating TGFβ signaling and how its mutation in cancer inactivates the pathway, the crystal structure of the 234 amino acid Smad4/DPC4-C-terminal domain (residues 319 to 552 (SEQ ID NO.:1) at 2.5 Å resolution (TABLE 1) was determined. The structure consists of β-sandwich with twisted antiparallel β-sheets of five and six strands each (FIG. 1). One end of the β-sandwich is capped by a three-α-helix bundle (H3, H4, and H5 helices) that extends over the plane of the six-stranded β-sheet, at a roughly perpendicular angle; the other end of the β-sandwich is capped by a group of three large loops and an α-helix (L1, L2, L3 loops, and H1 helix; FIG. 1).

TABLE I

Statistics from the crystallographic analysis

| Data set | Native 1 (8° C.) | Native 2 (−170° C.) | Thimerosal | UO$_2$ (OAc)$_2$ | PbOAc |
|---|---|---|---|---|---|
| Resolution (Å) | 3.0 | 2.5 | 3.0 | 3.0 | 3.2 |
| Observations | 30691 | 39125 | 30572 | 23488 | 25150 |
| Unique reflections | 7189 | 11496 | 7073 | 6765 | 5759 |
| Data coverage (%) | 96.8 | 96.5 | 96.8 | 92.8 | 94.6 |
| R$_{sym}$ (%) | 6.5 | 3.7 | 4.8 | 8.5 | 10.0 |
| MIR analysis (20.0–3.2 Å): | | | | | |
| Mean isomorphous difference | | | 0.18 | 0.14 | 0.24 |
| Phasing power | | | 2.54 | 1.38 | 1.02 |

Refinement statistics:

| Resolution (Å) | Reflections (IFI > 2σ) | Protein atoms | Waters atoms | R-factor (%) | R-free (%) | RMSD bonds (Å) | RMSD angles (°) | B-factor (Å$^2$) |
|---|---|---|---|---|---|---|---|---|
| 7.0–2.5 | 10359 | 1522 | 129 | 20.9 | 28.6 | 0.010 | 1.66 | 3.29 |

Rsym = $\Sigma_h\Sigma_i|I_{h,i} - I_h|/\Sigma_{h\Sigma i} I_{h,i}$ for the intensity (I) of i observations of reflection h. Mean isomorphous difference = $\Sigma|F_{PH} - F_P|/\Sigma F_{PH}$, where $F_{PH}$ and $F_P$ are the derivative and native structure factors, respectively. Phasing power = $[(F_{H(calc)}^2/(F_{PH(obs)} - F_{PH(calc)})^2]^{1/2}$. Figure of merit = $|F(hkl)_{best}|/F(hkl)$. R-factor = $\Sigma|F_{obs} - F_{calc}|/\Sigma|F_{obs}|$, where $F_{obs}$ and $F_{calc}$ are the observed and calculated structure factors, respectively. R-Free = R-factor calculated using 5% of the reflection data chosen randomly and omitted from the start of refinement. RMSD: root mean square deviations from ideal geometry and root mean square variation in the B-factor of bonded atoms.

To simplify the presentation, the three large loops and α-helix, as well as portions of β-strands in their immediate vicinity are referred to collectively as the loop/helix region. The three α-helices of the bundle pack in an up-down-up orientation primarily through leucine residues. In-between the H3 and H4 helices, a 34 amino acid sequence that is rich in Ala (39%), Gly and Pro residues and is present only in Smad4/DPC4 and its C. elegans homologue Sma-4, is disordered in the crystals (residues 457 to 491(part of SEQ ID No:1)). In the loop/helix region, the L1, L2, and L3 loops of 7, 9, and 18 residues, respectively, and the H1 helix are mostly polar and pack through extended hydrogen bond networks. These hydrogen bonds are likely to contribute to the rigid structure of this region that is suggested by the well-defined electron density.

Figure 2A:
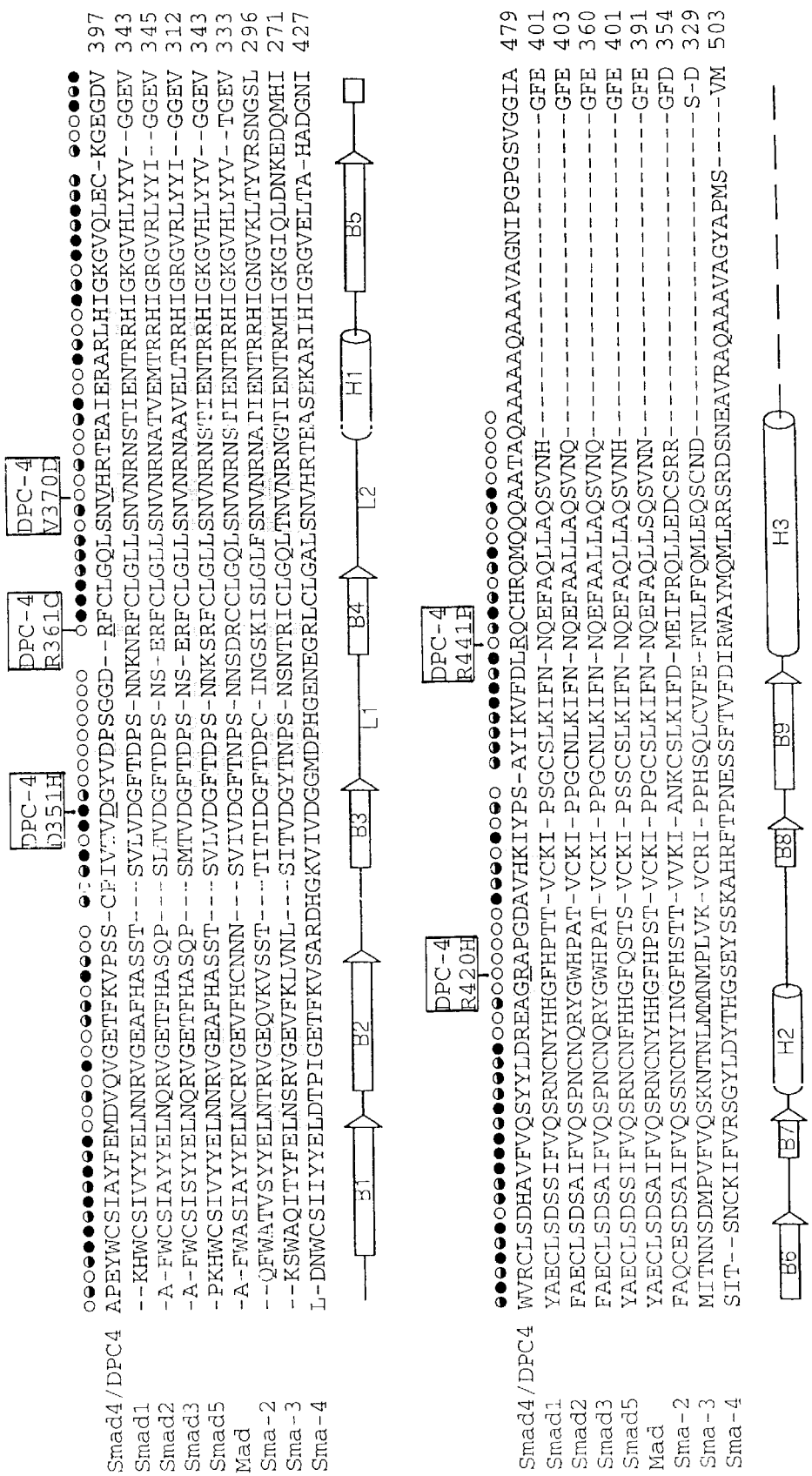
FIGS. 2A–2C shows the Smad C-terminal domains are highly conserved and are targeted by tumorigenic and developmental mutations.
Figure 2B:
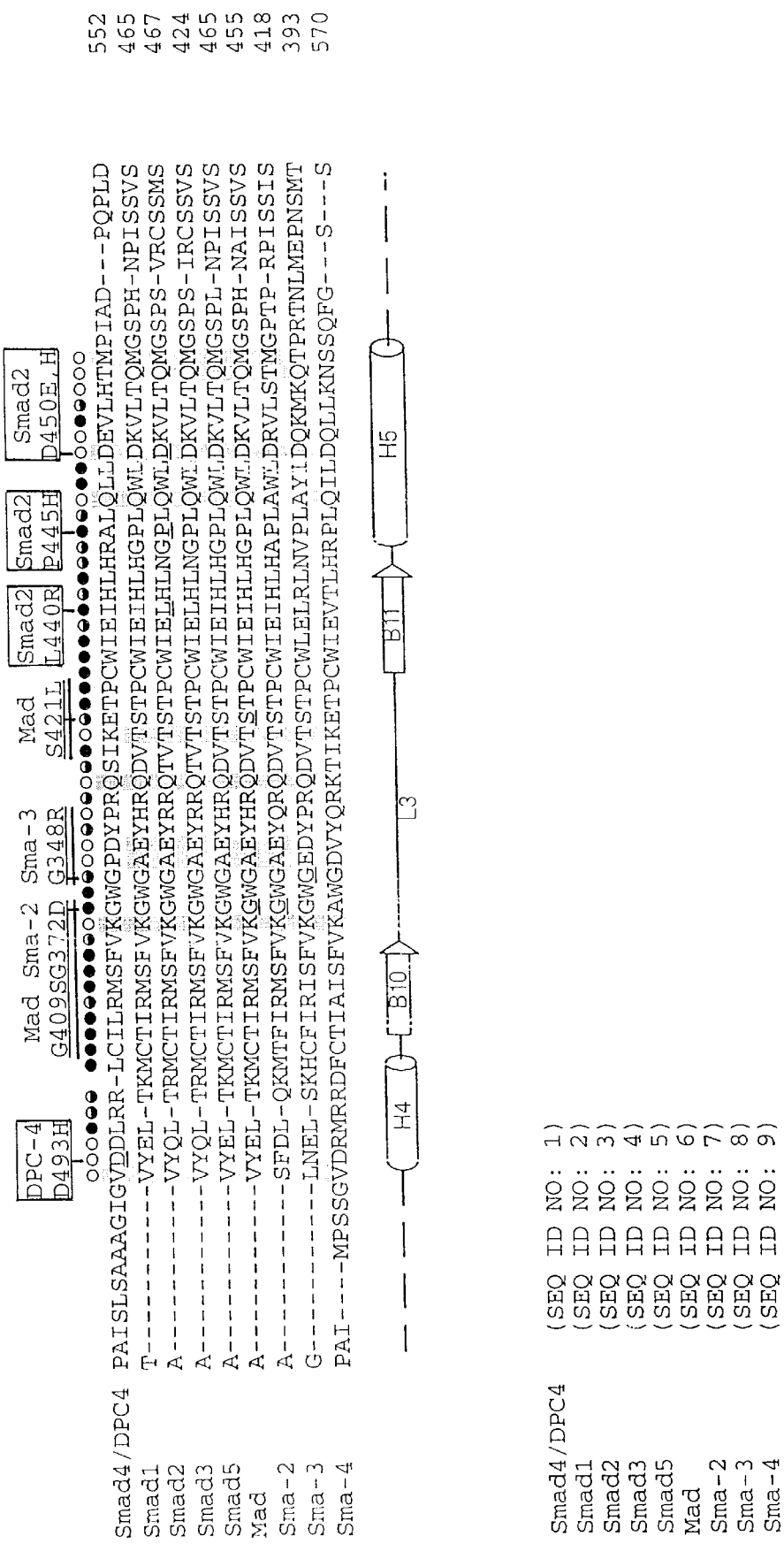
Figure 2C:
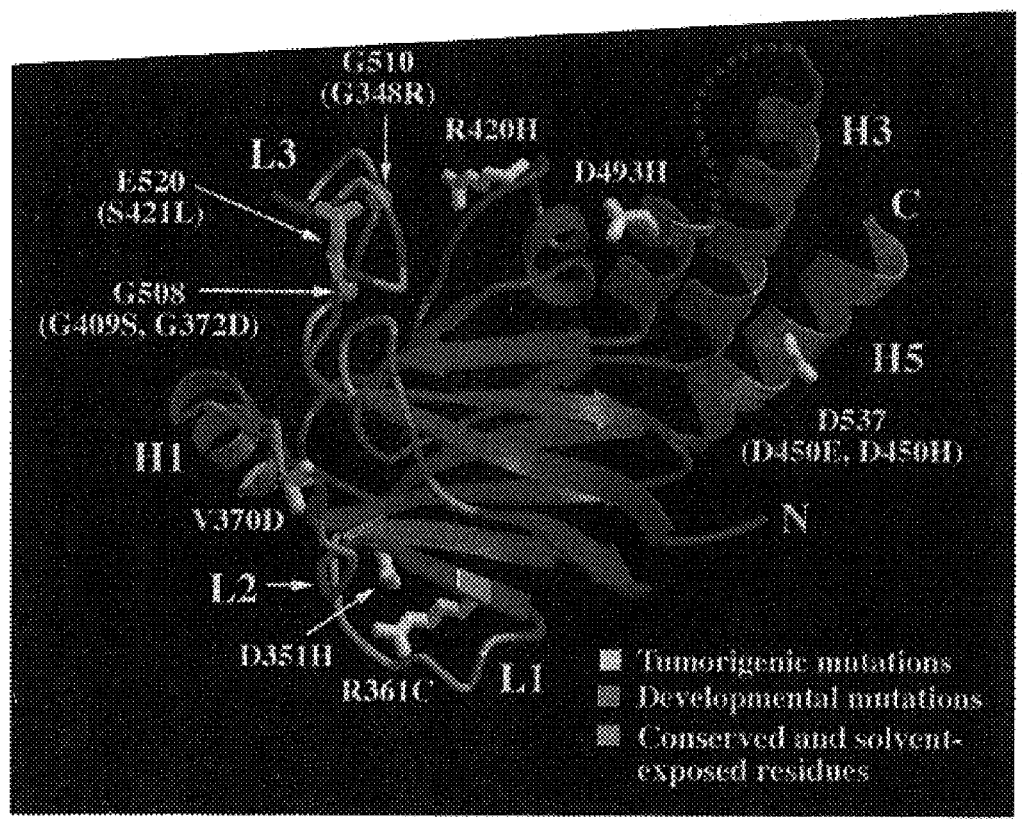

Smad proteins are highly conserved within the family and across species, with Smad4/DPC4 and its C. elegans homologue, Sma-4, representing a somewhat divergent subtype which still retains about 40% identity with other family members[5-7] (FIGS. 2A–2B). Many of the conserved residues have structural roles. These include the hydrophobic residues that make up the hydrophobic core of the β-sandwich and of the three-helix bundle, as well as many of the polar residues that form the hydrogen bond networks important for the structure of the loop/helix region. Examples of the latter group are the invariant Arg372 and Arg380 residues from the H1 helix making 4 and 3 charge stabilized hydrogen bonds, respectively. Many other highly conserved residues are solvent-exposed and have no apparent structure-stabilizing roles. They are thus candidates for functional residues that may mediate macromolecular interactions important for the function of Smad proteins. The structure reveals that these candidate functional residues, which are highlighted in FIG. 2C, show a strong tendency to cluster at the loop/helix region and the three-helix bundle.

Besides sequence conservation, another indication that the loop/helix region and the three-helix bundle are functionally important comes from an analysis of the 9 tumor-derived missense mutations, some observed multiple times, in the C-terminal domains of the Smad4/DPC4 and Smad2 tumor suppressors. Excluding three mutations that map to structural residues, 5 of the 6 tumor-derived missense mutations map to either the loop/helix region or to the three helix bundle: the Smad4/DPC4 mutations Asp351His[2], Arg361Cys[17], and Val370Asp[17] map to the loop/helix region, whereas the Smad4/DPC4 mutation Asp493His[1] and the Smad2 mutation Asp450Glu[12] (corresponding to Asp537 of Smad4/DPC4) map to the three-helix bundle. These mutations may deprive the C-terminal domain of critical intermolecular contacts.

The one mutation that does not map to either region is Arg420His from Smad4/DPC4, which instead maps to the side of the β-sandwich (H2 helix), a region that is not as well conserved. The remaining three mutations map to structural residues: the Smad2 Leu440Arg mutation (corresponding to Ile527 of Smad4/DPC4) in the hydrophobic core of the β-sandwich likely disrupts the packing in the hydrophobic core; the Smad4/DPC4 Arg441Pro mutation at the three-helix bundle likely disrupts the H3 helix because of the introduction of a proline in the midst of the helix; and the Smad2 Pro445His mutation (corresponding to Ala532 in Smad4/DPC4), also at the three-helix bundle, likely disrupts the packing between the three-helix bundle and the β-sandwich as there is little space for the bigger histidine side chain in this portion of the hydrophobic core.

Additional support for the functional significance of the loop/helix region is provided by mutations in Drosophila and *C. elegans* that produce null or severe developmental phenotypes[18,19]. These developmental mutations map to Gly508 (Drosophila Mad, *C. elegans* Sma-2), Gly510 (Sma-3), and Glu520 (Mad) of the L3 loop in the loop/helix region (FIG. 2C). Thus, the locations of conserved, solvent-exposed residues and the locations of mutations derived from tumors or from Drosophila and *C. elegans* genetic screens, taken together, point to the loop/helix region and the three-helix bundle as playing a critical role in mediating Smad activities.

Because the Smad C-terminal domains can mediate most of the biological effects of the full-length proteins, the Smad4/DPC4-C-terminal domain was tested for the homo-oligomerization activity. Initial co-immunoprecipitation experiments using extracts from COS cells transfected with differentially tagged Smad4/DPC4-C-terminal domain constructs showed that the Smad4/DPC4-C-terminal domain retained the ability to form homo-oligomers when overexpressed (FIG. 3D), suggesting that. the C-terminal domain may contain a primary homo-oligomerization activity. However, the full-length Smad4/DPC4 homo-oligomers are more stable than the Smad4/DPC4-C-terminal domain homo-oligomers in vivo, suggesting that residues N-terminal to the Smad4/DPC4-C-terminal domain are likely to contribute to homo-oligomerization.

Figure 3A:
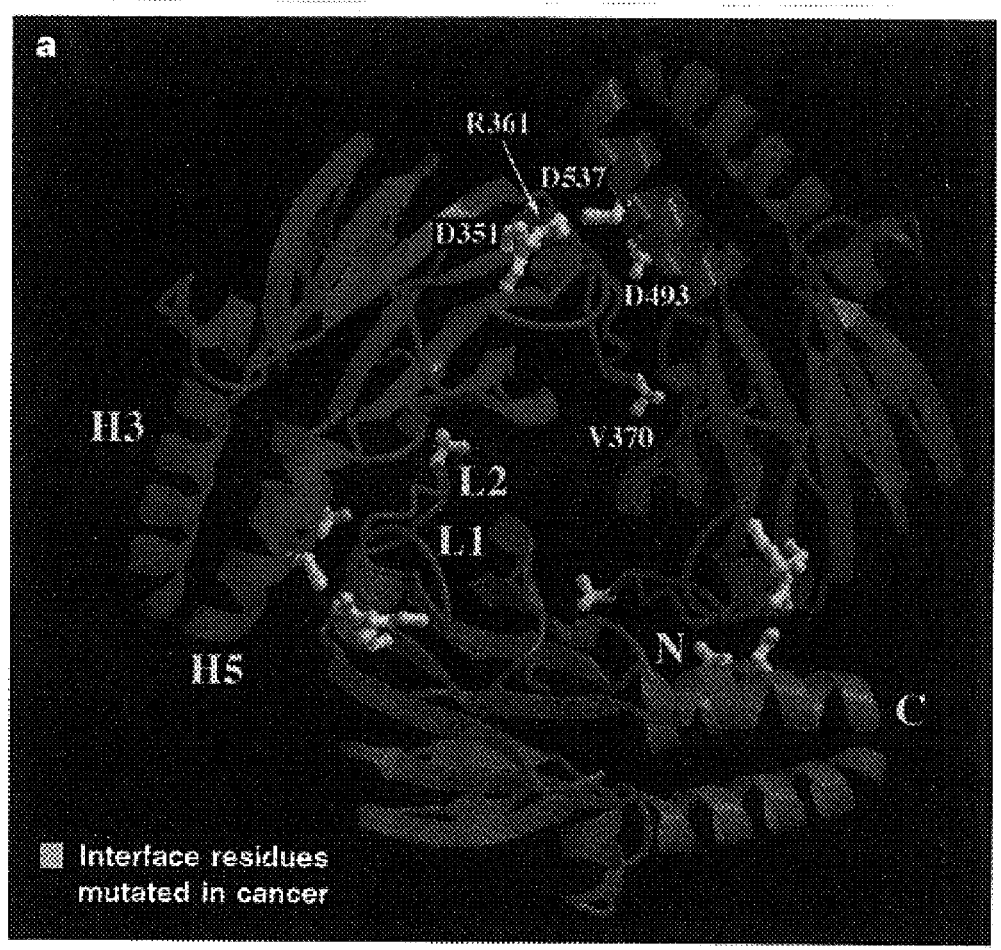
FIG. 3A shows the three monomers, colored red, blue, and magenta, pack across three identical protein-protein interfaces. Tumor-derived missense mutations map to five amino acids, shown in yellow, that are involved in inter-molecular contacts.

To further investigate the homo-oligomerization activity of the Smad4/DPC4-C-terminal domain, the packing of the Smad4/DPC4-C-terminal domain molecules in the crystals was examined and a crystallographic trimer that formed through three identical, extended protein-protein interfaces, burying a total of 4800 Å$^2$ of surface area was identified (FIG. 3A). Each interface forms through the interactions of the highly conserved regions of the Smad4/DPC4-C-terminal domain that contain the majority of the candidate functional residues: the loop/helix region of one subunit packs extensively with the three-helix bundle from another subunit, while making a few additional contacts to residues from the β-sandwich (FIG. 3A). The only portion of the loop/helix region that does not participate in this interface is the L3 loop.

Figure 3B:
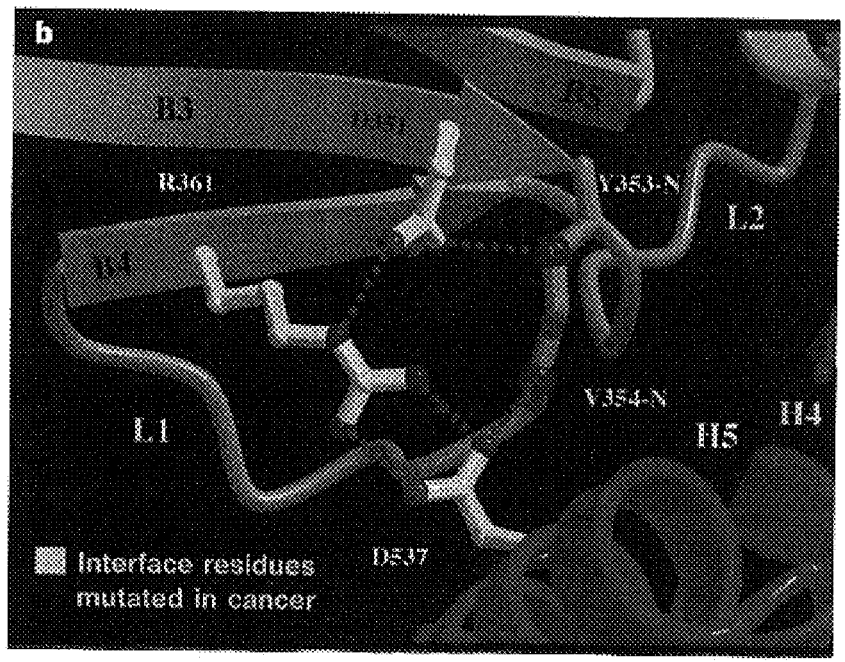
FIG. 3B shows a close-up view of a inter-molecular hydrogen bond network involving three residues all of which are mutated in cancer. Coloring is according to FIG. 3A.
Figure 3C:
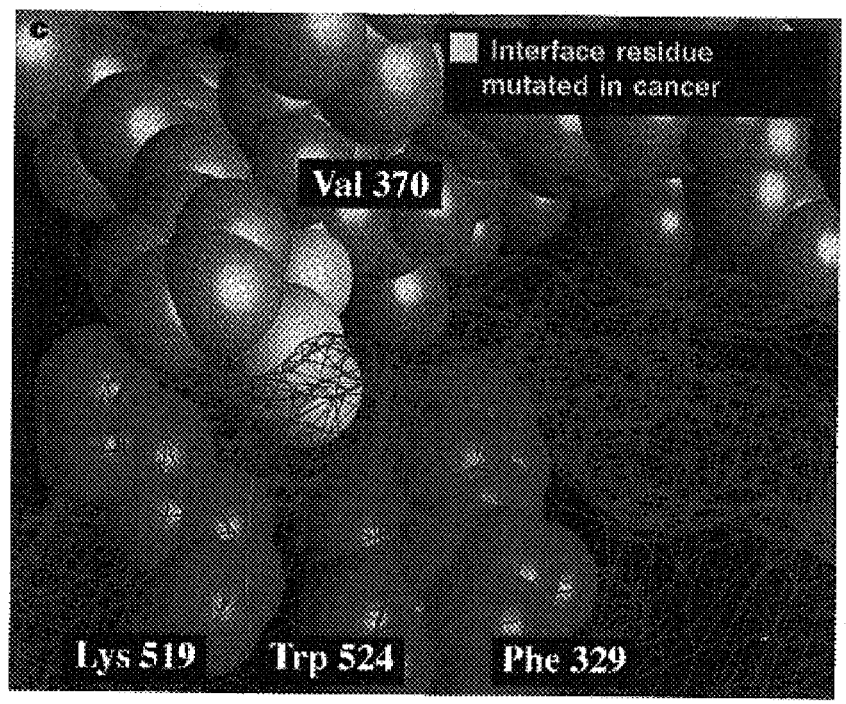
FIG. 3C shows a close-up view showing the intermolecular packing of Val370, which is mutated to Asp in cancer, against Phe329, Trp524, and the aliphatic portion of Lys519. The subunit in which Val370 is shown is in space-filling representation, whereas the other subunit is shown as the molecular surface (red mesh). Other intermolecular interactions not mentioned include: van der Waals contacts between the L1 loop of the loop/helix region and the H4 and H5 helices of the three-helix bundle (Tyr353, Val354, and Pro356 wedging in-between His530, Leu533, Leu536, Leu540, and His541); the hydrogen bond networks between Ser368 of the L2 loop and Arg496, Glu526, and His528 of the β-sheet, and between His371 of the L2 loop and Asp332 of the β-sheet. This figure was prepared with the program GRASP[29].

The trimer interface includes the majority of the conserved residues and the tumor-derived non-structural missense mutations (five out of six). Most noteworthy is an extended intermolecular hydrogen bond network involving, from one subunit, the Arg361 and Asp351 side chains and two backbone amide groups of the loop/helix region, and from another subunit, the Asp537 side chain of the three-helix bundle (FIG. 3B). The Asp351, Arg361, and Asp537 residues are essentially invariant, with the exception of a conservative Arg to Lys substitution in Sma-2 (FIGS. 2A–2B), and all three are mutated in cancer. The Asp351His and Arg361Cys mutations have been isolated from Smad4/DPC4 in ovarian[2] and colon cancer[17], respectively, and the Asp450Glu mutation, corresponding to Asp537 of Smad4/DPC4, has been isolated from Smad2 in colon cancer[12]. Each of these mutations is certain to disrupt this intricate hydrogen bond network at the interface. Also noteworthy are the intermolecular van der Waals contacts between Val370 on the L2 loop of the loop/helix and the Trp524, Phe329, and the aliphatic portion of the Lys519 side chain on the β-sheet at the base of the three-helix bundle (FIG. 3C).

The two aromatic residues are also essentially invariant, with the exception of a conservative Tyr to Phe substitution in Smad4/DPC4 (FIGS. 2A–2B). Furthermore, Val370 is found mutated to Asp in colon cancer[17]. The introduction of a charged amino acid into a hydrophobic portion of the interface should be effective in destabilizing the trimer interface. Finally, the Smad4/DPC4 Asp493His mutation from pancreatic cancer[1] also maps to the trimer interface (FIG. 3A) and would interfere with the electrostatic packing of Asp493 of one subunit with Arg496 and Arg497 of another subunit at the trimer interface. However, in the crystals, Asp493 is near the disordered region of the H4 helix and its interactions with the arginines are not well defined.

Many of the other trimer-interface contacts are also conserved in the Smad family (FIG. 3C), indicating that other Smad-C-terminal domains may form a similar trimeric structure. On the other hand, not all residues in the Smad4/DPC4-C-terminal domain trimer interface are conserved in all Smads, and it is likely that those that differ may contribute to subtype specificity. An example of this is an intermolecular hydrogen bond contact between His371 and Asp332. This pair is conserved in the *C. elegans* Smad4/DPC4 homologue, Sma4, whereas it is an invariant Asn-Asn pair in the pathway-restricted Smads (FIGS. 2A–2B).

Figure 3D:
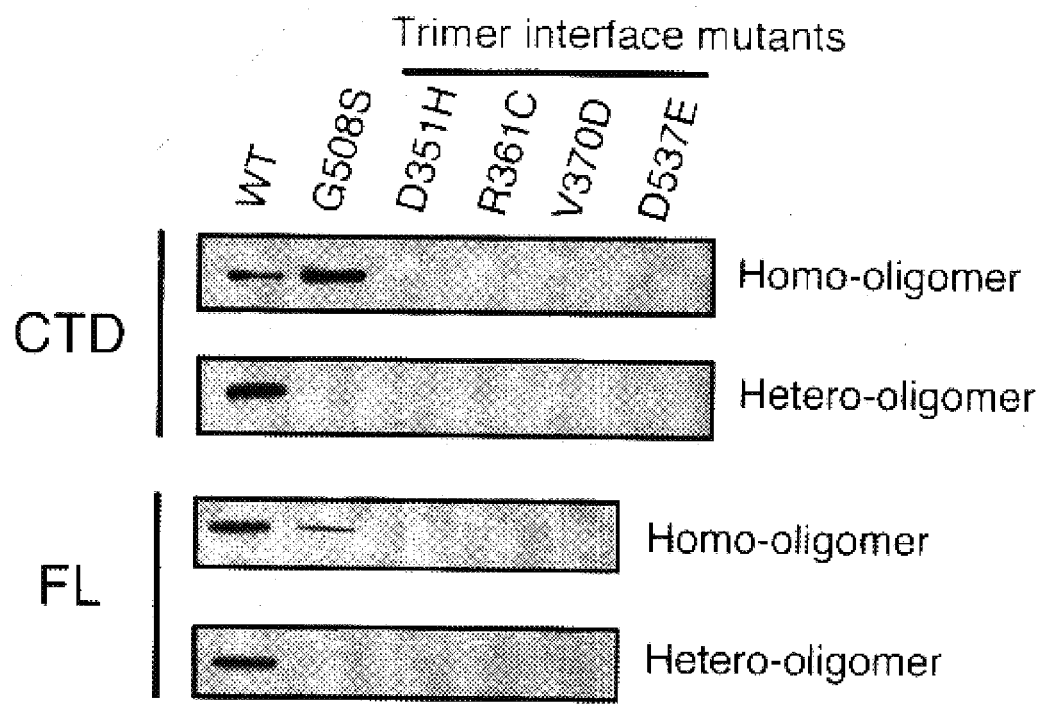
FIG. 3D shows that in vivo, tumor-derived trimer interface mutations disrupt both homo- and hetero-oligomerization, whereas a developmental mutation in the L3 loop disrupts only hetero-oligomerization. To assay for homo-oligomerization, mammalian COS-1 cells were transiently transfected with Flag-tagged wild-type Smad4/DPC4-C-terminal domain (WT) and HA-tagged WT or mutant constructs. For hetero-oligomerization, cells were transfected with Flag-tagged Smad2 C-terminal domain and HA-tagged Smad4/DPC4 C-terminal domain WT or mutant constructs together with constitutively active TGF-β type I receptor construct. The cell lysate was immunoprecipitated with anti-Flag antibody and subsequently immunoblotted using anti-HA antibody. Immunoblots indicated that the mutant Smad4/DPC4-C-terminal domains expressed at levels comparable to those of the wild type constructs. Studies with the full-length proteins were performed similarly.

If the trimeric Smad4/DPC4-C-terminal domain assembly observed in the crystals is part of the homo-oligomer observed in vivo, then mutations at residues that make intermolecular contacts at the interface, and in particular the tumor-derived mutations discussed earlier, should disrupt or reduce homo-oligomerization in vivo. FIG. 3D shows the results of co-immunoprecipitation experiments using extracts from COS cells transfected with differentially tagged mutant Smad4/DPC4 molecules. AU four of the tumorigenic mutations at residues that play important roles in the trimer interface, Asp351, Arg361, Val370, and Asp537, disrupted homo-oligomerization of the Smad4/DPC4-C-terminal domain. Similar results were obtained with the full-length Smad4/DPC4 (FIG. 3D). Conversely, the Drosophila/C. elegans developmental mutation Gly508Ser (FIG. 2B) had no effect on homo-oligomerization (FIG. 3D). This mutation maps to the L3 loop, which is the only portion of the loop/helix region not involved in the trimer interface.

Figure 4A:
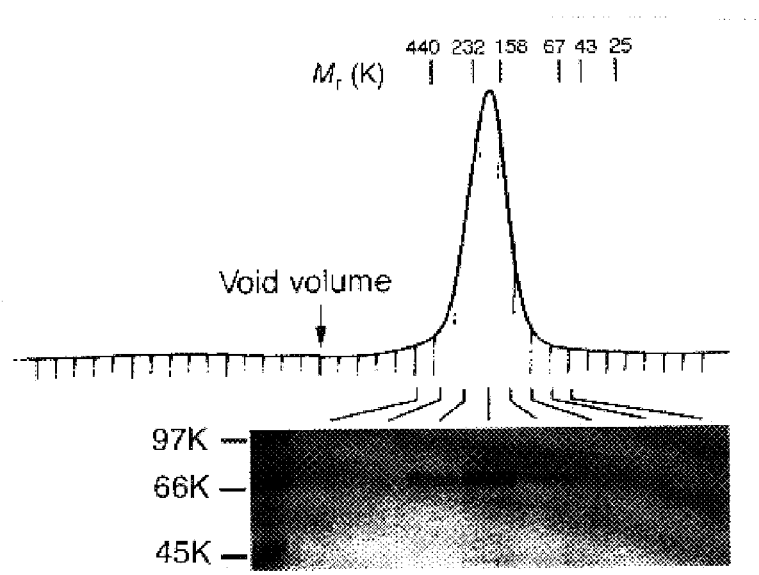
FIG. 4A shows that recombinant Smad4/DPC4 protein, purified to near homogeneity, was applied to a Superdex200 gel filtration column where it eluted as an approximately 180 kDa molecule. The fractions were visualized with Coomassie staining.
Figure 4B:
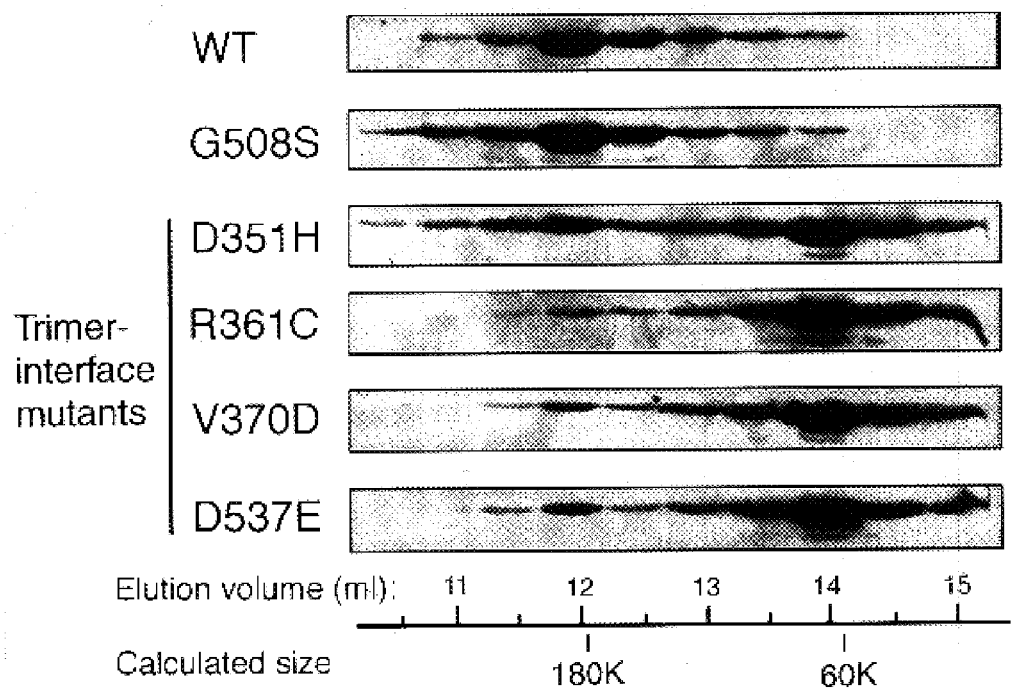
FIG. 4B shows that in vitro, tumor-derived trimer interface mutations disrupt homo-oligomerization, whereas a developmental mutation in the L3 loop has no apparent effect on the homo-oligomerization. Gel filtration fractions of partially purified wild-type and mutant Smad4/DPC4 proteins were analyzed by immunoblots with anti-Smad4/DPC4 antibody.

If the Smad4/DPC4-C-terminal domain forms a trimer, then full-length Smad4/DPC4 should form a trimer as well. FIG. 4A shows that recombinant full-length Smad4/DPC4, purified to near homogeneity, elutes from a gel-filtration column with an apparent molecular size of ~180 kDa, consistent with the 181 kDa size calculated for the Smad4/DPC4 trimer. This large apparent size is likely the result of trimerization because the tumor-derived trimer-interface mutations reduce the apparent size by a factor of about three (FIG. 4B). Conversely, the Drosophila/C. elegans developmental mutation Gly508Ser, which does not directly affect a trimer-interface residue, had no effect on the large apparent size of Smad4/DPC4 (FIG. 4B). However, the Smad4/DPC4-C-terminal domain elutes as a monomer from a gel filtration column, consistent with residues N-terminal to the Smad4/DPC4-C-terminal domain contributing to homo-oligomerization.

In principle, the full-length Smad4/DPC4 protein may assume an oligomeric state other than a trimer but still with a gel filtration mobility approximating that of a trimer. However, the in vivo and in vitro data with the trimer interface mutants, both with the C-terminal domain and the full-length proteins, strongly suggest that the trimeric protein-protein interface observed in the crystals is also the one that participates in homo-oligomerization in vivo.

The Smad4/DPC4-C-terminal domain also supports hetero-oligomerization, shown by the co-immunoprecipitation of overexpressed Smad4/DPC4-C-terminal domain and Smad2-C-terminal domain from COS cells (FIG. 3D), and by the association of Smad4/DPC4-C-terminal domain with Smad2-C-terminal domain in a native gel electrophoresis assay. Furthermore, the tumor-derived trimer interface mutations, as well as the developmental L3 loop mutation abolished hetero-oligomerization between the Smad4/DPC4-C-terminal domain and the Smad2-C-terminal domain (FIG. 3D). Similar results were obtained with the full-length Smad4/DPC4. The observation that the L3-loop developmental mutation, which did not significantly affect homo-oligomerization, disrupted hetero-oligomer formation, suggests that the L3 loop may participate in hetero-oligomerization. The observation that mutations that disrupted homo-oligomerization also disrupted hetero-oligomerization further suggest that homo-oligomer formation could be a prerequisite for hetero-oligomerization.

Figure 5A:
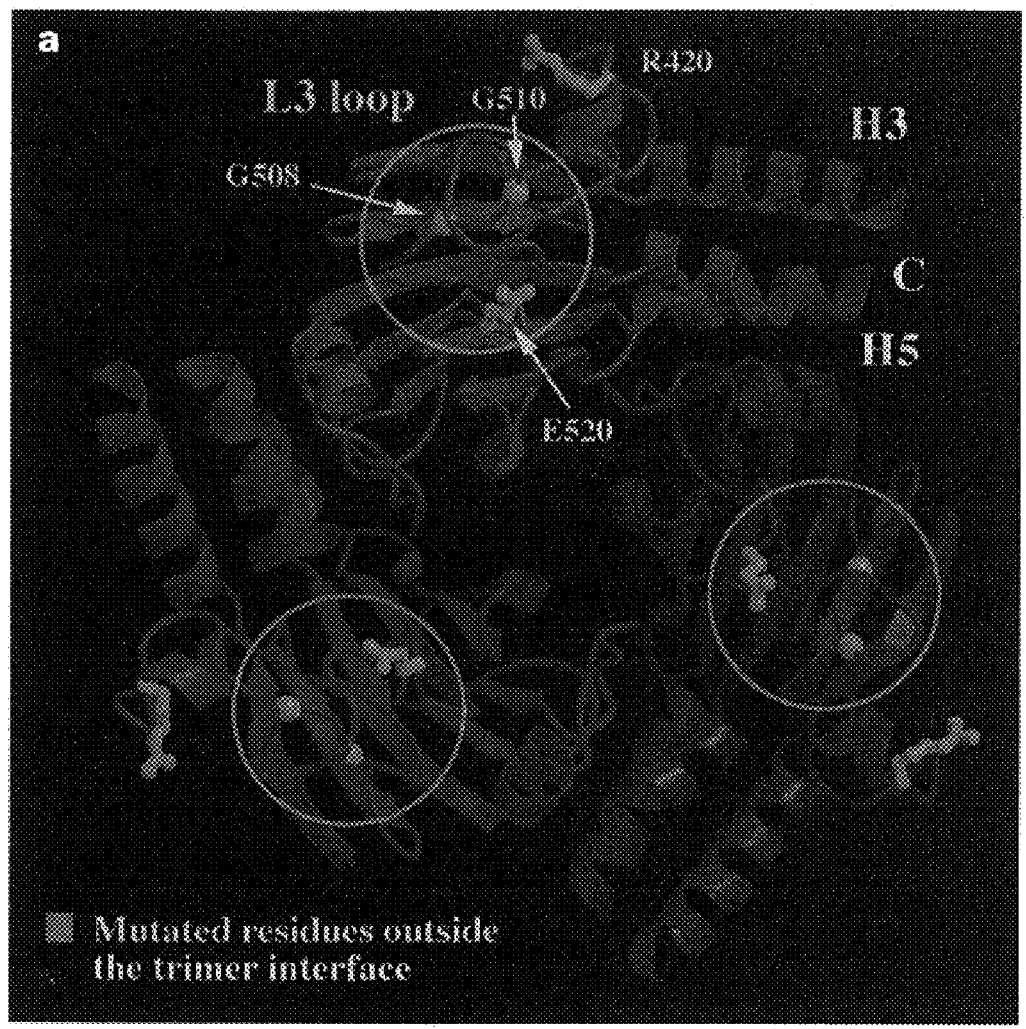
FIG. 5A shows that mutations outside the trimer interface map primarily to L3 loop residues, with the exception of Arg420, which is outside the L3 loop. The face of the trimer shown is opposite to that shown in FIG. 3A.
Figure 5B:
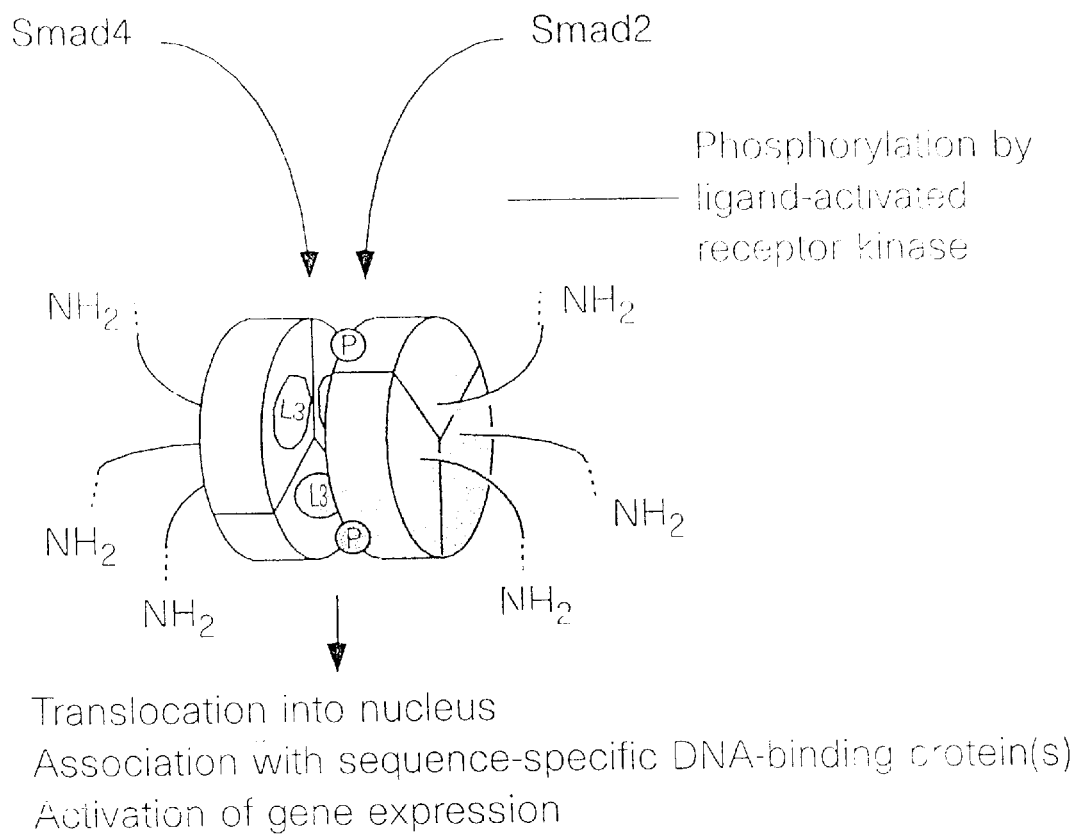
FIG. 5B shows that a model of hetero-oligomer formation depicting the Smad4/DPC4 and Smad2 C-terminal domain trimers as disks. The approximate positions of the Smad4/DPC4 L3 loops and of the Smad2 sites that get phosphorylated by the receptor kinase[30] are indicated by yellow and green, respectively.

Although several hetero-oligomerization models would be consistent with the available data, one model that is suitable, from a structural perspective, is the formation of a hetero-hexamer between Smad4/DPC4 and Smad2 trimers. As the trimer structure resembles a disk with the L3 loops forming undulations on the face of the disk (FIG. 5A), this could allow two disks to come together face-to-face and interact via their L3 loops (FIG. 5B), explaining why L3 loop mutations disrupt hetero-oligomerization. In this model, hetero-hexamer formation would also require homo-trimer formation, explaining how the tumorigenic mutations that disrupt homo-oligomerization can also disrupt the formation of the functional hetero-oligomeric complex and interfere with signal transduction.

EXAMPLE 7

Construction of Expression Vectors and Yeast Two-hybrid System

To generate human Smad4 and Smad2 mutations, a fragment of the corresponding cDNAs was amplified by PCR. The amplified region was subcloned into the full-length Smad4 or Smad2 in pCMV5 for mammalian cell transfection. The regions amplified by PCR and the presence of missence mutations were confirmed by sequencing.

LexA fusions were created in pBTM 116 and GAD fusions within pGAD424 (Clontech). Interactions were tested in the strain L40. Activation of the LexA operator-HIS3 reporter was assayed on media lacking histidine with increasing concentrations of 3-amino-triazole.

EXAMPLE 8

Transfection, Immunoprecipitation, Immunoblot, and Metabolic Labeling

For Smad2/Smad4 homo- or hetero-complex analysis, COS cell were transiently transfected with the indicated constructs, and stimulated with 200 pM TGFβ1 for 1 hour. Cells were lysed in TNE buffer, immunoprecipitated with anti-Flag M2 monoclonal antibody (IBI; Eastman Kodak), and interacting proteins were detected by immunoblot with anti-HA monoclonal antibody 12CA5 (Boehringer Manheim) as described. Anti-Smad rabbit polyclonal antibody was raised against the full-length Smad1. To study interactions between N domain and C domain of Smad4 or Smad2, transiently transfected COS cells were lysed in LSLD buffer (50 mM Hepes, pH 7.4, 50 mM NaCl, 0.1% Tween 20, 10% glycerol, 1 mM DTT) containing protease and phosphatase inhibitors. Immuno-precipitation and immunoblot were done as described above. COS or R-1B/L17 cells transfected with the indicated constructs were labeled with $^{35}$S-methionine or $^{32}$P-orthophosphate and visualized by electrophoresis and autoradiography.

EXAMPLE 9

Functional Assays

For the animal cap assay, RNA (10 nl, 2 ng) was introduced in the animal pole of two-cell Xenopus embryos. Animal caps were explanted at blastula stage and cultured to tadpole stage. Total RNA from the harvested explants and control sibling embryos was extracted and RT-PCR was performed using muscle actin and EFla primers. In the MDA-MB468 cell experiments, the amounts of transfected plasmids were adjusted in order to render the TGFβ response dependent on both Smad2 and Smad4. Luciferase and growth-inhibition assays were performed.

Figure 6A:
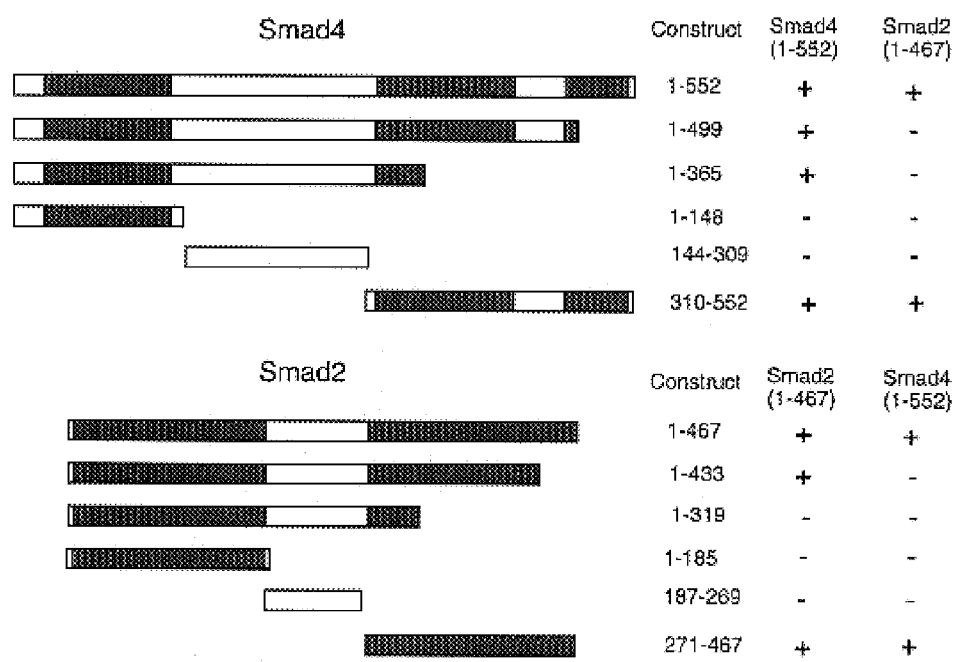
FIG. 6A shows the Smad4 and Smad2 interactions with themselves and each other in a yeast two-hybrid system. GAD fusions with the indicated portions of Smad4 or Smad2 were tested for interaction with full length or C domains of Smad2 or Smad4 fused to the LexA DNA binding domain. The relative strength of the interaction is indicated.
Figure 6B:
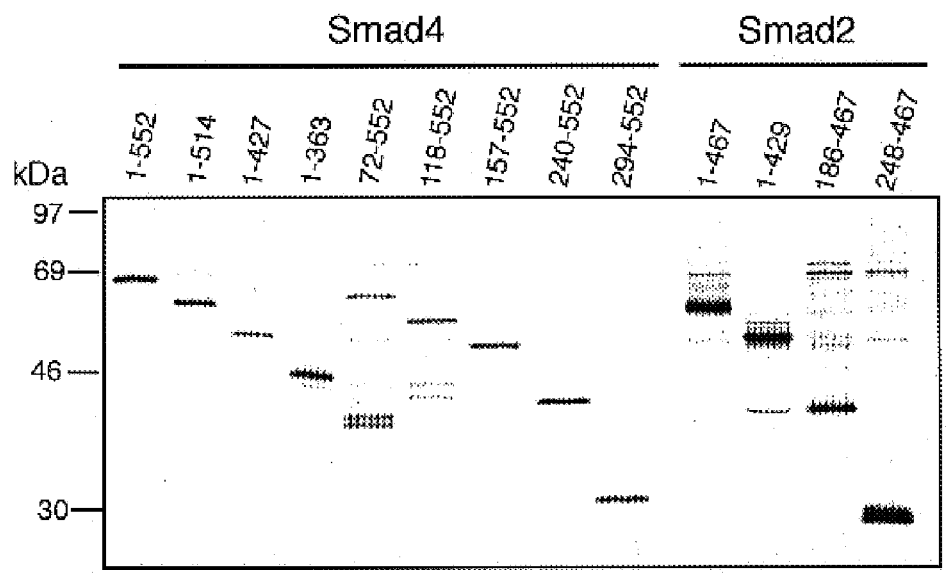
FIG. 6B shows expression level of HA-tagged Smad4 constructs and Flag-tagged Smad2 constructs was determined by epitope-tag immunoprecipitation from $^{35}$S-methionine labeled cells.
Figure 6C:
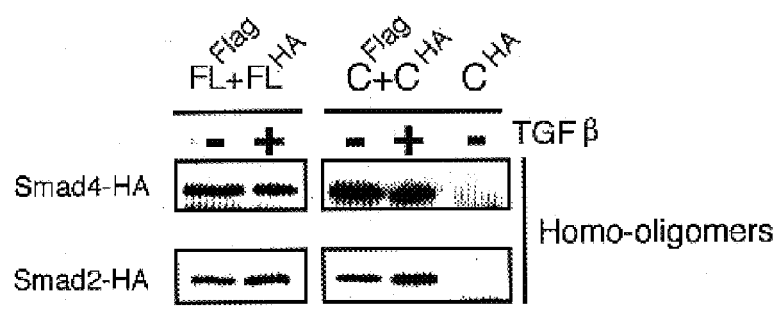
FIG. 6C shows homo-oligomerization of Smad4 or Smad2 C domains. COS cells were transiently transfected with full-length (FL) Smad4 or Smad2 or their C domains (C) (Smad4 amino acids 294–552; Smad2 amino acids 248–467). Versions of the same protein tagged N-terminally with the Flag epitope or C-terminally with the HA epitope were cotransfected. Some cultures were incubated with TGF-β for 1 hour before lysis. Homo-oligomerization was analyzed by anti-HA immunoblotting of anti-Flag immunoprecipitates.
Figure 6D:
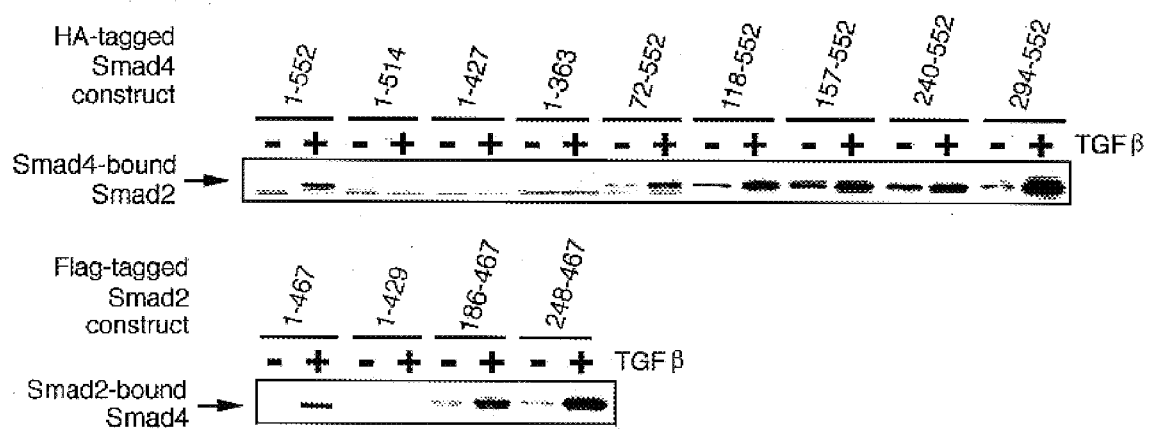
FIG. 6D shows hetero-oligomerization of Smad4 and Smad2 deletion constructs. HA-tagged Smad4 deletion constructs were co-transfected with Flag-tagged Smad2, and Flag-tagged Smad2 deletion constructs were cotransfected with full-length HA-tagged Smad4. TGF-β stimulation (+lanes) was provided by cotransfection of a constitutively active TGF-β type-I receptor and, additionally, incubation with TGF-β. Smad2-Smad4 interactions were analyzed by anti-Flag immunoblotting of anti-HA immunoprecipitates (top panel) or anti-HA immunoblotting of anti-Flag immunoprecipitates (bottom panel).
Figure 6E:
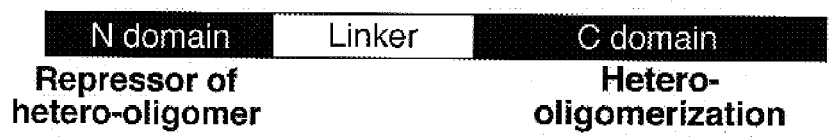
FIG. 6E shows summary of Smad domain contributions to Smad2-Smad4 hetero-oligomerization.
Figure 7A:
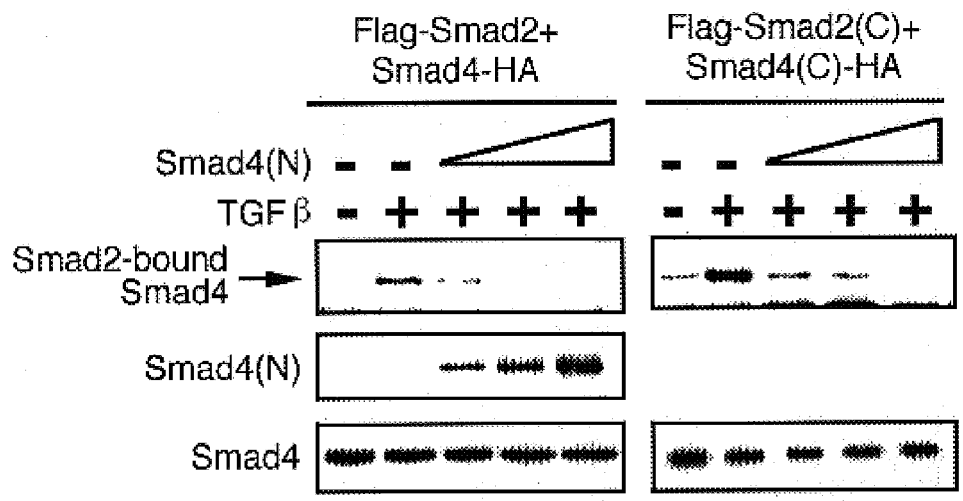
FIG. 7A and FIG. 7B show the inhibition of Smad2-Smad4 interaction by N domains. Increasing amounts (1, 2 and 4 mg) of plasmid encoding the Smad4 N domain (amino acids 1–154 of SEQ ID No. 1) or the Smad2 N domain (amino acids 1–185 of SEQ ID No. 3) tagged with the indicated epitopes were cotransfected with the indicated full length or C domain forms of Smad4 and Smad2 into COS cells. Smad2-Smad4 association was determined by anti-Flag immunoprecipitation followed by anti-HA immunoblotting. N domain and Smad4 expression levels were monitored by immunoblotting with specific antibodies.
Figure 7B:
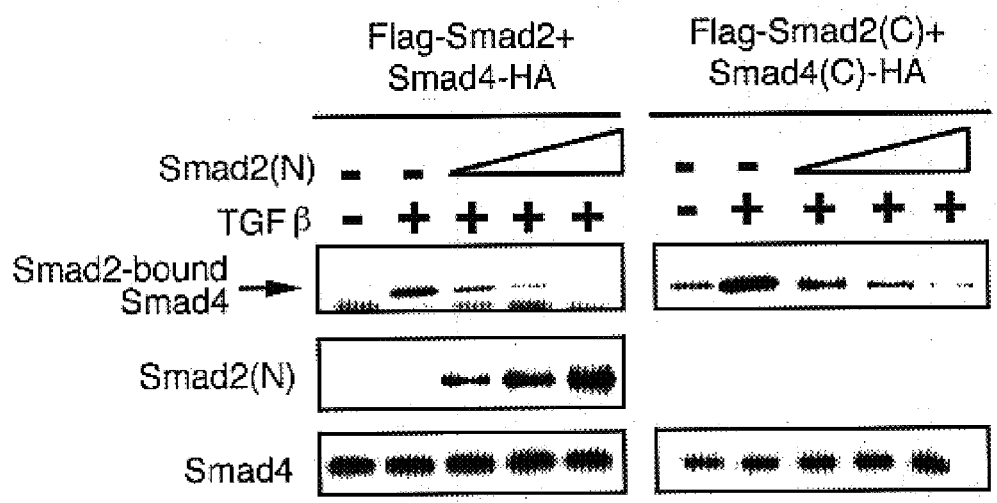
Figure 7C:
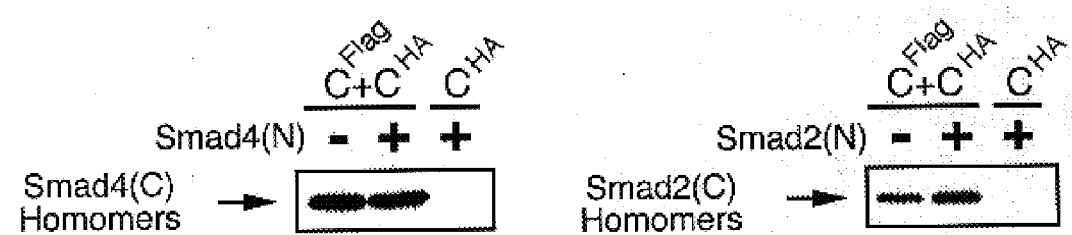
FIG. 7C shows that N domain expression does not affect C domain homo-oligomerization. Flag-tagged and HA-tagged versions of Smad C domains were co-transfected with the indicated N domain. The levels of Smad4 (FIG. 7C) (top panel) or Smad2 (FIG. 7C) (bottom panel) homo-oligomers were determined by anti-HA immunoblotting of anti-Flag immunoprecipitates.
Figure 7D:
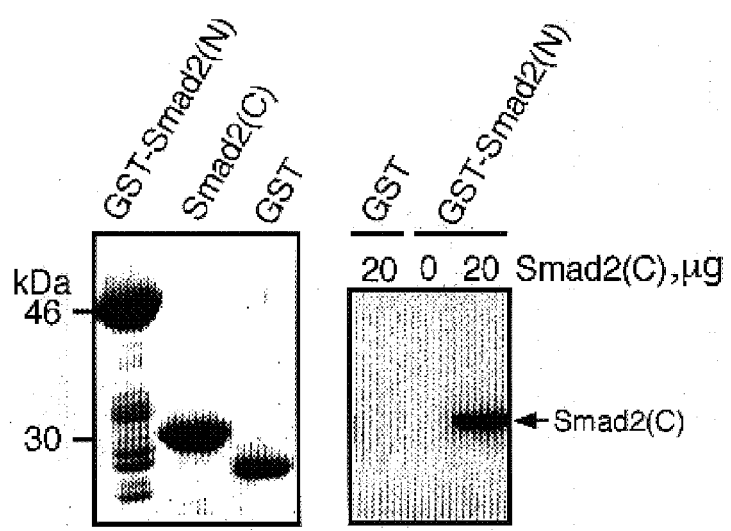
Figure 8A:
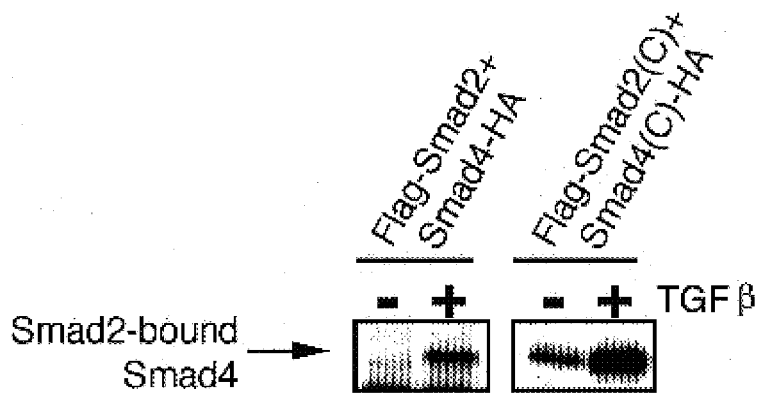
FIG. 8A shows constitutive association of the isolated C domains of Smad4 and Smad2, and further stimulation by TGF-β. Flag-tagged full-length or C domain Smad2 constructs and HA-tagged full-length or C domain Smad4 constructs were cotransfected into COS cells. Cultures were stimulated with TGF-β as indicated. Smad2-Smad4 interactions were analyzed by anti-HA immunoblotting of anti-Flag immunoprecipitates.
Figure 8B:
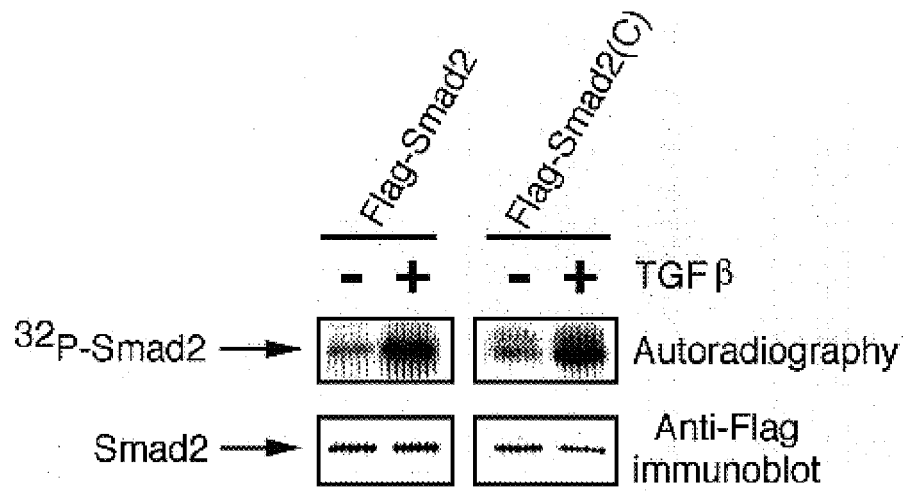
FIG. 8B shows Smad2 C domain phosphorylation in response to TGF-β. Constructs were transiently co-transfected with TβR-I into R-1B/L17 cells. Transfectants were labeled with $^{32}$P-orthophosphate, and stimulated with TGF-β for 20 minutes as indicated. Smad2 was immunoprecipitated with anti-Flag antibody and subjected to autoradiography (top panel). Quantitation revealed an 8-fold increase in phosphorylation of Smad2 or Smad2(C) in response to TGF-β. Aliquots of cell lysate were subjected to anti-Flag immunoblotting to control for Smad2 levels (bottom panel).
Figure 8C:
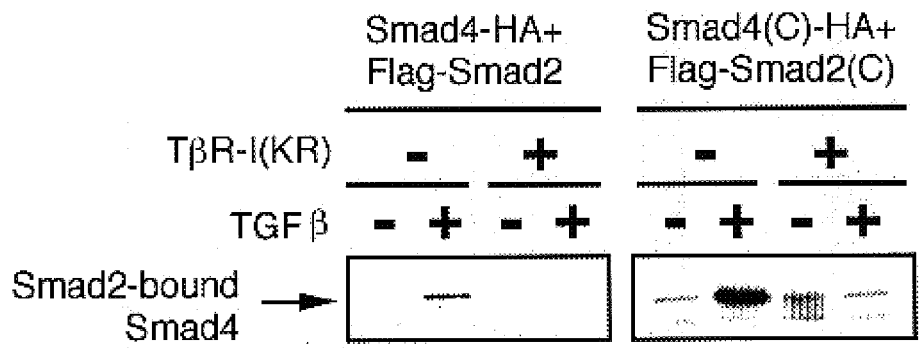
FIG. 8C shows the constitutive interaction of Smad4 and Smad2 C domains is independent of TGF-β receptor-mediated phosphorylation. Smad2-Smad4 (full-length or C domain) complex formation was analyzed in the presence or absence of a cotransfected dominant negative TβR-I construct [TβR-I(KR)]. Other conditions were as described in FIG. 8A.
Figure 9A:
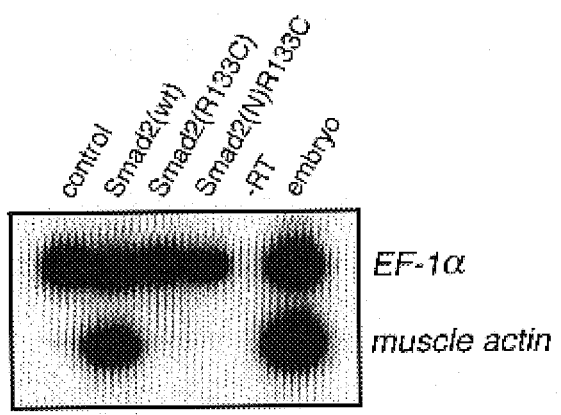
FIG. 9A shows that wild type Smad2 induces the paraxial mesoderm marker muscle actin in Xenopus ectodermal explants, whereas Smad2 (R133C) or its N domain alone [Smad2(N) R133C] are unable to induce it. EF-1a was used as an internal control.
Figure 9B:
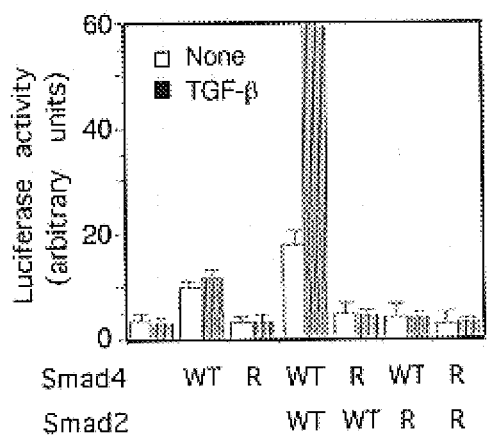
FIG. 9B shows cotransfection of wild type Smad2 and Smad4 (WT) restores TGF-β responsiveness into Smad4-defective MDA-MB468 breast cancer cells, whereas co-transfections including the Smad2(R133C) mutant (R), the Smad4(R100T) mutant (R) or both mutants do not. The TGF-β responsiveness of these cells was determined using the reporter construct 3TP-lux.
Figure 9C:
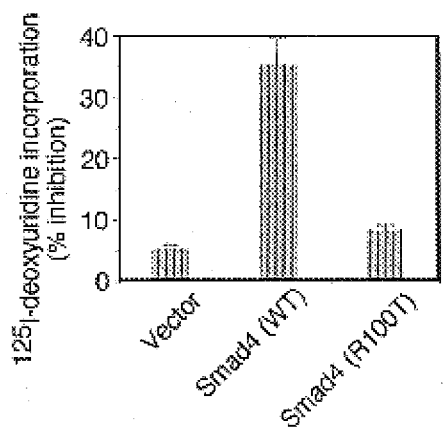
FIG. 9C shows that overexpression of wild type Smad4 inhibits MDA-MB468 cell proliferation whereas overexpression of the Smad4(R100C) mutant does not. The proliferative activity of the cells was determined by measuring iododeoxyuridine incorporation into DNA. Results are the average±S.D. of triplicate assays.
Figure 10A:
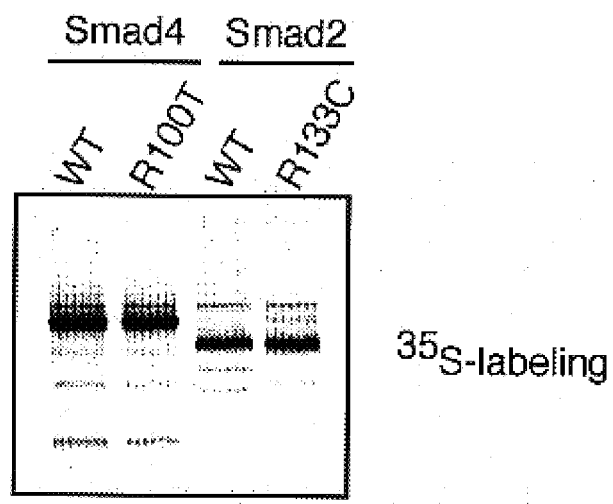
FIG. 10A shows that N domain mutations inhibit the Smad2-Smad4 interaction. Expression levels of wild type and mutant Smads were determined by epitope-tag immunoprecipitation from $^{35}$S-methionine labeled, transfected COS cells. HA-tagged wild type (WT) or mutant Smad4 was cotransfected with Flag-tagged Smad4 (for homo-oligomeric interaction) or Flag-tagged Smad2 (for hetero-oligomeric interaction) in COS cells. Likewise, Flag-tagged wild type (WT) or mutant (R133C) Smad2 was cotransfected with HA-tagged Smad2 or HA-tagged Smad4. The indicated cells were stimulated with TGF-β. Homo-oligomerization or hetero-oligomerization was then determined.
Figure 10B:
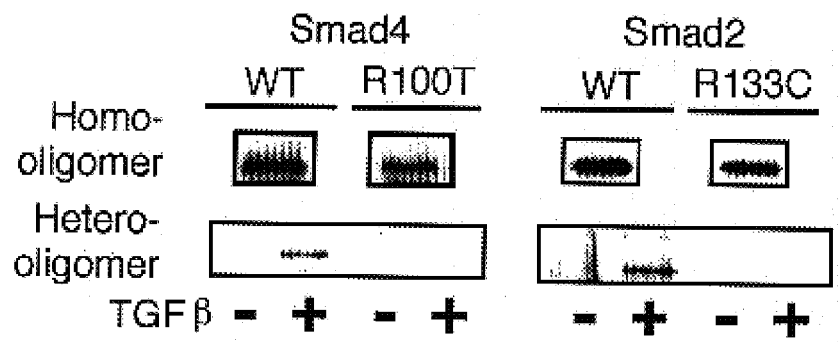
FIG. 10B shows the N domain interaction with the C domain, and its increase by mutations. Flag-tagged N domains indicated at the top were cotransfected with the HA-tagged C domains indicated at the bottom. N domain-C domain interaction was determined by anti-HA immunoblotting of anti-Flag immunoprecipitates. N domain expression levels were monitored by immunoprecipitation from $^{35}$-S methionine labeled cells.
Figure 10C:
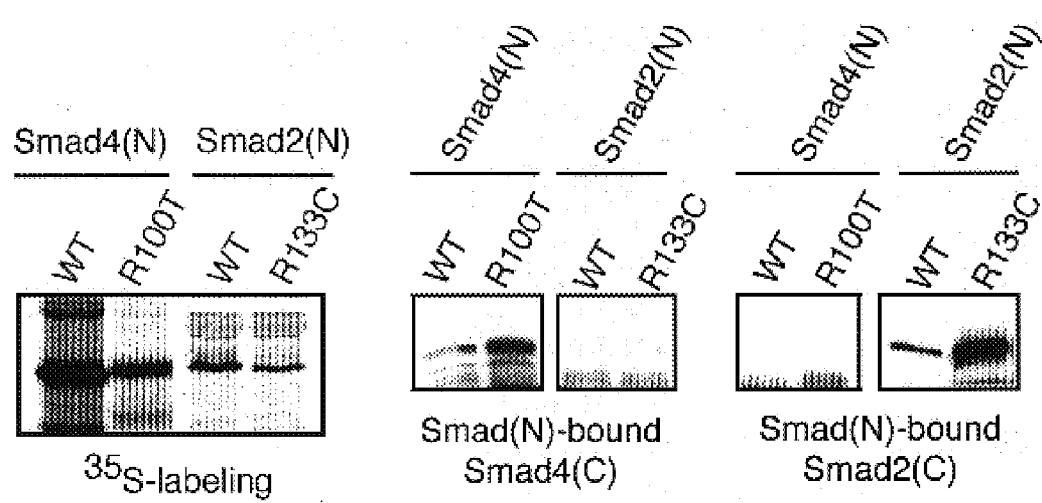
FIG. 10C shows that mutant N domains inhibit the Smad2-Smad4 interaction strongly. Increasing amounts of plasmid DNA encoding wild type (WT) or mutant (R100T) Smad4 N domain (left panel) or wild type (WT) or mutant (R133C) Smad2 N domain (right panel) were cotransfected with Flag-tagged Smad2 C domain and HA-tagged Smad4 C domain. The level of Smad2(C)-Smad4(C) complex was then determined by anti-HA immunoblotting of anti-Flag immunoprecipitates. The relative levels of Smad4 N domain expressed in these cells were determined by immunoblotting using anti-Smad polyclonal antibody. The levels of Smad4 or Smad2 N domain protein and Smad2(C)-bound Smad4 (C) were quantitated (ImageQuant; Molecular Dynamics) and plotted against each other.
Figure 10D:
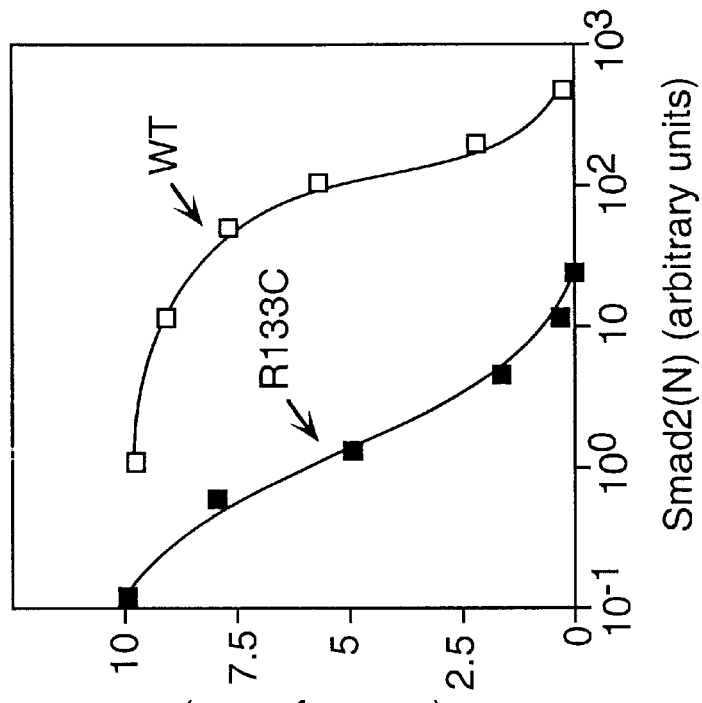
FIG. 10D shows the N domain inhibition of Smad2-Smad4 signaling function, and its increase by N domain mutations. R-1B/L17 cells were transiently transfected with the indicated constructs and 3TP-lux reporter.
Figure 10D:
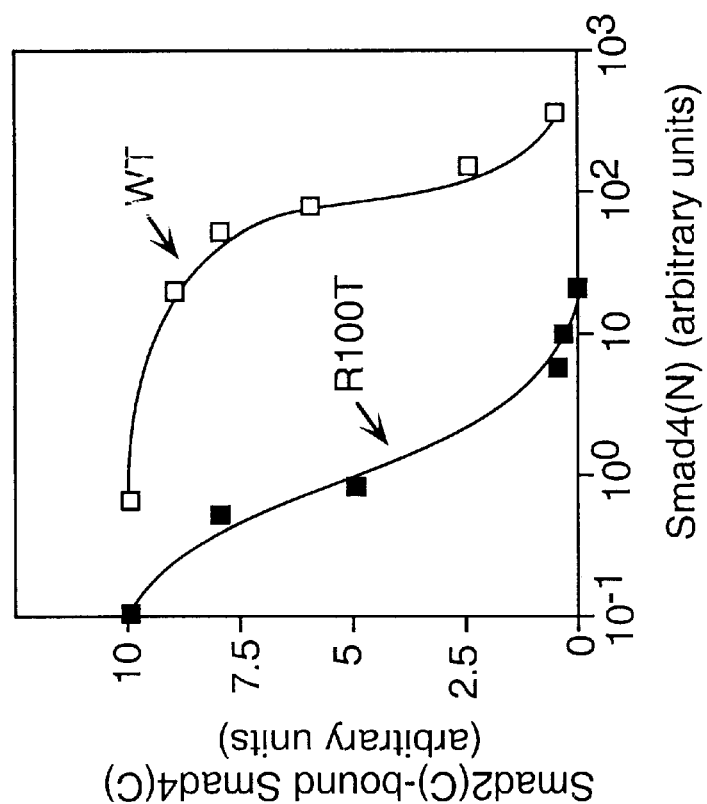
Figure 10E:
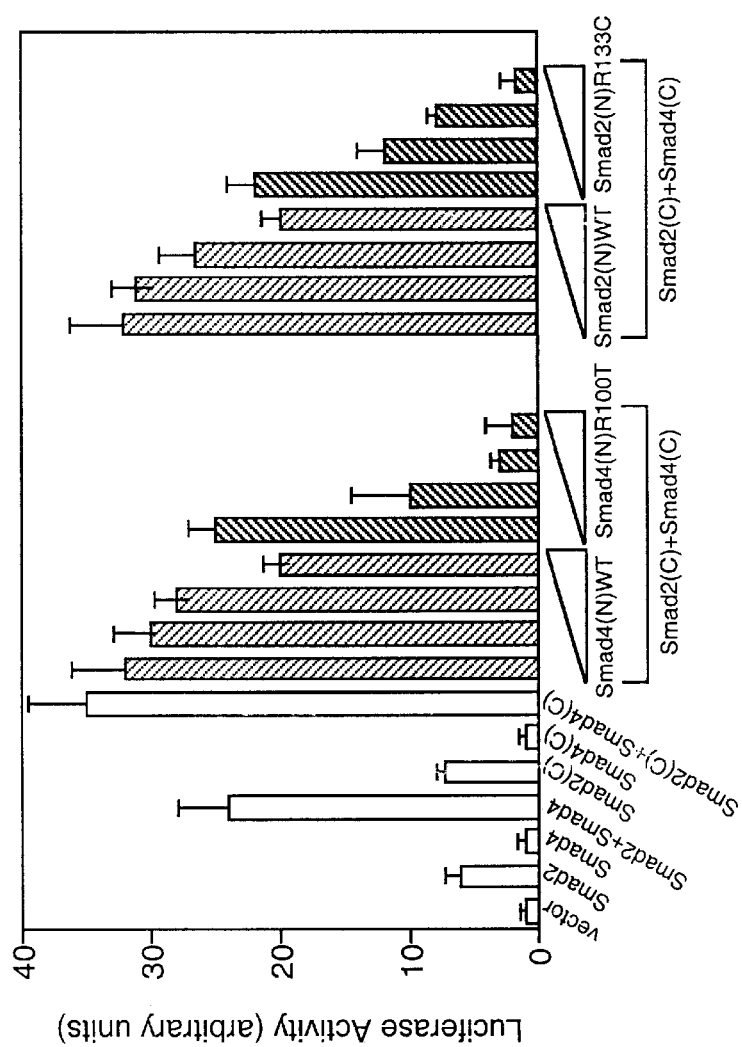
FIG. 10E shows luciferase activity in arbitrary units. Amounts of transfected Smad4 and Smad2 were adjusted so that they would increase luciferase expression synergistically. Increasing amounts (1, 2, 4, and 6 mg) of plasmid DNA encoding wild type or mutant N domains were cotransfected with the Smad4(C)/Smad2(C) combination. Results (luciferase activity in arbitrary units) are the average±S.D. of triplicate assays.

Various Smad4 fragments were tested as baits either against Smad4, to detect homo-oligomeric interactions, or against Smad2, to detect hetero-oligomeric interactions, in a yeast two-hybrid system. These experiments revealed that both the C domain and the N domain/linker region can contribute to the homo-oligomeric interaction (FIG. 6A). Full length Smad4 interacted with the N domain/linker region as a whole but not with these two regions when separately expressed (FIG. 6A). Full length Smad4 interacted with its isolated C domain, albeit less strongly than with itself (FIG. 6A). Furthermore, isolated Smad4 C domain interacted strongly with itself (FIG. 6A).

The higher affinity of full length Smad4 for itself than for its isolated C domain would result in the exclusion of the isolated C domain from full length homo-oligomeric complexes. Smad2 had a similar, albeit not identical pattern of homo-oligomeric interactions in yeast (FIG. 6A). The homo-oligomeric interaction pattern of the Smads in yeast is consistent with a contribution of all three regions to the homo-oligomeric interaction, with the C domain providing the strongest interaction. Resolution of the crystal structure of the Smad4 C domain has revealed that this domain forms a homotrimer whose interfaces are the targets of cancer mutations. The Smad2-Smad4 interaction was detectable in yeast, and was particularly sensitive to deletions in the C domain (FIG. 6A).

The Smad2-Smad4 interaction was detectable in yeast, and was particularly sensitive to deletions in the C domain (FIG. 6A).

EXAMPLE 10

Expression Vectors

Human Smad1, Smad2 and Smad4 mutations were made by a PCR-based strategy as described. All PCR-generated fragments were subcloned into wild type Smads in CMV promoter-based mammalian expression vectors pCMV5 or pCS2 and verified by sequencing.

The transfection, metabolic labeling and immunoprecipitation studies were performed as follows. For in vivo labeling with [$^{35}$S]methionine or [$^{32}$P]orthophosphate and for co-immunoprecipitation studies, cells were transiently transfected by the DEAE-dextran method as described above. To examine the phosphorylation of Flag-tagged Smad1 and Smad2 constructs, R-1B/L17 cells were co-transfected with either TβR-I or BMPR-IB and BMPR-II. Forty to 48 hours after transfection, cells were washed and preincubated with phosphate-free media for 1 hour. The cells were then incubated with the same phosphate-free media containing 1 mCi/ml [$^{32}$P]phosphate for 2 hours at 37° C. and then stimulated with either TGF-β1 (1 nM) or BMP4 (10 nM) for 30 minutes. Subsequently, labeled and ligand-stimulated cells were lysed in TNE buffer (10 nM Tris, pH 7.8; 150nM NaCl; 1 nM EDTA; 1% NP40) containing protease and phosphatase inhibitors, and the lysates were subjected to immunoprecipitation with anti-Flag M2 monoclonal antibody (IBI; Eastman Kodak). Protein expression of Smads was determined either by metabolic labeling or western blotting. COS-1 cells that have been transiently transfected for 40–48 hours were washed and preincubated in methionine-free media and then labeled with trans-[$^{35}$S] methionine for 3 hours. Lysis and immunoprecipitation were performed as for [$^{35}$P]phosphate-labeled cells. Immunoprecipitates were visualized by SDS-polyacrylamide gel electrophoresis (SDS-PAGE) followed by autoradiography. For western blotting, a fraction of the total cell lysate was separated by SDS-PAGE and assayed by immunoblotting as indicated.

For Smad4 association studies, Flag-tagged Smad1 or Smad2 constructs were transiently co-transfected with HA-tagged Smad4 into COS-1 cells. Forty to 48 hours after transfection, cells were washed in DMEM containing 0.2% fetal calf serum and treated with the indicated ligand (200 pM TGF-β1 or 5 nM BMP4). Following ligand-stimulation, cells were lysed in TNE buffer containing protease inhibitors. Cell lysates were then subjected to immunoprecipitation with anti-Flag M2 monoclonal antibody. Immunoprecipitates were washed, separated by SDS-PAGE, and transferred to PVDF membranes (Immobilon-P; Millipore). HA-tagged Smad4 was detected using anti-HA monoclonal antibody 12CA5 (Boehringer Mannheim), followed by donkey anti-mouse antibody conjugated with horseradish peroxidase (Sigma) and chemiluminescenc (ECL, Amersham).

COS-1 cells transiently transfected for 40–48 hours by the DEAE-dextran method were affinity-labeled with [$^{125}$I] TGF-β as described. Briefly, cells were preincubated at 37° C. in Krebs Ringer Hepes (KRH) buffer containing 0.5% bovine serum albumin (BSA), washed with cold KRH/0.5% BSA, and affinity labeled using 200 pM [$^{1125}$I]TGF-β in KRH/0.5% bovine serum albumin (BSA) for 3.5 hrs at 4° C. Then, the cells were washed four times in ice-cold KRH containing 0.5% BSA and once more with KRH alone. Subsequently, cell-surface bound [$^{125}$I]TGF-β was cross-linked to the receptor complex by incubation for 15 minutes at 4° C. with 60 mg/ml disuccinimidyl suberate in KRH; cross-linking was terminated by washing the cells twice with ice-cold STE (0.25 M sucrose, 10 mM Tris-HC1, pH 7.4 and 1 mM EDTA). Cells were then lysed in TNT [20 mM Tris-HC1, pH 7.4, 150 mM NaC1, 1% Triton X-100 (v/v)[$^{37}$ containing protease and phosphatase inhibitors and the cell lysate subjected to anti-Flag immunoprecipitation. Labeled receptor complexes in the immunoprecipitates and in the total cell lysates were then visualized by separation on SDS-PAGE and autoradiography.

HepG2 cells were transfected overnight using the calcium phosphate-DNA precipitation method. Twenty-four hours after transfection, cells were transferred onto chamber slides (Nunc, Inc.). Forty to 48 hours post-transfection, cells were stimulated with 5 nM BMP4 or 1 nM TGF-62 for 30 minutes and processed for immunofluorescence. Immunostaining was performed using anti-Flag M2 monoclonal antibody and FITC-conjugated secondary antibodies (Pierce).

The present invention shows that the L3 loop in the C domain of receptor-regulated Smads is crucial for their specific interaction with the TGF-β and BMP receptors. Signal transduction specificity in the TGF-β system was determined by ligand activation of a particular receptor complex which then recruits and phosphorylates a subset of Smad proteins including Smads 1 and 2. These then associate with Smad4 and move into the nucleus where they regulate transcription. A discrete surface structure was identified in Smads 1 and 2 that mediates and specifies their receptor interactions. This structure is the L3 loop, a 17-amino acid region that, according to the crystal-structure of Smad4, protrudes from the core of the conserved Smad C-terminal domain. The L3 loop sequence is invariant among TGF-β-activated Smads (Smads 2 and 3) and BMP-activated Smads (Smads 1, 5, 9 and Mad) but differs at two positions between these two groups. Switching these two amino acids switches Smad1 and Smad2 activation by BMP and TGF-β, respectively. This studies identify the L3 loop as a critical determinant of specific Smad-receptor interactions.

EXAMPLE 11

C-tail is dispensable for Smad2 association with the TGF-β receptor

Figure 11A:
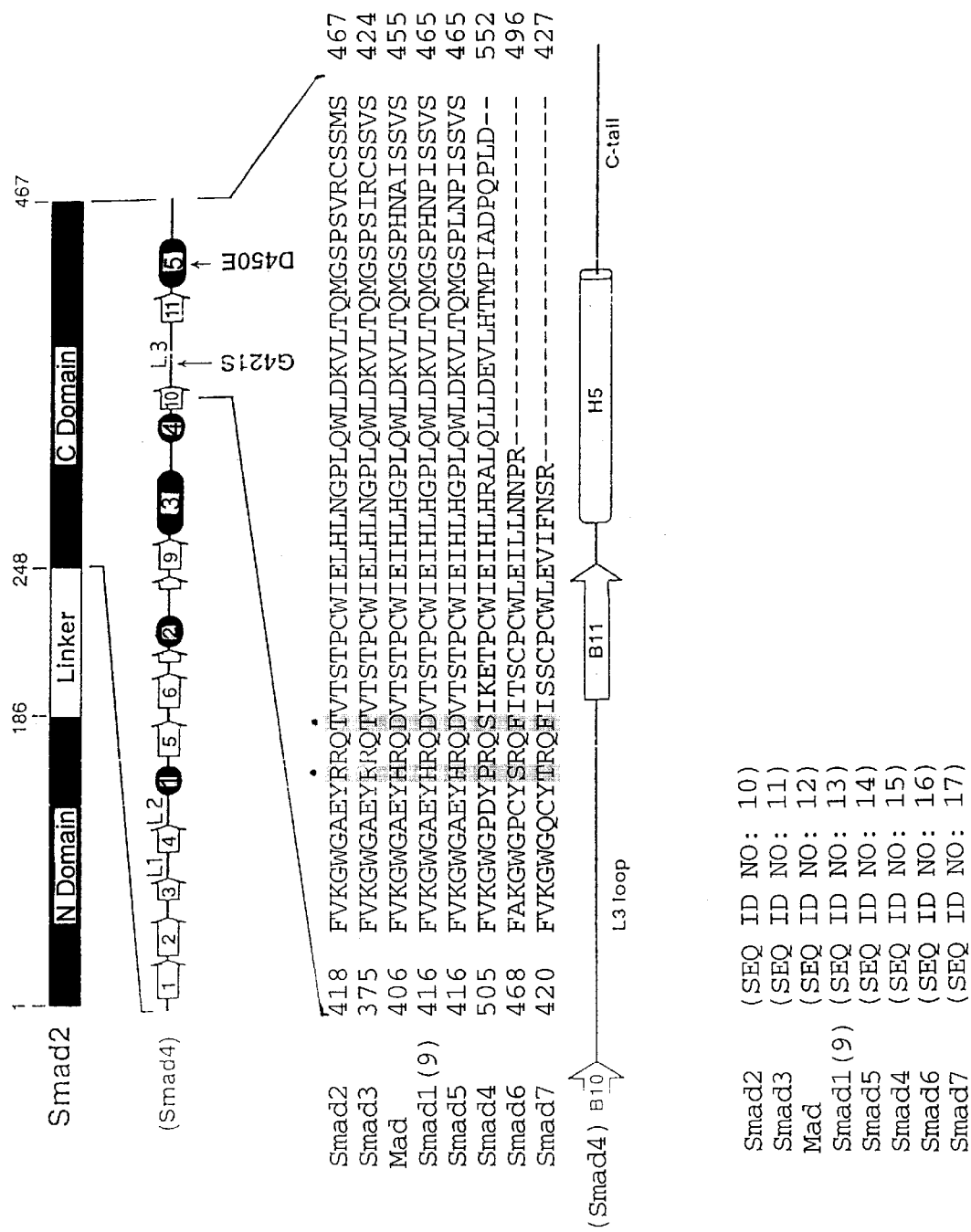
FIG. 11A shows a diagrammatic representation of Smad2, its C domain structure based on Smad4, and amino acid sequence alignment of the Smads starting from the L3 loop to the end. In the C domain structure, arrowheads (1 to 11) represent β-sheets; L1 to L3 represent loops; filled circles represent α-helices. In the amino acid sequence alignment, the conserved amino acids are boxed. The two residues in the L3 loop which are distinct among different Smad groups are highlighted.
Figure 12A:
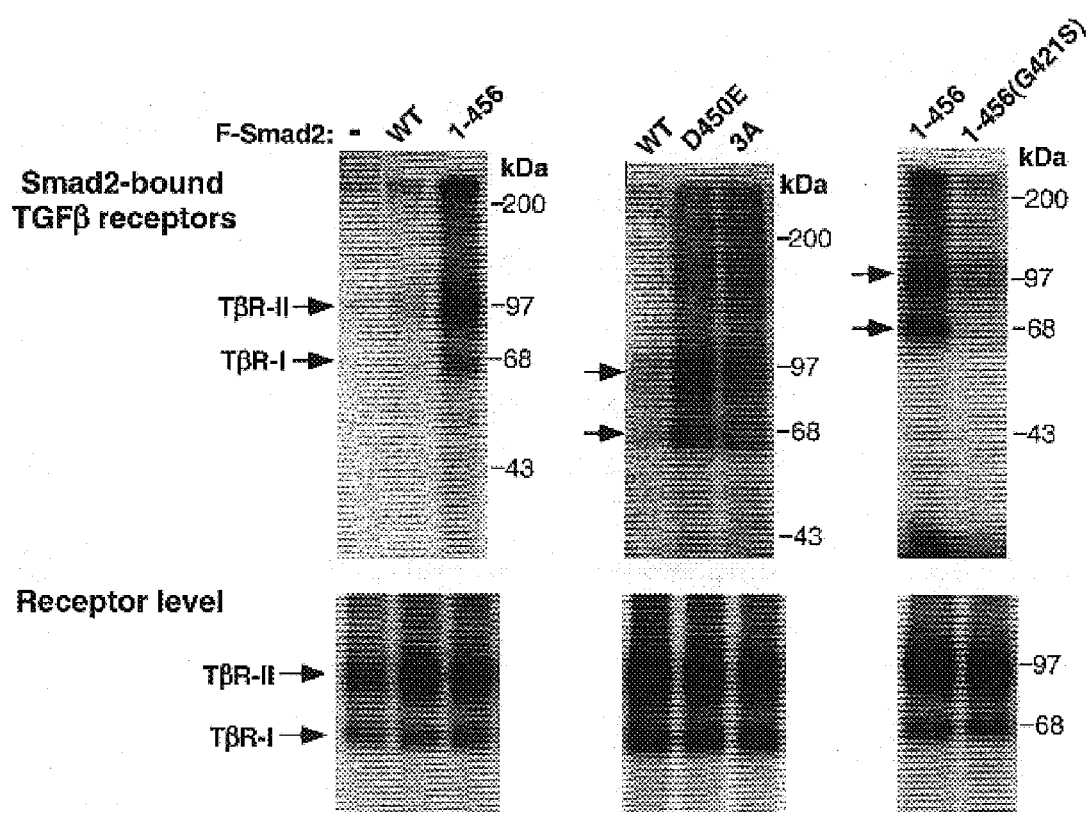
FIG. 12A: Smad2-TGF-β receptor interaction was determined by co-transfecting Flag-tagged wild type and mutant Smad2 with wild type TβR-I and TβR-II receptors into COS-1 cells, afffnity-labeling by cross-linking to [$^{125}$I]-TGF-β1, then co-immunoprecipitating Smad2-receptor complex using anti-Flag antibody. The immunoprecipitates and aliquots of whole cell lysates were subjected to SDS-PAGE and autoradiography to visualize the Smad2-bound receptors (upper panel) and the total receptor levels (lower panel), respectively.

Receptor-regulated Smads are phosphorylated by activated receptors at conserved C-terminal serine residues. According to the crystal structure of the Smad4 C-domain, thought to be conserved in the receptor-regulated Smads, these residues are located at the end of an 11-amino acid region (here referred to as the "C-tail") following α-helix 5 (FIG. 11A). As a substrate for the TGF-β type I receptor Kinase. the C-tail might mediate the observed docking of Smad2 to the receptor complex. The possibility was examined by testing the receptor-binding activity of a Smad2 construct lacking the C-tail (Smad2: amino acids 1–456 of SEQ ID No. 3). Receptor-binding activity was assayed by co-transfection of TβR-I, TβR-II and Flag epitope-tagged Smad2 constructs into cells, then affinity-labeling the receptors by crosslinking to bound $^{125}$I-TGF-β1, and finally co-immunoprecipitating the labeled receptors with Smad2 via the Flag epitope (FIG. 12A). Surprisingly, the receptor interaction was stronger with Smad2 (amino acids 1–456 of SEQ ID No. 3) than with wild type Smad2 (FIG. 12A), indicating that the removal of the C-tail increased the Smad2-receptor interaction. This suggests that the physical contact between the C-tail of Smad2 and the catalytic cleft of the TβR-I kinase during the phosphotransfer reaction does not contribute significantly to Smad-receptor association. Smad2 docking to the receptor must therefore be mediated by a region of Smad2 other than the C-tail. The interaction between the TGF-β receptor complex and Smad2 is increased when TβR-I is made catalytically inactive by a mutation in the kinase domain of the C-terminal phosphorylation sites in Smad2 are eliminated by mutation to alanine (see FIG. 12A, Smad2(3A) construct). In light of the observation that removal of the C-tail increases the receptor interaction, these results suggest that docking is inhibited when the C-tail is phosphorylated.

EXAMPLE 12
The Smad2 C domain associates with the receptor complex

Figure 13:
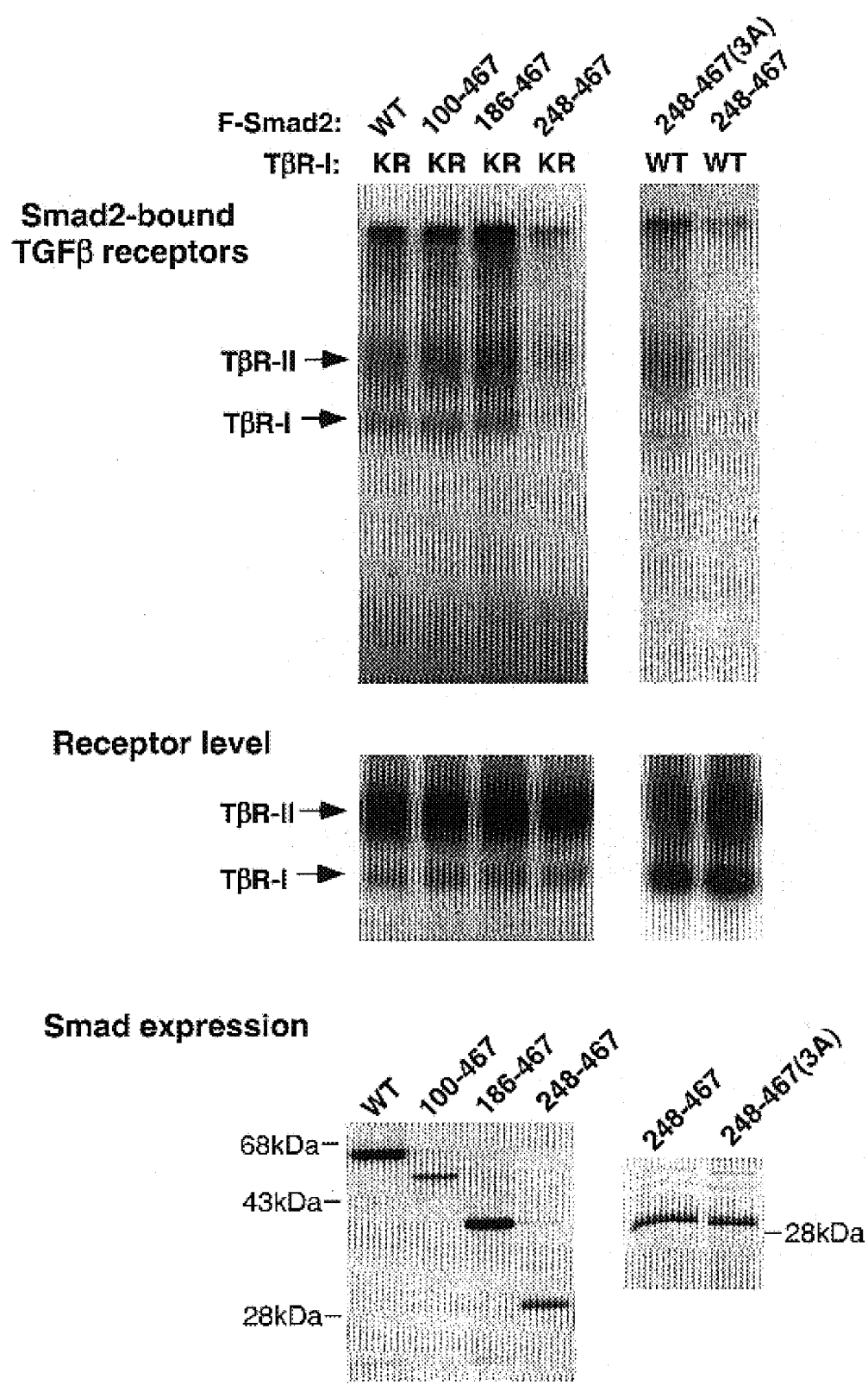
FIG. 13 shows the Smad 2 C domain retains the receptor docking ability. COS-1 cells were co-transfected with Flag-tagged wild type or mutant Smad2, wild type (WT) or kinase-defective (KR) TβR-I, and wild type TβR-II, and were affinity-labeled with [$^{125}$I]TGF-β1. The Smad2-bound and total receptors were resolved by SDS-PAGE and autoradiography as described in FIG. 11. Smad2 expression was determined in parallel by western blotting.

In order to localize the region of Smad2 required for association with the receptor, various Smad2 deletion mutants were tested for receptor binding activity (FIG. 13). To facilitate the analysis without altering the C-terminus of Smad2, the kinase defective TβR-I(KR) receptor construct was used, taking advantage of its enhanced Smad2 binding phenotype. Deleting half of the N domain [Smad2(100–467 of SEQ ID No. 3) construct] or the entire N domain [Smad2(186–467 of SEQ ID No. 3)] had no appreciable effect on Smad2-receptor association. Consistent with this, the N domain (1–185 of SEQ ID No. 3) alone had no detectable affinity for the receptor complex. Furthermore, the C domain alone [Smad2(248–467 of SEQ ID No. 3)] was still capable of associating with the receptor complex, albeit more weakly. This could be due to the fact that the C domain forms homo-oligomers less stably than the full-length protein and that this homomeric complex might cooperatively associate with the receptor complex. As with the full-length Smad2, the C domain interacted with the wild type TβR-I more stably when the C-terminal phosorylation sites of Smad2 were mutated [Smad2(248–467 of SEQ ID No. 3/3A) construct](FIG. 13).

EXAMPLE 13
L3 Loop Involvement in Smad2 Docking

Figure 12B:
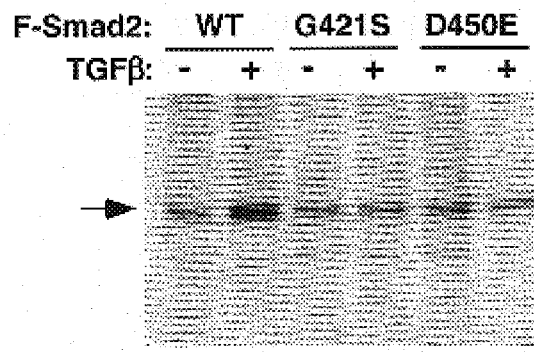
FIG. 12B: Smad2 phosphorylation was determined by transfecting Flag-tagged wild type or mutant Smad2 alone (−) or together (+) with TβR-I into R1B/L17 cells. After 48 hours, cells were labeled with [$^{32}$P]-orthophosphate for 2 hours and stimulated with (+) or without (−) TGF-β1 for 30 minutes. Cell lysates were immunoprecipitated with anti-Flag antibody and the immunoprecipitates analyzed by SDS-PAGE and autoradiography.
Figure 12C:
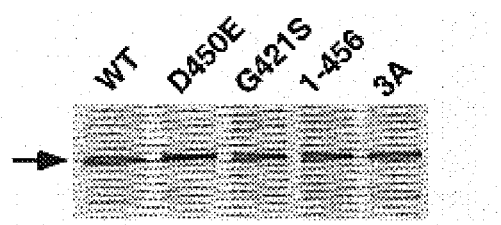
FIG. 12C: Expression of Smad2 constructs was checked by transfecting Flag-tagged Smad2 into COS-1 cells. Forty-eight hours post-transfection, cell lysates were resolved by SDS-PAGE and transferred onto membrane support. Western blotting was carried out using anti-Flag antibody.

Given these results, this search for a critical determinant of receptor docking focused in the C domain of Smad2 excluding the C-tail. Two missense mutations in this region inhibit receptor-mediated phosphorylation. A colorectal tumor-derived mutant form of Smad2 with an aspartic acid to glutamic acid mutation (D450E) is defective in receptor-dependent phosphorylation (FIG. 12B). However, this mutant was able to bind to the receptor as effectively as did the Smad2(3A) mutant (FIG. 12A), suggesting that the D450E mutation interferes with Smad2 phosphorylation and, as a result, enhances Smad2 binding to the receptor.

A different result was obtained with another mutant, Smad2(G421S), a highly conserved glycine residue whose mutation to serine in Drosophila Mad or to aspartic acid in *Caenorhabditis elegans* Sma-2 causes null or severe developmental phenotypes. The corresponding mutation in Smad1 inhibits BMP-induced phosphorylation of Smad1, in Smad2, the (G421S) mutation inhibited TGF-β-dependent phosphorylation (FIG. 12B). Unlike the D450E mutation, however, the G421S mutation inhibited Smad2 binding to the receptor (FIG. 12A). This suggested that Gly421 is involved, directly or indirectly, in Smad2 association with the receptor, and mutation of this residue may inhibit phosphorylation by preventing this association.

Figure 11B:
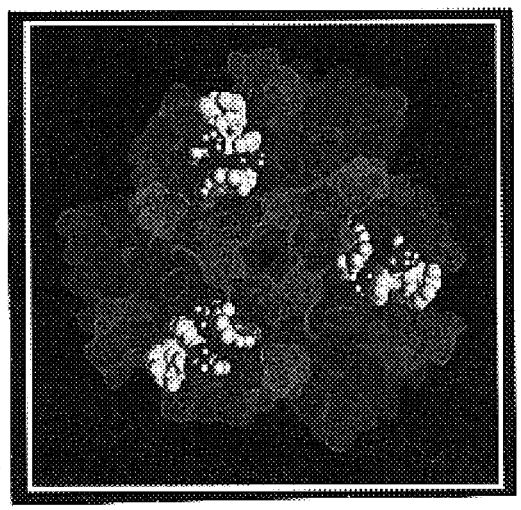
FIG. 11B shows the structure of the Smad4 C domain trimer highlighting the L3 loop in each monomer.
Figure 11C:
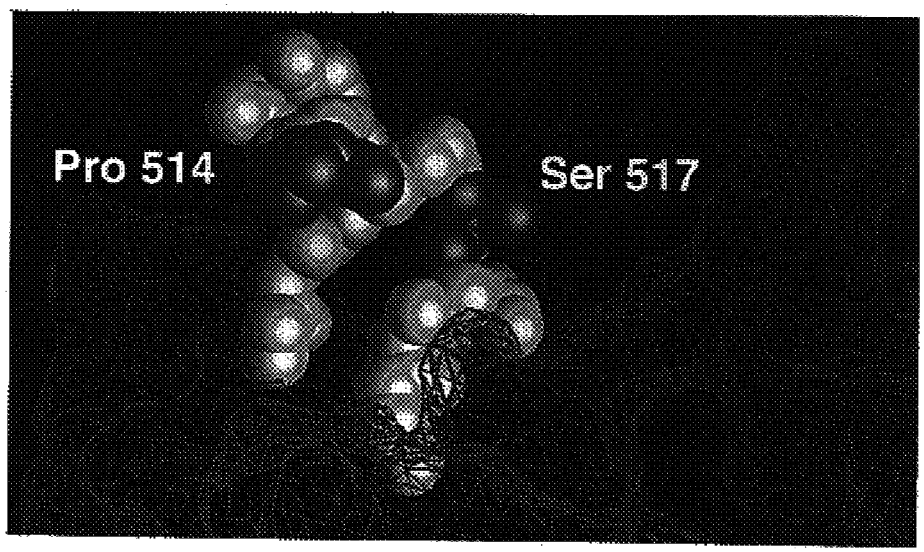
FIG. 11C shows the L3 loop (yellow) protruding from the core structure. The two group-specific amino acids are indicated in red.

Gly421 is located in a highly conserved segment of the Smad2 C domain (FIG. 11A). The crystal structure of Smad4 C domain reveals that this segment forms a solvent-exposed loop, the L3 loop, protruding from the β-sandwich core structure of the C domain (FIGS. 11B–11C). The L3 loop is predicted to participate in Smad interaction with other proteins. To show that the intergrity of the L3 loop is required for Smad2-receptor association, various residues that are absolutely conserved in this loop (G423, Y426, and RQ428,429; see FIG. 11A) were substituted with alanine. Gly423 of Smad2 corresponds to Gly348 in Sma-3, which is converted to Arg in a developmental mutant allele. As inferred from the Smad4 crystal structure, these mutations should not destabilize the folding of Smad2. These mutants were indistinguishable from the wild type Smad2 in their expression levels and their ability to form homo-oligomers (TABLE II). However, these mutations diminished (G423A) or abolished (Y426A and RQ428, 429AA) Smad2 binding to the TGF-β receptor complex. Defective receptor binding was accompanied by defective TGF-β-induced phosphorylation and defective association with Smad4 as measured by co-immunoprecipitation with a co-transfected epitope-tagged Smad4 construct.

TABLE II

Properties of Smad2 L3 loop Mutants

| L3 loop Mutation | Expression Level | Homo-oligomer | Receptor Binding | TGFβ-induced Phos-phorylation | Smad4 Binding |
|---|---|---|---|---|---|
| Wild Type | + | + | +++ | + | +++ |
| G421S | + | + | +/− | − | +/− |
| G423A | + | + | +/− | nd | +/− |
| A424P | + | + | +++ | + | +++ |
| Y426A | + | + | − | − | − |
| R427P | + | + | − | − | − |
| R427A | + | + | − | nd | − |
| RQ428, 429AA | + | + | − | − | − |
| T432K | + | + | − | − | − |
| T432A | + | + | − | nd | +/− |
| S433A | + | + | +/− | nd | +/− |

Table II: Properties of L3 loop mutants of Smad2. The expression level of Flag-tagged Smad2 constructs was determined by anti-Flag immunoblotting. Homo-oligomeric Smad2 interactions were assessed by co-transfection of Flag-tagged and HA-tagged version of each construct. Smad4 binding to Smad2 was determined by co-transfection of Flag-tagged Smad2 constructs and HA-tagged Smad4. In both cases, cell lysates were immunoprecipitated with anti-Flag antibody and the precipitates immunoblotted using anti-HA antibody. Receptor binding was determined by the level of $^{125}$I-TGF-β1-labeled receptors that was co-immunoprecipitated with Flag-tagged-Smad2 following two co-transfection schemes: kinase-defective TβR-I with full-length Smad2 constructs or wild type TβR-I with C-tail deletion versions of each Smad2 construct. The two transfection schemes yielded similar results with each Smad2 mutant. TGF-β1-stimulated phosphorylation of Flag-tagged Smad2 constructs was determined. In the binding assays, +++ indicates a wild type level of binding, +/− indicates a binding level 5-fold less than wild type, and − indicates no detectable binding. nd, not determined.

The effect of these mutations strongly suggested that the L3 loop plays a crucial role in mediating Smad2-receptor interactions. Several other mutations in the L3 loop also inhibited Smad2 association with the receptor. These include R427P, R427A, T432K, T432A and S433A (TABLE II). Various highly conserved residues in other regions of the Smad2 C domain that are surface-exposed as predicted from the tertiary structure of the the related Smad4 C domain were also mutated. Mutations in α-helix 2 (P360R; QRY364-366YHH; W368F), in α-helix 3 (A392Q), and in α-helix 4 A404T; Q407E) did not diminish the binding of Smad2 to the receptor complex, suggesting that the integrity of these other regions is not essential for Smad-receptor association.

EXAMPLE 14
The L3 Loop Specifies Smad-receptor Interactions

Figure 14A:
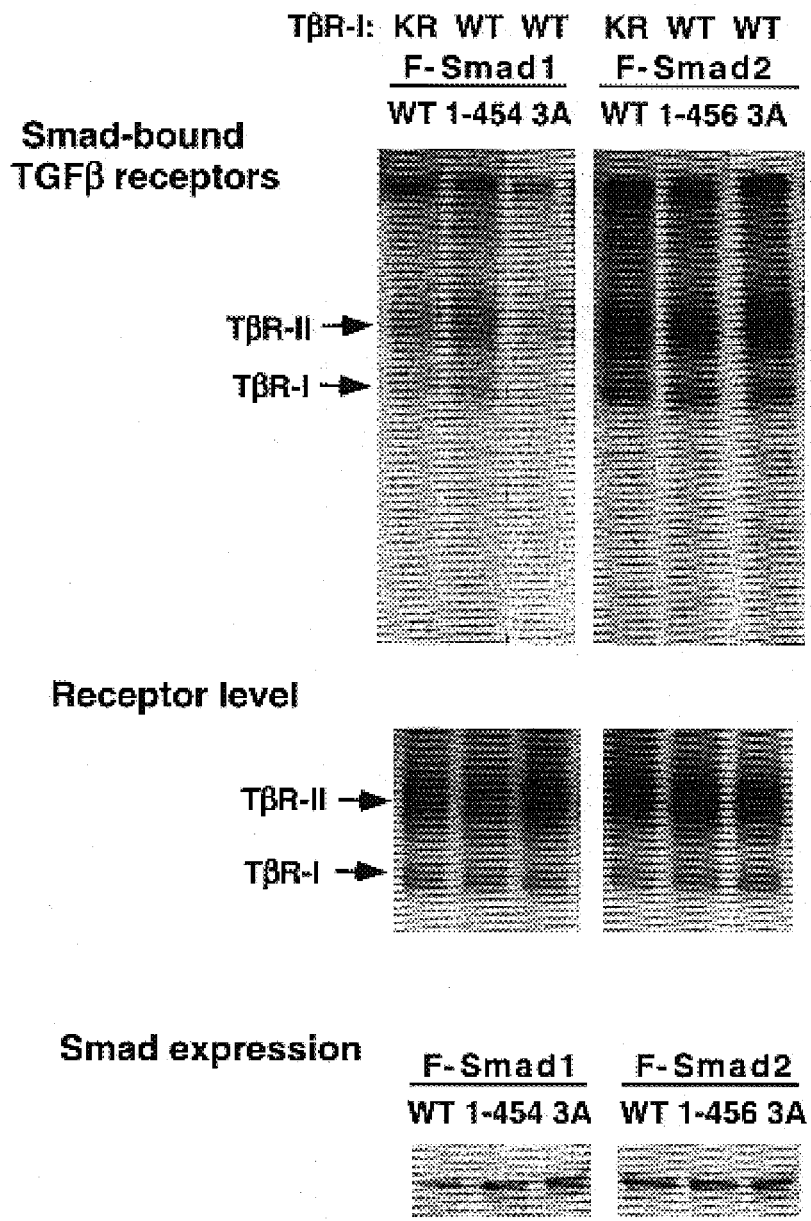
FIG. 14A: Differential binding affinity of Smad1 and Smad2 to the TGF-β receptor complex.

A sequence comparison of the TGF-β-activated Smads (Smads 2 and 3) and the BMP/Dpp-activated Smads (Smads 1, 5, 9 and Mad) reveals that the L3 loop is invariant within each group but differs at two positions (corresponding to residues 427 and 430 in Smad2) between these two groups (FIGS. 11A and B). To determine whether the L3 loop can define the specificity of Smad-receptor interaction, the ability of Smad1 and Smad2 to associate with the TGF-β receptor complex was first compared (FIG. 14A). The relative binding of Smad1 versus Smad2 to the TGF-β receptor complex was assessed in three different co-transfection schemes that optimize the TGF-β receptor-Smad interaction: wild type Smad with kinase-defective receptor; wild type receptor with Smad C-tail deletion constructs; and, wild type receptor with Smad C-tail serine to alanine mutations. All three schemes yielded consistent results showing that Smad2 associated with the TGF-β receptor complex 5- to 15-fold more effectively than Smad1 (FIG. 14A).

Figure 14B:
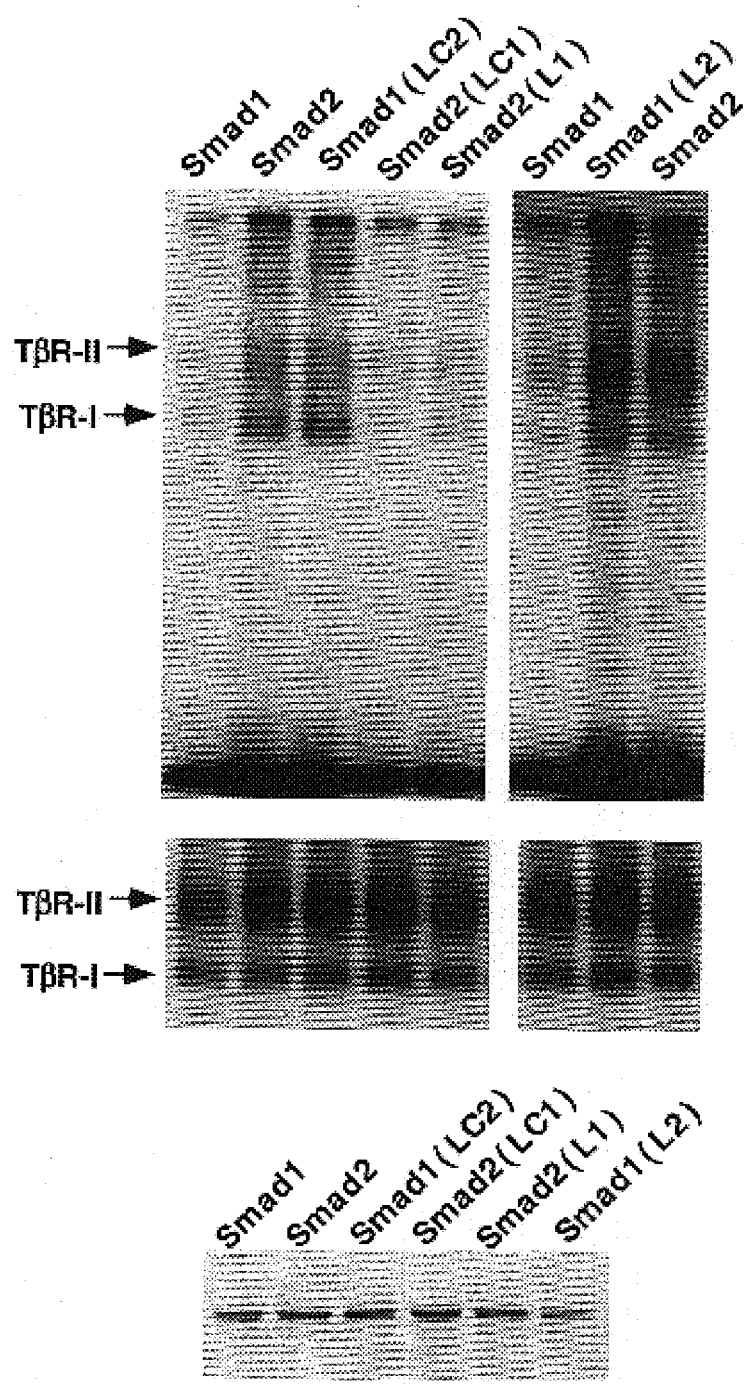
FIG. 14B: The L3 loop determines the specificity of Smad-receptor interaction. The interaction between the indicated Smad constructs and the TGF-β receptor complex was assessed as described in FIG. 11. Smad construct expression levels as determined by anti-Flag immunoblotting are shown in the bottom panel.

Whether the L3 loops of Smad1 and Smad2 accounts for this differential affinity was tested. To this end, a Smad2 construct was created containing the Smad1 L3 loop (by introducing the mutations R426H and T430D), and the reciprocal Smad1 construct. This Smad2 construct, hereafter referred to as Smad2(L1), had poor TGF-β receptor binding ability compared to Smad2, whereas the reciprocal construct Smad1(L2) was able to bind the TGF-β receptor complex as effectively as did Smad2 (FIG. 14B). Switching the C-tails of Smads 1 and 2 in addition to the L3 loop [Smad1(LC2) and Smad2(LC1) constructs] had no additional effect on receptor binding (FIG. 14B), consistent with the observation that the Smad2 C-tail does not contribute to docking to the receptor (FIG. 12A). As expected, C-tail chimeras [Smad1 (C2) and Smad2(C1) constructs] behaved like their wild type counterparts with regard to binding to the receptor. Thus, the Smad L3 loop critically determines the specificity of the Smad-receptor interactions.

EXAMPLE 15
Switching Smad Activation

Figure 15A:
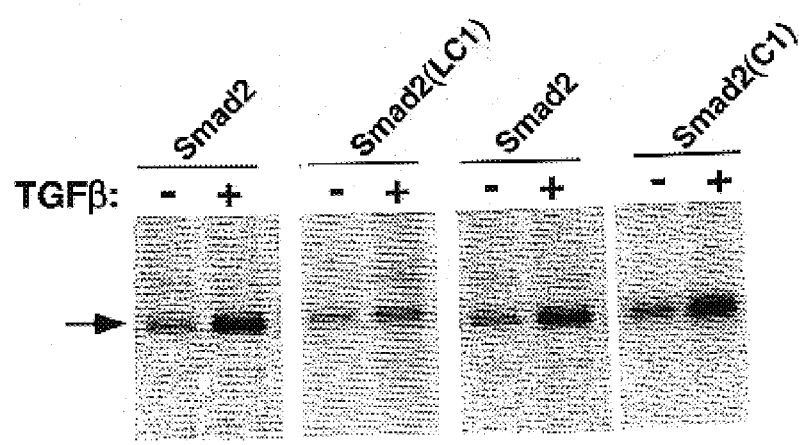
FIGS. 15A–15C show the role of the L3 loop and C-tail in the phosphorylation of Smads by the type I receptors.
Figure 15B:
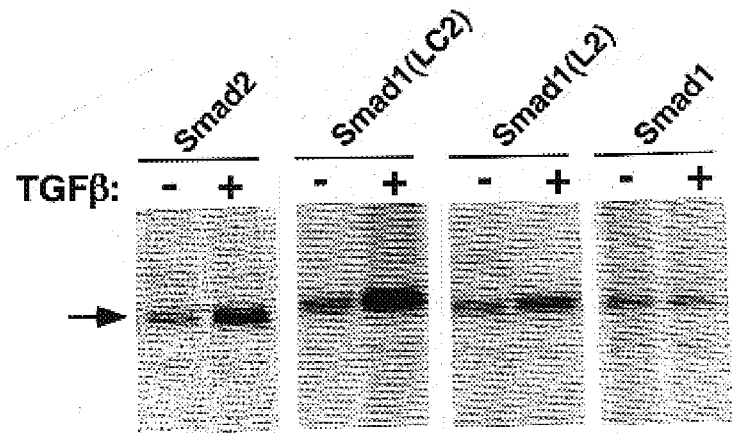
Figure 15C:
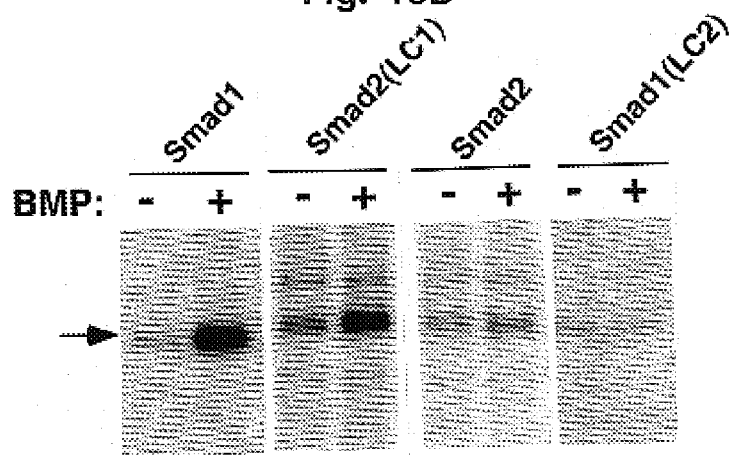

As shown in TABLE II, optimal receptor binding for Smad2 appeared to be necessary for the optimal phosphorylation of the C-tail (C). Consistent with this notion, TGF-β stimulation failed to phosphorylate Smad2(LC1) (FIG. 15A), which is defective in binding to the TGF-β receptor, but phosphorylated Smad1(LC2) as effectively as it phosphorylated wild type Smad2 (FIG. 15B). The requirements for Smad phosphorylation by activated BMP receptors was also investigated. Smad2(LC1) was phosphorylated in response to BMP receptor activation whereas Smad1(LC2) was not (FIG. 15C). Thus, Smads 1 and 2 can be phosphorylated by a heterologous receptor when they are allowed to dock to this receptor via a heterologous L3 loop.

To determine whether optimal receptor binding is sufficient for optimal C-tail phosphorylation, TGF-β receptor-mediated phosphorylation of the Smad1(L2) and Smad2 (C1) constructs was examined. Both constructs bind to the TGF-β receptor but contain a Smad1 C-tail. Smad1(L2) was phosphorylated in response to TGF-β less extensively than were Smad2 or Smad1(LC2) (FIG. 15B), even though all three constructs could bind to the TGF-62 receptor equally well (see FIG. 14B). On the other hand, Smad2(C1) was phosphorylated almost as efficiently as Smad2 in response to TGF-β (FIG. 15A). Taken together, these data suggest that the non-conserved residues in the C-tail (see FIG. 11A) have a limited influence on the phosphorylation of the C-terminal serines by the TGF-β receptor kinase.

Figure 16A:
FIG. 16A shows the association of the receptor-regulated Smads with Smad4. COS-1 cells transfected with the indicated Flag-tagged Smad1 or 2 constructs, HA-tagged Smad4 and activated TβR-I were treated with TGF-β1 for 1 hour. After Smad complexes were immunoprecipitated using anti-Flag antibody, Smad4 was visualized by western blotting with anti-HA antibody.
Figure 16B:
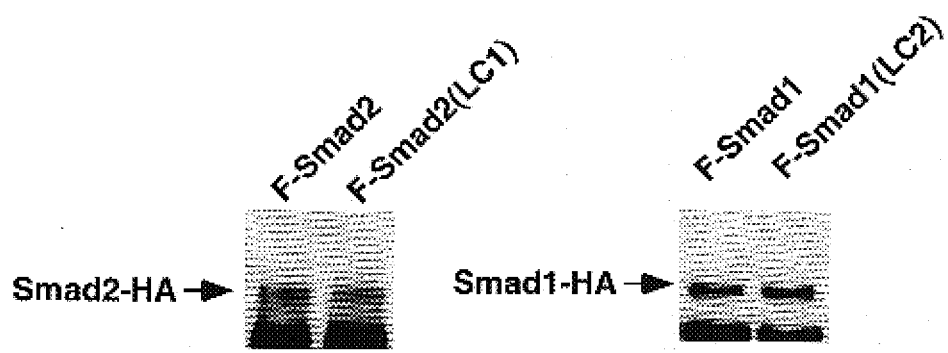
FIG. 16B: COD-1 cells were transfected with wild type Smad2 C-terminally tagged with HA epitope (Smad2-HA) and wild type and mutant Smad2 N-terminally tagged with Flag epitope (F-Smad2) (left panel), or transfected with wild type Smad1 C-terminally tagged with HA epitope (Smad1-HA) and wild type and mutant Smad1 N-terminally tagged with Flag epitope (F-Smad1) (right panel). After 48 h, cells were lysed and immunoprecipitation was carried out with anti-Flag antibody and Smad homomeric complexes were visualized by anti-HA immunoblotting.
Figure 17:
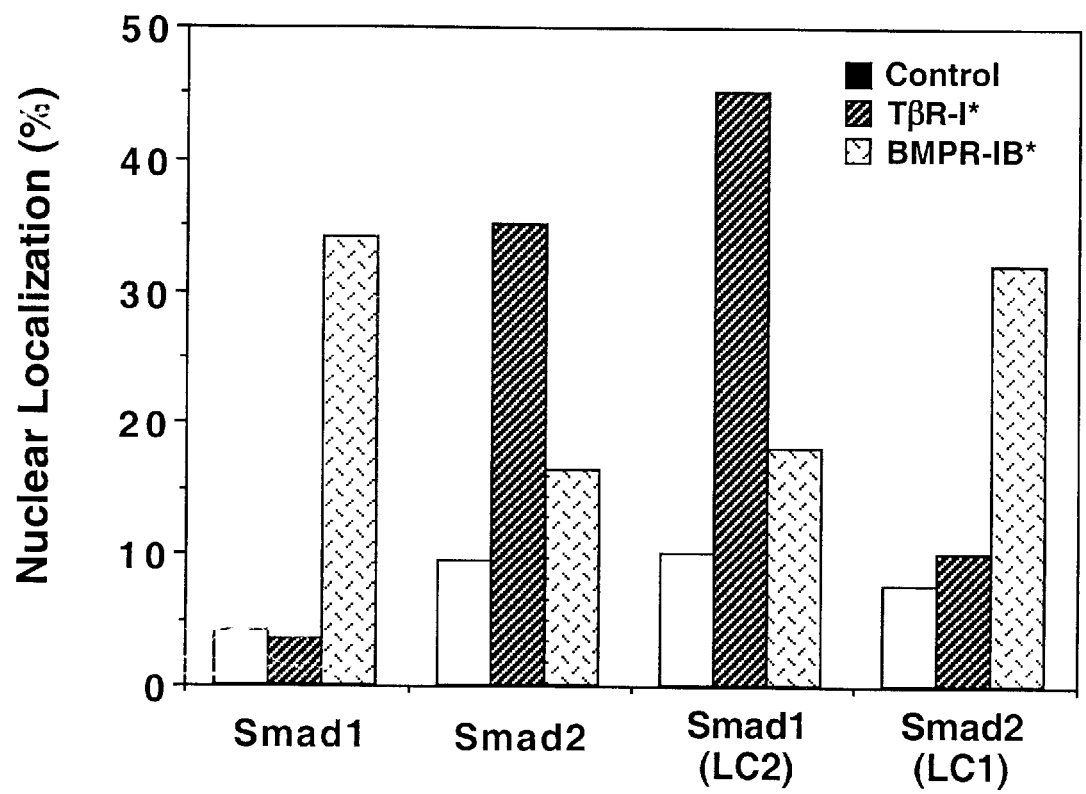
FIG. 17 shows the percentage of Smads localized in the nucleus after translocation in response to TGF-β1 or BMP2. Vectors encoding the indicated Flag-tagged Smad contructs alone (Control) or together with either TβR-I(T204D) (TβR-I*) or BMPR-IB(Q203D) (BMPR-IB*) were transfected into HepG2 cells. 48 hours post-transfection, cells were incubated with TGF-β1 or BMP2 and immnuofluorescence was visualized with primary mouse anti-Flag antibody and secondary FITC-conjugated goat anti-mouse antibody. Nuclear localization was confirmed with DAPI DNA staining (data not shown). Percentage of Smads localized in the nucleus was determined by counting 200 to 300 immunofluorescence-positive cells for each sample.

To corroborate that the switch in receptor docking and phosphorylation specificity by introduction of the Smad2 L3 loop and C-tail into Smad1 resulted in the activation of Smad1(LC2) by TGF-β, the ability of this construct to associate with Smad4 was determined. Smad1(LC2) was able to associate with Smad4 in response to TGF-β whereas Smad2(LC1) was not (FIG. 16A). Swapping the L3 loop and the C-tails between Smads 1 and 2 had no detectable effect on their ability to form homo-oligomers (FIG. 16B). The ability of the TGF-β receptors and BMP receptors to induce Smad nuclear translocation was also switched in the Smad1 (LC2) and Smad2(LC1) mutants (FIG. 17). Like Smad2, Smad1(LC2) was translocated to the nucleus in response to TGF-β but not BMP. On the other hand, like Smad1, Smad2 (LC1) was translocated to the nucleus in response to BMP but not TGF-β. Thus, the receptor input necessary to induce association of Smad1 or Smad2 with Smad4 and their movement to the nucleus is provided through a receptor interaction that is dependent on, and specified by, the L3 loop.

Specificity is an essential property of signal transduction pathways. In the TGF-β signaling system, specificity is determined by ligand activation of a particular receptor combination which, in turn, recruits and phosphorylates a particular subset of Smad proteins. The present invention demonstrates the Smad-receptor interaction, the molecular basis for its specificity and identifies the L3 loop as a discrete surface structure in Smad proteins necessary for the Smad-receptor interaction and its specificity.

The differential ability of Smads 1 and 2 to associate with the TGF-β receptor complex is consistent with their known responsiveness to these receptors: Smad2, which mediates TGF-β signaling, associates with the TGF-β receptor complex approximately 10-fold better than Smad1, which is primarily a mediator of BMP signaling. This receptor interaction is required for Smad2 phosphorylation since docking-defective mutants of Smad2 are not phosphorylated in response to TGF-β. However, the Smad2 phosphorylation sites themselves, along with the adjacent sequence in the 11-amino acid C-tail region, are dispensable for the receptor interaction. This conclusion is based on the observation that the TGF-β receptor associates with a Smad2 deletion mutant lacking the C-tail.

These observations predict that a region other than the C-tail mediates Smad2 interaction with the activated TGF-β receptor complex. Since the isolated C domain of Smad2 still binds to the TGF-β receptor complex and, as with full-length Smad2, this interaction can be further enhanced by eliminating receptor-mediated Smad phosphorylation, a critical determinant of Smad docking resides in the C domain. Indeed, such a determinant was identified in a highly conserved region that, by analogy to the crystal structure of the Smad4 C domain, is predicted to form a highly solvent-exposed loop, the L3 loop, that is poised for protein-protein interactions. Introduction of various mutations into the L3 loop, including developmental mutations previously observed in Drosophila Mad and *Caenorhabditis elegans* Sma-2 and -3, diminishes the ability of Smad2 to associate with the TGF-β receptor complex. None of these mutations has appreciable effects on Smad2 expression level or its ability to homo-oligomerize, as predicted from the fact that the L3 loop is not part of the Smad C domain core structure.

The sequence of the L3 loop, which is invariant among TGF-β-activated Smads (Smads 2 and 3) and among Smads thought to be activated by BMP (Smads 1, 5, and 9) or Dpp (Mad), differs at two positions between these two groups. These two amino acids also differ in Smad4 as well as Smads 6 and 7 (FIG. 11A). In Smad4, these two positions are highly exposed (FIG. 11B), and the same is likely to occur in other Smads given their overall structural similarity to Smad4. As further testament to the importance of the L3 loop, switching these two amino acids in Smad1 and 2 induces a gain or a loss, respectively, in their ability to bind to the TGF-β receptor complex. This switch is reiterated in receptor-mediated phosphorylation of these Smads, indicating that the L3 loop-dependent receptor interaction is necessary and sufficient for receptor phosphorylation. The homologous C-tail containing the phosphorylation sites and adjacent sequence may ensure an optimal receptor-mediated phosphorylation. A switch in agonist-induced association with Smad4 and nuclear translocation accompanies this switch in phosphorylation.

Unlike the receptor-regulated Smads, Smad4 lacks a C-terminal SS(V/M)S phosphorylation motif and does not appear to associate with the receptors on its own. What then is the function of the L3 loop in Smad4? Based on structural considerations and the observation that a mutation (G508S) in the Smad4 L3 loop abolishes the ability of Smad4 to associate with Smad2, the Smad4 L3 loop mediates the association with receptor-activated Smads. The importance of the Smad4 L3 loop for Smad2-Smad4 interaction has been shown by showing that mutations of other residues in the Smad4 L3 loop (Y513A; and RQ515,516AA) also lead to the loss of TGF-β-inducible Smad2-Smad4 association in transfected COS-1 cells. Smad4 is required for various responses to TGF-β, activin and BMP by acting as a partner for the corresponding receptor-activated Smads. In addition, Smad4 can associate with these Smads in yeast, suggesting that the interaction may be direct. Smad L3 loops, therefore, are implicated in two distinct. types of interactions. Among the receptor-regulated Smads the L3 loop may mediate Smad-receptor interactions, whereas the more divergent Smad4 L3 loop (see FIG. 11A) may mediate Smad4 interaction with receptor-activated Smads. The L3 loop of receptor-regulated Smads may have a dual function as a receptor-interacting region and, upon phosphorylation of the C-tail, as a Smad4-interacting region.

Since the C-tail of receptor-regulated Smads serves as a substrate for the type I receptor kinase, it must physically contact the receptor. But this interaction apparently does not contribute significantly to the stability of the interaction that precedes phosphorylation, at least as determined with Smad2 and the TGF-β receptor. In fact, the TGF-β receptor-Smad2 interaction is weakened upon phosphorylation by the receptor, as either phosphorylation-defective Smad2 mutants or a kinase-defective TGF-β type I receptor mutant enhances Smad-receptor association. It is not clear how Smad phosphorylation may promote its dissociation from the receptor. A gain of affinity for Smad4 might contribute to Smad2 dissociation from the receptor upon phosphorylation. However, the Smad2(3A) mutant still showed an elevated receptor-binding activity as compared to the wild type Smad2 in the Smad4-deficient colorectal carcinoma cell line SW480.7. Thus, an increased affinity for Smad4 may not be the only event driving dissociation of the phosphorylated Smad2 from the receptor complex.

Although two residues in the L3 loop are sufficient to dictate the specificity of the Smad-receptor interaction, the entire L3 loop may not be sufficient to fully support this interaction. It could be that a direct Smad-receptor interaction is weak and requires oligomeric forms of both the receptors and the Smads for cooperative binding. Alternatively, the Smad-receptor interaction might be indirect, requiring a hitherto unidentified adaptor protein. Regardless of the mechanism, the evidence at hand identifies the L3 loop as a critical determinant of specific Smad-receptor interactions.

EXAMPLE 16

Cell Culture, Xenopus Injections and Animal Cap Assays

R1B/L17 and COS-1 cells were maintained[37]. HepG2 cells were maintained in minimal essential medium (MEM, GIBCO-BRL) supplemented with 10% fetal bovine serum (FBS), nonessential amino acids and 2 mM sodium pyruvate. Mouse embryonal carcinoma P19 cells were cultured in DMEM medium supplemented with 10% FBS.

Receptor RNA (10 nl, 2 ng) was injected into the animal pole of two-cell embryos. Animal caps were explanted at the blastula stage and incubated to the tailbud stage (stage 28). RT-PCR of the indicated markers was performed[9].

EXAMPLE 17

Protein Interaction, Phosphorylation and Immunofluorescence Assays

Mutant receptor and Smad constructs were generated by PCR using appropriate oligonucleotides. Helix 2 exchange mutants were generated by exchanging the six residues highlighted in the helix 2 region in FIG. 20. Mutations were verified by DNA sequencing. Wild-type and mutant receptors were C-terminally tagged with a hemagglutinin (HA) epitope and were subcloned into the mammalian expression vector pCMV5. Cells were transiently transfected with the indicated constructs or empty vector by the DEAE-dextran method[37]. Phosphorylation of Smad1 and Smad2 was tested in R-1B/L17 cells by co-transfecting Flag-tagged Smad constructs and the indicated receptor constructs, labeling the cells with [$^{32}$P]orthorphosphate for 2 h, followed by incubation with 1 nM TGF-β1 or 5 nM BMP2 for 30 min, and anti-Flag immunoprecipitation[50]. Expression levels of transfected proteins was determined by immunoprecipitation from [$^{35}$S]methionine/cysteine labeled cells. Flag-tagged R-Smad interaction with HA-tagged Smad4 or myc-tagged Fast 1 was determined in COS-1 cells by anti-Flag immunoprecipitation and anti-HA or anti-myc western immunoblotting[9,49]. For Smad immunofluorescence assays, HepG2 cells were transfected overnight with DNA constructs as indicated, using the standard calcium phosphate-DNA precipitation method. Twenty-four h after transfection, cells were transferred onto chamber slides (Nunc, Inc.). Two days later, cells were stimulated with 5 nM BMP2 or 1 nM TGF-β1 for 1 h and processed for anti-Flag immunofluorescence[50]. The percentage of cells showing nuclear staining was determined by counting 200–300 positive cells.

EXAMPLE 18

Reporter Assays and Receptor Assays

Activation of the p3TP-luciferase reporter construct[32] was analyzed in R1B/L17 cells[37]. To measure the activity of a Xvent2-luciferase reporter[15], P19 cells were transfected with this construct, TβR-1 and TβR-II. The next day, cells were incubated with 0.5 nM TGF-β1 or 1 nM BMP2, and luciferase activity was measured 20 h later. To measure the activity of a Mix.2 ARE reporters (A3-CAT or A3-luciferase)[45], R1B/L17 cells were transfected with these reporters, Fast1 and the indicated receptor constructs. The next day, cells were treated with 0.5 nM TGFβ1 or 1 nM BMP2 for 20 h and the reporter gene activity was determined[49]. A GAL4 DNA binding domain fusion with Fast1 was created by subcloning Fast1 into pGAD424 (Clontech). GAL4-Fast1 activation was determined in R-1B/L17 cells by cotransfection with the indicated constructs, and incubation with BMP2 for 14 h on the following day.

TGF-β1 and BMP2 were labeled with sodium [$^{125}$I][67]. To detect receptor-Smad interactions, COS-1 cells were transiently transfected with constructs that encode Smad1 and Smad2 lacking the last 11 amino acids [Smad1(1–454 of SEQ ID No. 2) and Smad2(1–456 of SEQ ID No. 3) constructs], and the indicated receptor constructs. After 40–48 h, cells were labeled by cross-linking to receptor-bound [$^{125}$I]TGF-β1 or [$^{125}$I]BMP2[50].

EXAMPLE 19

Determinants of Specificity in the Type I Receptor

The cytoplasmic domain of TGF-β family type I receptors was searched for regions that might determine the specificity of their interactions with R-Smads. One candidate was the GS domain, a 30 amino-acid region located just upstream of the kinase domain in all type I receptors[63]. The GS domain contains sites whose phosphorylation by the type II receptor activate the type I receptor kinase[65]. Phosphorylation sites in receptor tyrosine kinases function as docking sites for signal transduction molecules[55]. However, replacing the GS domain in the TGF-β type I receptor, TβR-I, with the GS domain from one of the most divergent member of the TβR-I family in vertebrates, ALK2, did not alter the signaling specificity of TβR-I[63]. This result argued against a role of the GS domain in determining the specificity of receptor-Smad interactions.

Figure 18A:
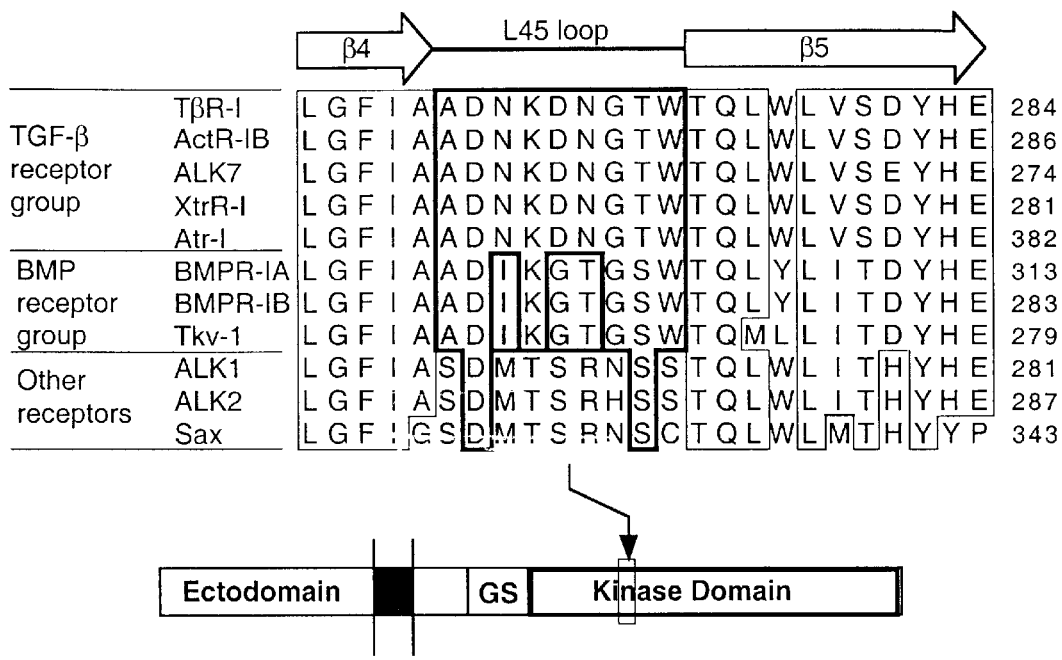
FIG. 18A shows the L45 loop sequences of the TGF-β type I receptor family. Conserved amino acids are boxed. Three groups of functionally related receptors have each a characteristic L45 loop sequence. ALK1 is also known as TSR-1, and ALK2 as ActR-I or Tsk7L.

A 9-amino acid segment in the receptor kinase domain, known as the "L45 loop", was also of interest (FIG. 18A). It has been shown that replacement of all but the L45 loop in the kinase domain of TβR-I with the corresponding regions from ALK2 yields a construct that still mediates TGF-β responses[38]. As predicted from the conserved structure of protein kinases, the L45 loop links β-strands 4 and 5, and is not part of the catalytic center[59]. The L45 loop differs between type I receptors of different signaling specificity, such as the TGF-β receptors and the BMP receptors, but is highly conserved between receptors of similar signaling specificity such as TβR-I and the activin receptor ActR-IB, or the BMP receptors from human (BMPR-IA and BMPR-IB) and Drosophila (Thick veins) (FIG. 18A).

Figure 18C:
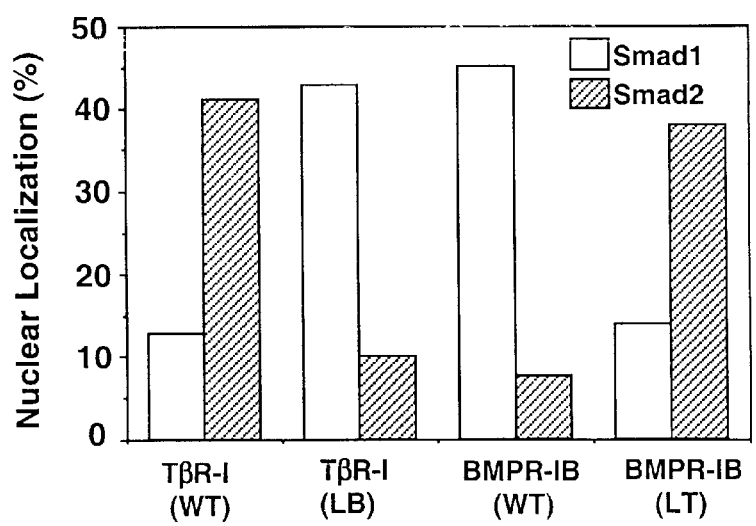
FIG. 18C shows nuclear translocation of R-Smads induced by wild type an d L45 mutant type I receptors. HepG2 cells were transfected with Flag-tagged Smad1 or Smad2, the indicated type I receptors, and their corresponding type II receptors. Cells were incubated with TGF-β1 or BMP2 for 1 h and subjected to anti-Flag immunofluorescence.
Figure 18B:
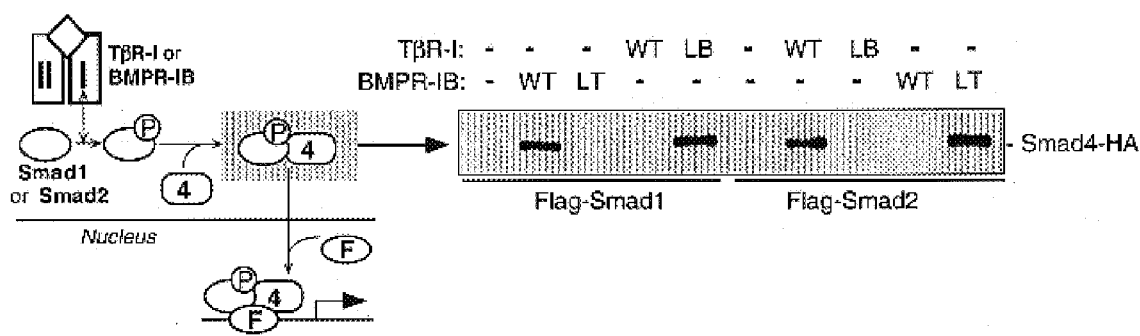
FIG. 18B shows R-Smad association with Smad4. Scheme, a TGF-β signal transduction pathway with a type II receptor (II), a type I receptor (I), R-Smad phosphorylation (P), Smad4 (4) and a DNA-binding factor (F). COS1 cells were transfected with Flag-tagged Smad1 or Smad2, HA-tagged Smad4, the indicated wild type (WT) or mutant type I receptors, and the corresponding type II receptors, TβR-II or BMPR-II. R-Smad binding to Smad4 was determined after incubation with TGF-β or BMP2.

To investigate the role of the L45 loop, TβR-I and BMPR-IB were used. The L45 loops of these two receptors differ by three non-conservative amino acid substitutions (FIG. 18A). Constructs encoding these receptors with their L45 loops swapped were made by introducing N2671, D269G, N270T and T272S mutations in TβR-I, and the reciprocal mutations in BMPR-IB. These constructs showed a complete switch in their ability to activate Smad1 and Smad2. Compared to the wild type receptors, TβR-I with the BMPR-I L45 loop [TβR-I(LB) construct] lost the ability to induce the formation of a Smad2-Smad4 complex and gained the ability to induce the formation of a Smad1-Smad4 complex (FIG. 18B). The reciprocal pattern was observed with BMPR-IB containing the TβR-I L45 loop [BMPR-IB(LT) construct] (FIG. 18B). These mutations also switched the ability of the receptors to induce translocation of Smad1 and Smad2 into the nucleus (FIG. 18C).

Figure 19A:
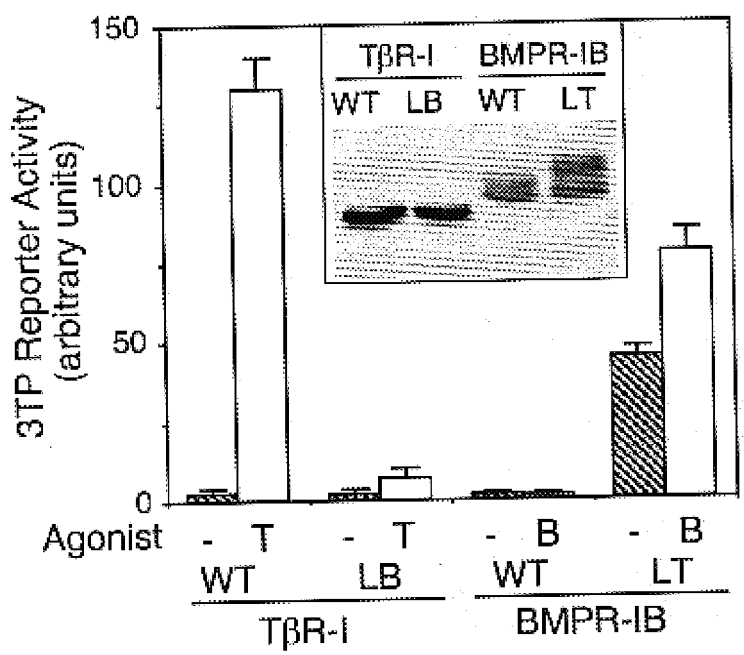
FIG. 19A shows the activation of the TGF-β-responsive reporter 3TP-luciferase in TβR-I-defective R1B/L17 cells transfected with wild-type or mutant receptors. Cells were incubated with TGF-β (T) or BMP2 (B), and luciferase activity was determined in triplicate samples. Inset, HA-tagged receptors immunoprecipitated from metabolically labeled cells as controls.
Figure 19B:
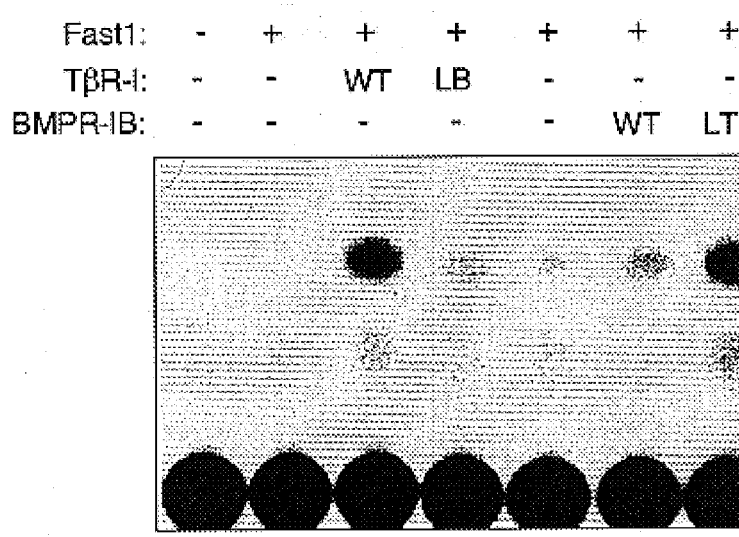
FIG. 19B shows the activation of the A3-CAT reporter containing activin- and TGF-β-responsive Mix.2 elements. R1B/L17 cells were transfected with Fast1 and receptor constructs. TβR-I transfectants were incubated with TGF-β and BMPR-IB transfectants with BMP2, and CAT activity was determined.
Figure 19C:
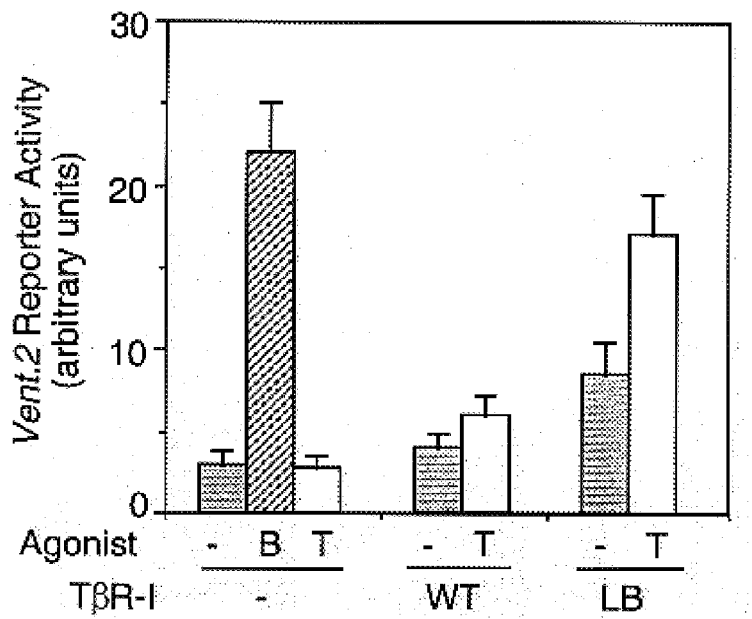
FIG. 19C shows the activation of the BMP-responsive reporter Xvent 2-luciferase in P19 cells transfected with TβR-II and wild type or mutant TβR-I. Cells were incubated with BMP2 (B) or TGF-β (T), and luciferase activity was determined.
Figure 19D:
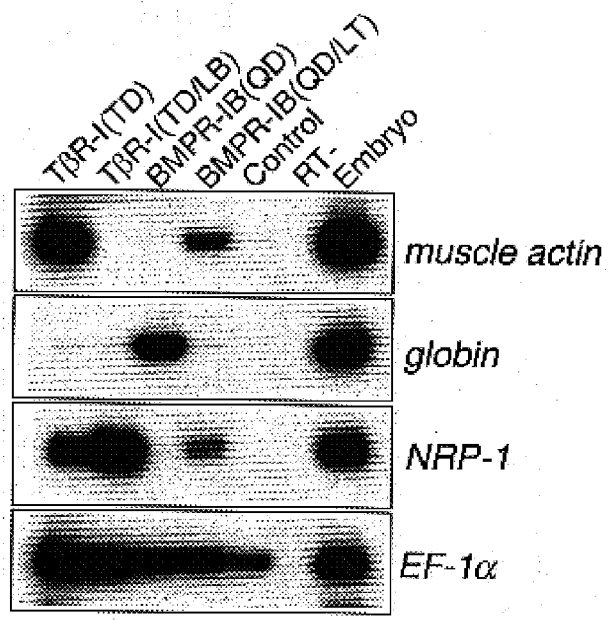
FIG. 19D shows induction of markers of dorsal mesoderm (muscle actin), ventral mesoderm (globin) and neural tissue (NRP-1) in Xenopus embryos. RNAs encoding the indicated constitutively active receptor forms were injected into the animal pole of two-cell embryos. Expression of muscle actin, globin, NRP-1, and EF-1a (as control) in animal caps from these embryos was determined. Animal caps from uninjected embryos (Control), whole embryos (Embryo) and a sample without reverse transcription (−RT) were included.

The L45 exchange mutations switched the signaling specificity of the receptors. BMPR-IB(LT) gained the ability to mediate TGF-β- and activin-like responses including activation of the 3TP-lux reporter construct, which contains a TGF-β response element from plasminogen activator inhibitor-1 and three AP-1 binding sites[64] (FIG. 19A), and a reporter construct (A3-CAT) that contains activin- and TGF-β-responsive Fast1 binding sites from the Mix.2 promoter[45] (FIG. 19B). TβR-I(LB) lost the ability to mediate these responses (FIGS. 19A and B) but gained the ability to mediate a BMP-like response, namely, activation of the Vent.2 promoter from Xenopus[15] in P19 mouse embryonal carcinoma cells (FIG. 19C). Valine mutations of two conserved threonines (T272 and T274) at or near the TβR-I L45 loop did not impair 3TP-lux activation by TβR-I. Further evidence for a switch in signaling specificity was obtained using Xenopus embryo ectoderm explants. In these explants, TGF-β/activin signaling induces dorsal mesoderm and, indirectly, neural tissue via Smad2[16,40] whereas BMP signaling induces ventral mesoderm via Smad1[40,14,61]. These effects can be observed using activated mutant forms of the corresponding type I receptors[41,58] (see FIG. 19D). However, an activated BMPR-IB receptor containing the L45 loop from TβR-I [BMPR-IB(QD)(LT) construct] lost the ability to induce expression of the ventral mesoderm marker globin and gained the ability to induce the dorsal mesoderm marker muscle actin and the pan-neural marker NRP-1 (FIG. 19D). The reciprocal construct, TβR-I(TD) (LB), showed an incomplete switch in signaling specificity in this assay system, losing the capacity to induce muscle actin without a gain of globin induction or a loss of NRP-1 induction (FIG. 19D).

Figure 20A:
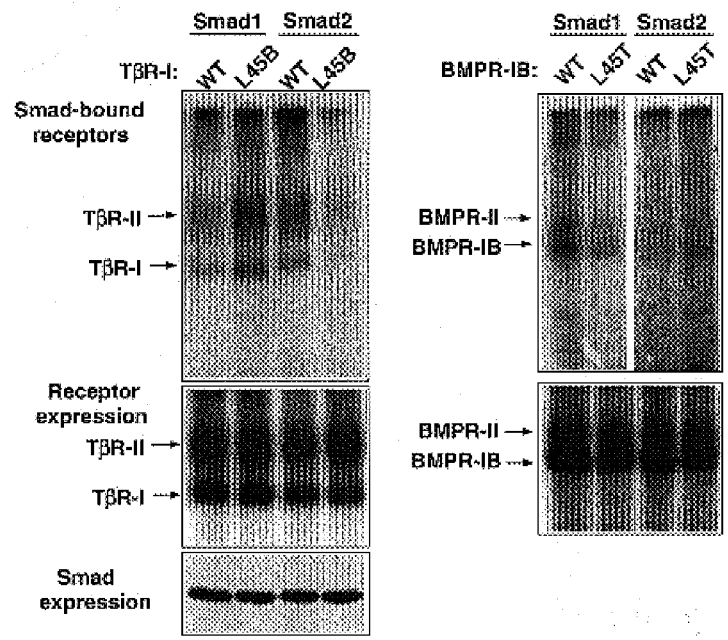
FIG. 20A shows the receptor-Smad association in COS-1 cells transfected with the indicated type I receptors, the corresponding type II receptors, and Flag-tagged Smad1 (1–454 of SEQ ID No. 2) or Smad2(1–456 of SEQ ID No. 3). Receptors were cross-linked to [$^{125}$I]TGF-β1 (left panel) or [$^{125}$I]BMP2 (right panel). Smad-bound receptors were visualized by anti-Flag immunoprecipitation, SDS-Page and autoradiography (upper panels). Total cell lysates were analyzed to control for receptor expression (middle panels). Smad expression was controlled by immunoprecipitation from metabolically labeled cells (lower panels).
Figure 20B:
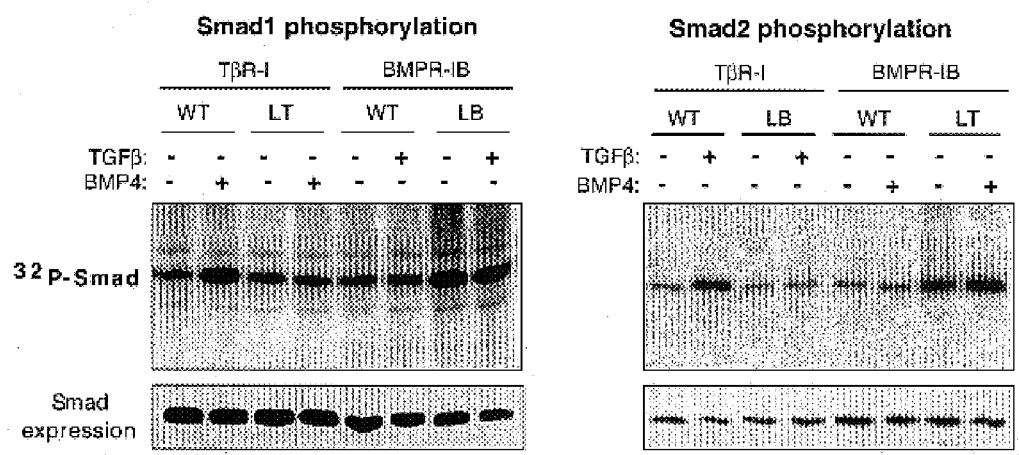
FIG. 20B shows Smad phosphorylation determined in L17 cells transfected with Flag-tagged Smads, the indicated type I receptors, and the corresponding type II receptors. Cells were labeled with [$^{32}$P]phosphate, incubated with TGF-β1 or BMP2, and immunoprecipitated with anti-Flag.

The switch in the signaling specificity of TβR-I(LB) and BMPR-IB(LT) correlated with a switch in their ability to recognize and phosphorylate Smads 1 and 2. The interaction between TGF-β family receptors and R-Smads is transient but can be visualized using mutant Smads lacking the receptor phosphorylation region[50]. As shown by co-precipitation of affinity-labeled receptors with phosphorylation-defective Smads, TβR-I(LB) gained affinity for Smad1 and lost affinity for Smad2 compared to the wild-type receptors, whereas BMPR-IB(LT) lost affinity for Smad1 and gained affinity for Smad2 (FIG. 20A). This switch extended to the pattern of receptor-dependent Smad phosphorylation. TβR-I and BMPR-I mediate C-terminal phosphorylation of Smad2[30] and Smad1[48], respectively (see FIG. 20B); basal phosphorylation (see FIG. 20B) is due to MAP kinase action on inhibitory sites located in the central region of Smads[47]. In contrast to the effects of the wild type receptors, transfection of TβR-I(LB) elevated the phosphorylation of Smad1 whereas transfection of BMPR-IB(LT) elevated the phosphorylation of Smad2 (FIG. 20B). Interestingly, the increases in Smad phosphorylation caused by transfection of the L45 mutant receptors were ligand-independent. Indeed, TβR-I(LB) and BMPR-IB(LT) were hyperactive compared to the wild type receptors in in vitro kinase assays. The phenotype of a TβR-I allele containing a mutation (G261E) three residues upstream of the L45 loop had previously suggested that this region is involved in receptor activation[62]. However, despite their elevated kinase activity, the L45 mutant receptors had a clear switch in substrate specificity since TβR-I(LB) did not elevate Smad2 phosphorylation and BMPR-IB(LT) did not elevate Smad1 phosphorylation (FIG. 20B). It was concluded that the subtype-specific residues in the receptor L45 loop determine the specificity of Smad recognition, phosphorylation and activation.

EXAMPLE 20
Matching Determinants of Specificity in R-Smads

The conserved C-terminal domain of R-Smad proteins, which is known as the "Mad homology-2" (MH2) domain, interacts with specific TGF-β family receptors and has specific effector functions. When expressed on its own in tissue culture cells or Xenopus embryos, the Smad2 MH2 domain is able to interact with the TGF-β receptor[50], associate with Fast1[49] and generate TGF-β and activin-like effects[16,42]. These observations suggested that the receptor and DNA binding protein interactions of R-Smads are specified by determinants in the MH2 domain.

Figure 21A:
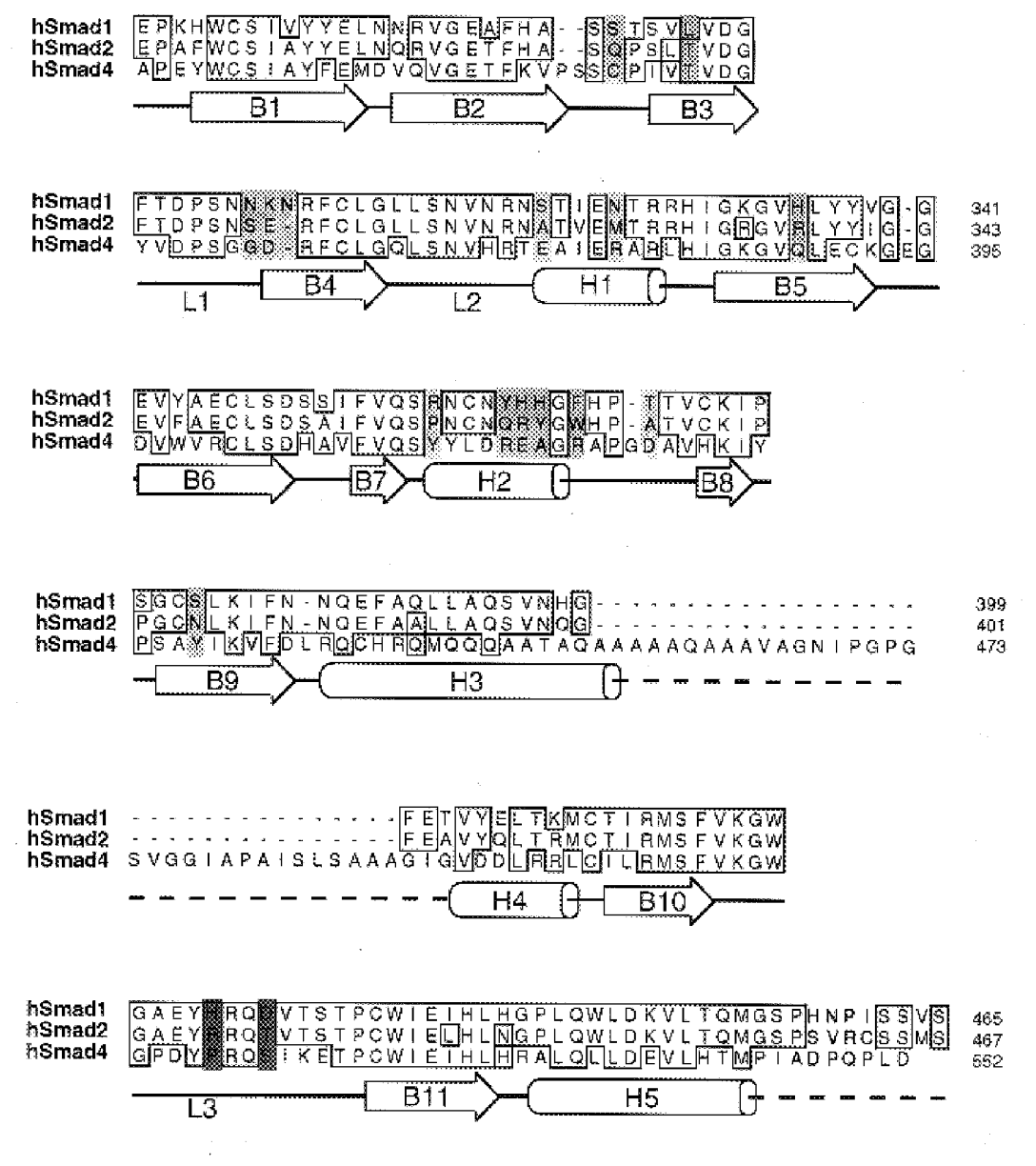
Figure 21B:
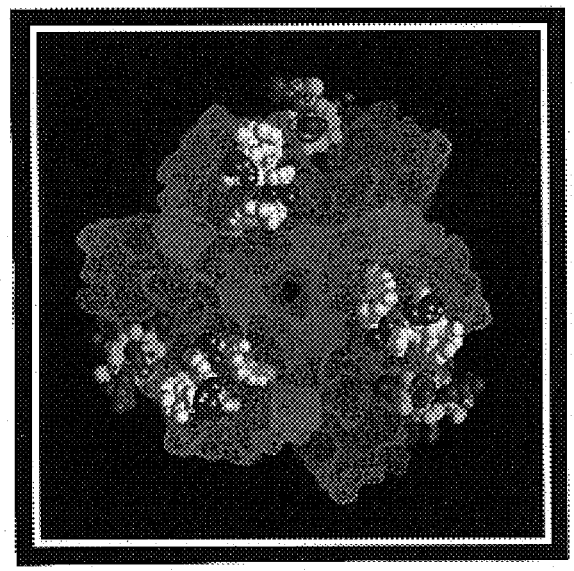
FIG. 21B shows a frontal view of the location of the L3 loop and helix 2 or each MH2 monomer in the crystallographic trimer.
Figure 21C:
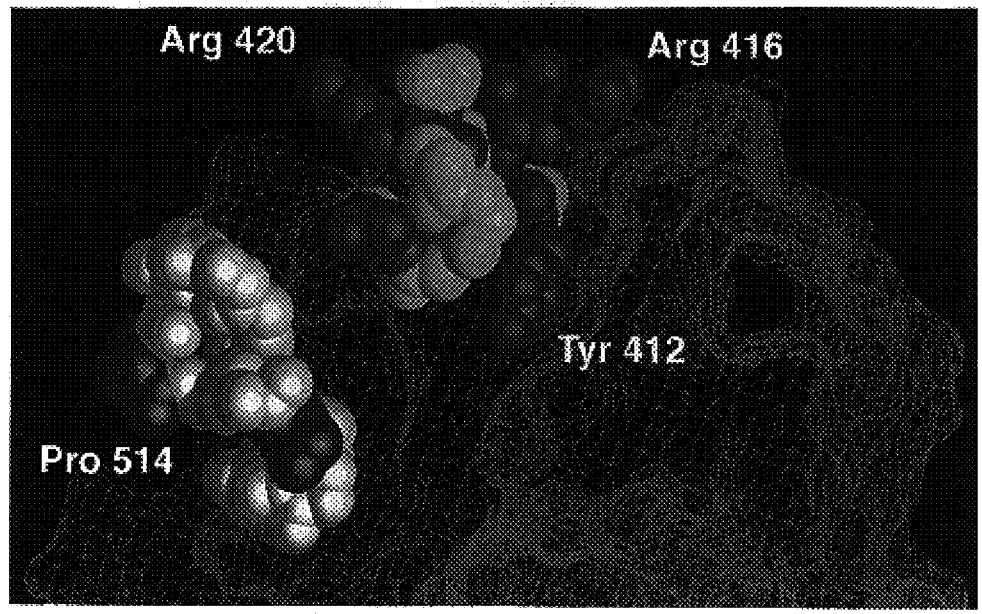
FIG. 21C shows a close-up, lateral view of the Smad4 MH2 crystal structure showing the L3 loop (yellow) with subtype specific residues (red) and the α-helix 2 (cyan) with subtype-specific residues (magenta).

To search for such determinants, 21 amino acid residues of the MH2 domain that are not conserved between Smad1 and Smad2 but are highly conserved in Smads 1, 5, 8 and Mad, or in Smads 2 and 3 were investigated (FIG. 21A). The location of these residues in the three-dimensional structure of the protein can be inferred from the crystal structure of the Smad4 MH2 domain[57]. The Smad4 MH2 monomer contains two β-sheets capped on one side by three α-helices (H3, H4 and H5) forming a bundle and, on the other side, by two large loops (L1 and L2) and an α-helix (H1). Smads form homo-oligomers in the cell[9,66] and in solution[57]. In the crystal structure, the Smad4 MH2 domain forms a disc-shaped trimer, with the loop/helix region of one monomer forming an interface with the three-helix bundle of the next monomer (FIGS. 21B–C). Mutations in tumor-derived, inactive alleles of Smad2 and Smad4 often map to this interface[57]. At the amino acid sequence level, most of the structural elements of the Smad4 MH2 domain are conserved in the R-Smads (FIG. 21A), which suggests that this three-dimensional structure is also conserved in R-Smads.

Seven of the 21 subtype-specific amino acid residues (gray in FIG. 21A) are clustered on the N-terminal side of the disc, near the point of connection to the N-terminal half of the Smad molecule; these residues are only partially exposed to solvent[57]. Two subtype-specific residues (yellow in FIG. 21A) are located in α-helix 1, and six other (purple in FIG. 21A) are at or near α-helix 2, which is highly exposed on the edge of the disc (FIGS. 21B–C). Of the remaining subtype-specific residues, two (red in FIG. 21A) are located in the L3 loop, a structure protruding from each monomer on the C-terminal side of the disc (FIG. 18B), and the last four (green in FIG. 21A) are located immediately upstream of the C-terminal receptor phosphorylation motif SS(V/M)S. Neither these four amino acids nor the phosphorylation motif itself are required for association with the TGF-β receptor[50,30].

Figure 22A:
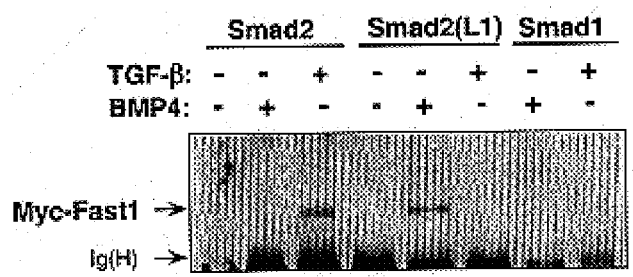
FIG. 22A shows that L3 loop determines Smad activation by a specific receptor but not Smad interaction with Fast1. COS1 cells were transfected with Flag-tagged Smad constructs, myc-tagged Fast1, and TGF-β receptors or BMP receptors. Cells were incubated with the corresponding receptor ligands, TGF-β1 or BMP4, and Smad association with Fast1 was determined. Ig(H), immunoglobulin heavy chain.
Figure 22B:
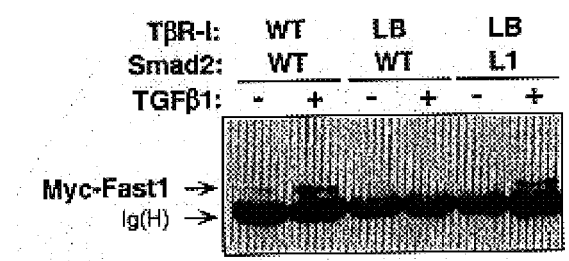
FIGS. 22B and C show that TβR-I(LB) rescues the ability of TGF-β to induce Smad2(L1) association with Fast1 (B) and activation of the A3-luciferase Mix.2 reporter (C). R1B/L17 cells transfected with various constructs, as indicated, were incubated with 0.5 nM TGF-β for 20 h, and luciferase activity was measured.
Figure 22C:
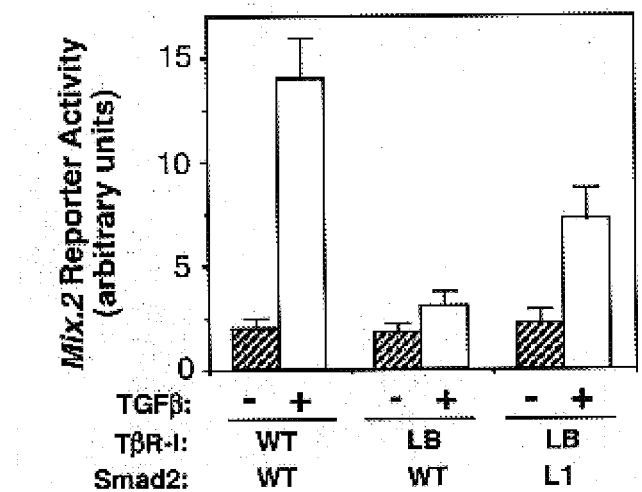
FIG. 22 shows the matching receptor L45 loops and R-Smad L3 loops.

Mutational analysis has shown that the L3 loop of Smad4 is essential for interaction with R-Smads[57] whereas the L3 loop of R-Smads is essential for interaction with TGF-β receptors[50]. Furthermore, the two subtype-specific amino acids in this loop determine the specificity of the Smad-receptor interactions[50]. To determine if the specificity of a R-Smad L3 loop matches the specificity of the receptor L45 loop, it was investigated whether a Smad2 construct containing the Smad1 L3 loop sequence [Smad2(L1) construct] and the mutant TβR-I(LB) receptor construct would complement each other in the rescue of a TGF-β response. The association of Smad2 with Fast1 in response to agonist was used as a readout in these experiments. Formation of this complex recapitulates various additional signaling events (see FIG. 18B). The Smad2(L1) construct bound Fast1 in response to BMP but not in response to TGF-β (FIG. 22A), which is consistent with the ability of Smad2(L1) to recognize BMPR-IB but not TβR-I[50]. TβR-I(LB) failed to mediate Smad2 association with Fast1. However, TβR-I(LB) mediated Smad2(L1) association with FastI (FIG. 22B). Furthermore, the combination of TβR-I(LB) and Smad2(L1) rescued, partially at least, the ability to activate a Mix.2 reporter construct in response to TGF-β (FIG. 22C). Therefore, the specificity of TGF-β receptor-Smad interaction is determined by the L45 loop of the type I receptor and a complementary L3 loop in Smad2.

EXAMPLE 21
Determinants of Smad Interaction with a DNA-binding Partner

How a specific gene is targeted for activation by Smads has been delineated in the case of Mix.2. Activation of Mix.2 by activin or TGF-β requires. the formation of a Smad2-Smad4-Fast1 complex which binds to a specific promoter sequence known as the "activin response element" (ARE)[36,34,49]. In this complex, the DNA binding domain of Fast1 mediates specific binding to the ARE[36] whereas the Smads act as transcriptional activators and enhancers of DNA binding[49]. The interaction between Smad2 and Fast1 is direct, as determined by their ability to interact as recombinant proteins in solution or in a yeast two-hybrid assays[34].

Figure 23A:
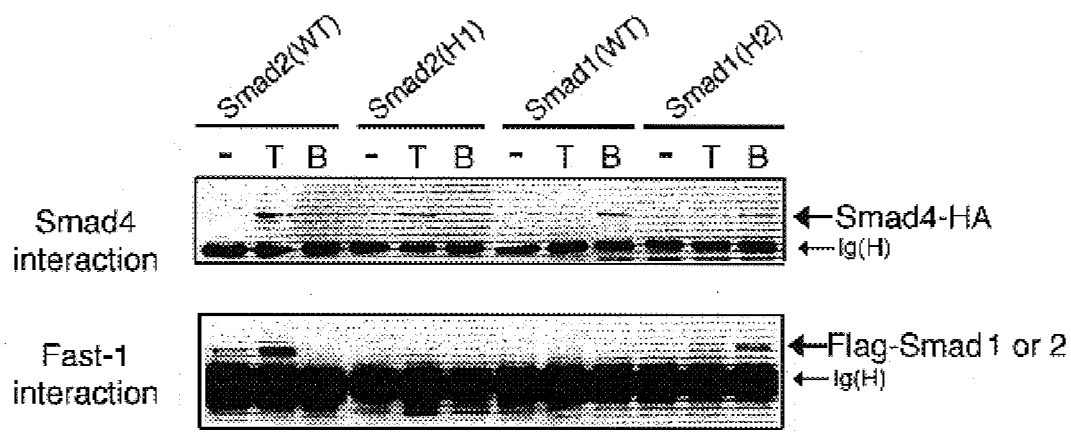
FIG. 23A shows the interaction of wild type R-Smads and helix 2 exchange mutants with Smad4 and Fast1. HA-tagged Smad4 or myc-tagged Fast1 constructs were cotransfected into COS1 cells with the indicated Flag-tagged forms of Smad1 or Smad2. Transfectants were incubated with TGF-β (T) or BMP2 (B) and the associations of R-Smads with Smad4 (upper panel) and with Fast1 (lower panel) were determined. The helix 2 exchange mutants bound Smad4 in response to their agonists, but Smad2(H1) lost the ability to associate with Fast1 whereas Smad2(H1) gained the ability to bind Fast1 in response to BMP.
Figure 23B:
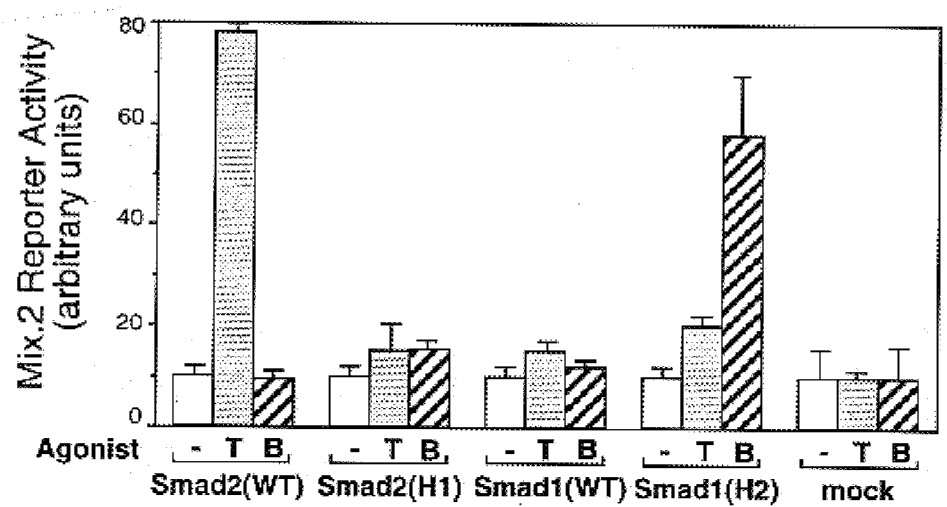
FIG. 23B shows the activation of a Mix.2 reporter by wild type R-Smads and helix 2 exchange mutants. L17 cells were cotransfected with the indicated forms of Smad1 or Smad2, Fast1, the A3-luciferase construct, and TGF-β receptors or BMP receptors. Cells were incubated with the corresponding receptor ligands, and luciferase activity was determined. Smad2(H1) lost the ability to activate the reporter whereas Smad1(H2) gained the ability to do so in response to BMP.
Figure 23C:
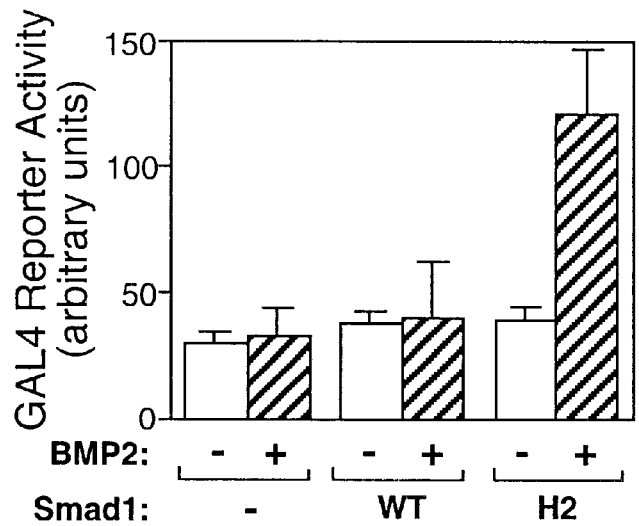
FIG. 23C shows Fast1-dependent activation of a GAL4 reporter by Smad1 (H2). L17 cells were cotransfected with the indicated forms of Smad1, a Fast1 fusion with the DNA binding domain from yeast GAL4, a GAL luciferase reporter, and BMP receptors. Cells were incubated with or without BMP2, and luciferase activity was determined.
Figure 23D:
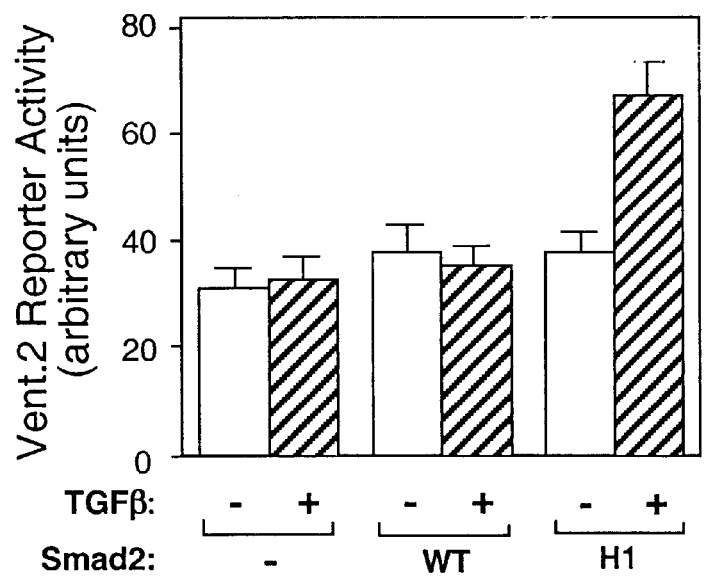
FIG. 23D shows the activation of the Xvent.2-luciferase reporter in P19 cells cotransfected with TβR-I, TβR-II and the indicated Smad2 constructs. Cells were incubated with or without TGF-β, and luciferase activity was determined in triplicate samples.

To identify a structural element that might specify the interaction of Smad2 with Fast1, it was investigated whether candidate Smad2 sequences introduced into Smad1 would allow it to recognize Fast1 and activate a Mix.2 ARE reporter in response to BMP. The presence of six subtype-specific residues in the helix 2 of the MH2 domain (FIG. 21A), and the prominent exposure of helix 2 on the edge of the MH2 trimer (FIGS. 21B–C) made this region a good candidate for this interaction. Exchanging the six subtype-specific helix 2 residues of Smad1 and Smad2 did not alter the specificity of their receptor interactions. Smad1 containing the helix 2 sequence of Smad2 [Smad1(H2) construct] bound Smad4 in response to BMP, and the reciprocal construct, Smad2(H1), bound Smad4 in response to TGF-β (FIG. 23A, upper panel). However, these helix 2 mutations switched the pattern of interactions with Fast1. Smad1(H2) gained the ability to associate with Fast1 in response to BMP whereas Smad2(H1) failed to do so in response to TGF-β (FIG. 23A, lower panel). Correlating with this switch, Smad1(H2) was able to mediate activation of a Mix.2 reporter in response to BMP whereas Smad2(H1) was unable to mediate activation of this reporter (FIG. 23B). The Fast1 interaction specified by the Smad2 helix 2 was independent of the target promoter since Smad1(H2) was also able to activate a GAL4 reporter construct in cooperation with a Fast1-GAL4 DNA binding domain fusion (FIG. 23C). These results suggest that α-helix 2 of Smad2 is primarily responsible for the specificity for Fast1 and, as a result, the gene responses activated by the pathway. Extending these observations to the BMP pathway, Smad2(H1) gained the ability to mediate activation of a Vent.2 reporter in response to TGF-β (FIG. 23D).

EXAMPLE 22
Determinants of Specificity of TGF-β Signal Transduction

Key determinants of specificity at three levels in the TGF-β and BMP signaling pathways have been identified. These determinants are encoded by specific amino acid residues in the L45 loop of the kinase domain in the type I receptors, and in the L3 loop and the α-helix 2 of the MH2 domain in R-Smads. In each case, the residues involved are few and highly conserved in receptors or R-Smads that have similar signaling specificity. The interaction between these proteins may involve additional surface contacts, but results presented herein suggest that pathway specificity is largely determined by these residues. Exchanging these residues at any of the three levels between TGF-β and BMP pathway components switches the signaling specificity of these pathways.

The L45 loop of type I receptor kinases had previously drawn attention because replacing the entire kinase domain except this loop in TβR-I with the corresponding regions from the functionally divergent receptor kinase ALK2 still allows mediation of TGF-β responses[38]. The L3 loop of Smads has drawn attention as a target of inactivating mutations in Drosophila and Caenorhabditis elegans Smad family members[18,19]. As inferred from the effect of similar mutations in vertebrate Smads, the L3 loop participates in different interactions that are essential for signaling. In Smad4 the L3 loop is required for interaction with activated R-Smads[57], whereas in R-Smads the L3 loop is required for interaction with the receptors and, furthermore, it specifies these interactions[50]. The present results show that matching combinations of L45 loops and L3 loops determine the specificity of the receptor-Smad interaction. Exchanging the subtype-specific residues in either the L45 loop or the L3 loop causes a switch in the specificity of this interaction, with an attendant switch in the signaling specificity of the pathway. As evidence of a functional match between a receptor L45 loop and a R-Smad L3 loop, the switch in the signaling specificity of a TGF-β receptor construct containing the BMP receptor L45 loop can be reversed by a Smad2 construct containing the matching L3 loop sequence from Smad1.

Results presented herein suggest that the interaction supported by the L45 and L3 loops achieves signal transduction by selectively increasing the affinity of a particular receptor kinase for a particular subtype of R-Smads. The docking interaction between receptors and R-Smads is independent of their catalytic interaction. The C-terminal SSXS phosphorylation motif of R-Smads and the adjacent upstream sequence are neither required for association with the receptors in vivo nor for the specificity of this interaction[50]. However, effective R-Smad phosphorylation in vivo requires this docking interaction. Mutations that disrupt receptor docking strongly inhibit Smad phosphorylation and signal transduction. Of note, no stable interaction has been observed between the recombinant receptor kinase domains and Smads 1 or 2 in solution. Under these conditions, the TβR-I and BMPR-IB kinases can phosphorylate both Smad1 and Smad2, and mutations in the L45 loop do not inhibit these reactions. The interaction supported by the L45 and L3 loops therefore might be cooperative, requiring the correct assembly of multivalent receptor complexes and R-Smad complexes in the cell.

The present work also provides evidence that the choice of DNA binding partner and, consequently, the choice of target genes are determined by helix 2 in the MH2 domain of R-Smads. In the crystal structure of the Smad4 MH2 domain, helix 2 protrudes from the edge of the Smad trimer with several highly exposed residues. The sequence of helix 2 is divergent between R-Smads that mediate TGF-β (or activin) responses and those that mediate BMP responses, but is highly conserved within each subgroup of R-Smads. Using as models the Mix.2 gene response to TGF-β and the Vent.2 gene response to BMP, it was shown herein that the helix 2 of Smad2 and Smad1, respectively, determine the ability to mediate these responses. It was further shown that helix 2 from Smad2 specifies the selective interaction of Smads with the ARE-binding factor Fast1. Factors that mediates other Smad2- or Smad1-dependent gene responses remain to be identied. The ability of helix 2 to determine these interactions may provide ways to identify such factors. The role of helix 2 in Smad4 is also not known, although a mutation (R420H) in this region has been reported in lung carcinoma[4].

Figure 24:
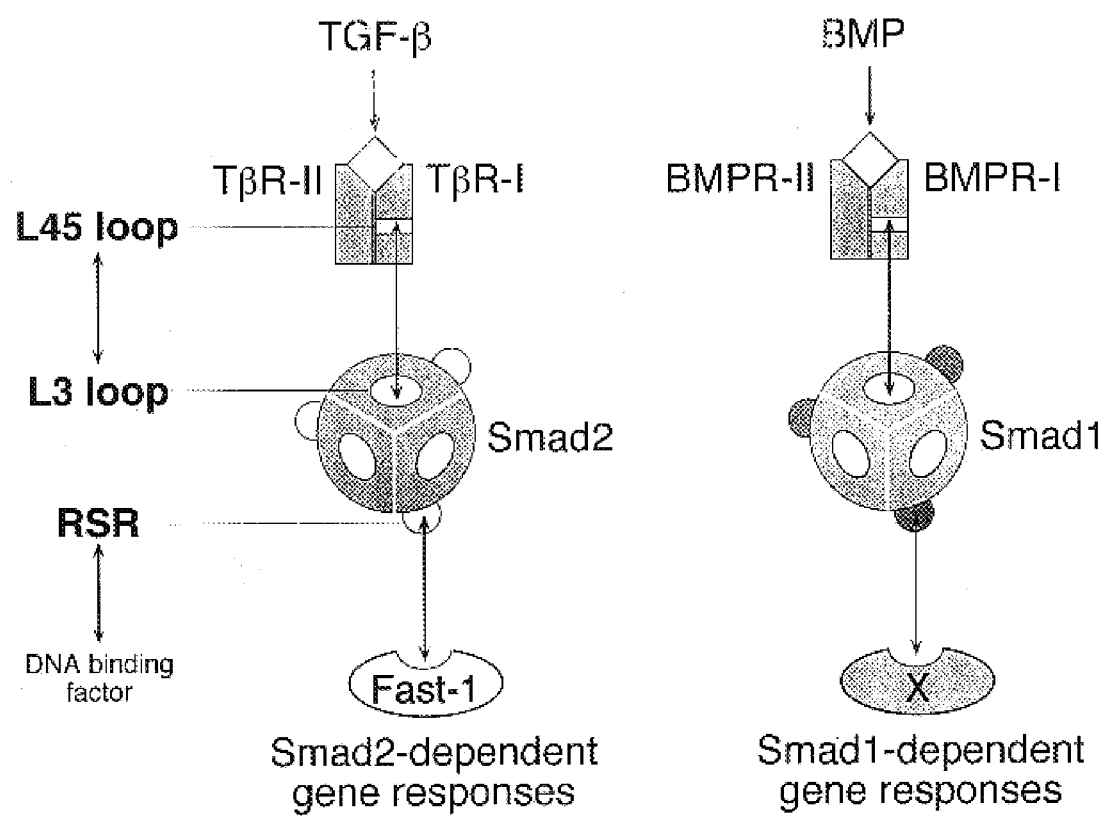
FIG. 24 shows the determinants of specificity in TGF-β signal transduction. In the TGF-β or BMP receptor complexes, the type I receptor recognizes and phosphorylates a specific R-Smad, such as Smad2 in the TGF-β pathway or Smad1 in the BMP pathway[43,52]. The R-Smad then associates with Smad4 and moves into the nucleus. Specific association with the DNA-binding factor Fast1 in the nucleus takes the Smad2-Smad4 complex to specific target genes such as Mix.2, activating their transcription[36,34,49]. Selection of a R-Smad by a receptor is specified by the type I receptor L45 loop and the R-Smad L3 loop, whereas selection of a DNA-binding factor (such as Fast1 in the case of Smad2) is specified by the α-helix 2 of the R-Smad. Exchanging any of these three elements between the TGF-β and BMP receptors or between Smad1 and Smad2 causes a switch in the signaling specificity of these two pathways. Specific activation of other target genes by Smad1 or Smad2 complexes is presumed to involve different DNA-binding partners.

The identification of determinants of specificity at three levels in TGF-β signal transduction suggests a general model for the organization of the selective protein-protein interactions that configure this signaling network (FIG. 24). The determinants of specificity identified herein segregate the TGF-β and BMP pathways from each other. Still, each pathway can generate different responses in different cell types. Specificity at that level may depend on the repertoire of gene-targeting factors that the Smad complex encounters in the nucleus of a given cell.

The following references were cited herein:

1. Hahn, S. A., et al. *Science* 271, 350–353 (1996).
2. Schutte, M., et al. *Cancer Research* 56, 2527–2530 (1996).
3. Kim, S. K., et al. *Cancer Research* 56, 2519–2521 (1996).
4. Nagatake, M., et al. *Cancer Research* 56, 2718–2720 (1996).
5. Massague, *J. Cell* 85, 947–950 (1996).
6. Derynck, R., et al. *Cell* 87, 173 (1996).
7. Derynck, R. & Zhang, Y. *Current Biology* 6, 1226–1229 (1996).
8. Zhang, Y., et al. *Nature* 383, 168–172 (1996).
9. Lagna, G., et al. *Nature* 383, 832–836 (1996).
10. Yingling, J. M., et al. *Proc. Natl. Acad. Sci. USA* 93, 8940–8944 (1996).
11. Hoodless, P. A., et al. *Cell* 85, 489–500 (1996).
12. Eppert, K., et al. *Cell* 86, 543–552 (1996).
13. Lechleider, R. J., et al. *J. Biol. Chem.* 271, 17617–17620 (1996).
14. Liu, F., et al. *Nature* 381, 620–623 (1996).
15. Candia, A. F., et al. 1997. *Development* 124: 4467–4480.
16. Baker, J. C. & Harland, R. M. *Genes & Development* 10, 1880–1889 (1996).
17. Thiagalingam, S., et al. *Nature Genetics* 13, 343–346 (1996).
18. Sekelsky, J. J., et al. *Genetics* 139, 1347–1358 (1995).
19. Savage, C., et al. *Proc. Natl. Acad. Sci. USA* 93, 790–794 (1996).
20. Stura, E. A. & Wilson, I. A. in *Crystallization of Nucleic Acids and Proteins* (eds. Ducruix, A. & Giege, R.) 99–126 (Oxford University Press, Oxford, 1992).
21. Sheldrick, G. in *Patterson interpretation and the use of macromolecular delta-F data* (Daresbury, 1991).
22. Collaborative Computational Project, N. The CCP4 suite: programs for protein crystallography. *Acta Crystallogr.* D50, 760–763 (1994).
23. Zhang, K. Y. J. *Acta Crystallogr.* D49, 213–222 (1993).
24. Jones, T. A., et al. *Acta Crystallogr.* A47, 110–119 (1991).
25. Brunger, A. T. X-PLOR, *a System for Crystallography and NMR* (Yale University Press, New Haven, Conn., 1991).

26. Klaulis, P. J. *J. Appl. Crystallogr.* 24, 946–950 (1991).
27. Merrit, E. A. & Murphy, M. E. *Acta Crystallogr.* D50, 869–873 (1994).
28. Uchida, K., et al. *Cancer Research* 56, 5583–5585 (1996).
29. Nicholls, A., et al. *Proteins: Struct. Funct. Genet.* 11, 281–296 (1991).
30. Macias-Silva, M., et al. *Cell* 87, 1215–1224 (1996).
31. Cárcamo, J., et al. 1994. *Mol. Cell Biol.* 14: 3810–3821.
32. Cárcamo, J., et al. 1995. *Mol. Cell. Biol.* 15: 1573–1581.
33. Chen, X., et al. 1996. *Nature* 383: 691–696.
34. Chen, X., et al. 1997a. *Nature* 389: 85–89.
35. Chen, Y., et al. 1997b. *Proc. Natl. Acad. Sci. U.S.A.* 94: 12938–12943.
36. Chen, Y., et al. 1996. *J. Biol. Chem.* 271: 31602–31606.
37. Chen, Y.G., et al. 1997. *EMBO J.* 16: 3866–3876.
38. Feng, X. H. and Derynck, R. 1997. *EMBO J.* 16: 3912–3922.
39. Gaddy-Kurten, D., et al. 1995. *Recent Prog. Horm. Res.* 50: 109–129.
40. Graff, J. M., et al. 1996. *Cell* 85: 479–487.
41. Hata, A., et al. 1998. *Genes Dev.* 12: 186–197.
42. Hata, A., et al. 1997. *Nature* 388: 82–86.
43. Heldin, C.-H., et al. 1997. *Nature* 390: 465–471.
44. Hogan, B. L. M. 1996. *Genes Dev.* 10: 1580–1594.
45. Huang, H-C., et al. 1995. *EMBO J.* 14: 5965–5973.
46. Kingsley, D. M. 1994. *Genes Dev.* 10: 16–21.
47. Kretzschmar, M., et al. 1997a. *Nature* 389: 618–622.
48. Kretzschmar, M., et al. 1997b. *Genes Dev.* 11: 984–995.
49. Liu, F., et al. 1997. *Genes Dev.* 11: 3157–3167.
50. Lo, R. S., et al. 1998. *EMBO J.* 17: 996–1005.
51. Massagué, J. 1990. *Ann. Rev. Cell. Biol.* 6: 597–641.
52. Massagué, J. 1998. *Annu. Rev. Biochem.* 67: 753–791.
53. Mehler, M. F., et al. 1997. *Trends Neurosci.* 20: 309–317.
54. Nakao, A., et al. 1997. *EMBO J.* 16: 5353–5362.
55. Pawson, T. and Scott, J. D. 1997. *Science* 278: 2075–2080.
56. Roberts, A. B. and Sporn, M. B. "The transforming growth factor-betas." In *Peptide growth factors and their receptors,* ed. M. B. Sporn and A. B. Roberts. 419–472. Heidelberg: Springer-Verlag, 1990.
57. Shi, Y., et al. 1997. *Nature* 388: 87–93.
58. Suzuki, A., et al. 1997. *Dev. Biol.* 184: 402–405.
59. Taylor, S. S., et al. 1992. *Annu. Rev. Cell Biol.* 8: 429–462.
60. ten Dijke, P., et al. 1994. *Science* 264: 101–104.
61. Thomsen, G. 1996. *Development* 122: 2359–2366.
62. Weis-Garcia, F. and Massagué, J. 1996. *EMBO J.* 15: 276–289.
63. Wieser, R., et al. 1995. *EMBO J.* 14: 2199–2208.
64. Wrana, J. L., et al. 1992. *Cell* 71: 1003–1014.
65. Wrana, J. L., et al. 1994. *Nature* 370: 341–347.
66. Wu, R.-Y., et al. 1997. *Mol. Cell. Biol.* 17: 2521–2528.
67. Cheifetz, S., et al. 1990. *J. Biol. Chem.* 265: 20533–20538.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those. skilled in the art which are encompassed within the spirit of the invention as defined by the scope of the claims.

What is claimed is:

1. A method of testing compounds for enhancing or inhibiting binding of Smad2 polypeptide to FAST1 DNA binding polypeptide, comprising the steps of:
   a) providing (i) a Smad2 polypeptide comprising the α-helix 2 of the MH2 domain, the TGF-β receptor docking domain and the carboxy terminal phosphorylation domain, (ii) FAST1 DNA binding polypeptide, and (iii) a compound to be tested;
   b) phosphorylating said Smad2 polypeptide with an activated receptor selected from the group consisting of TGF-β and activin type I receptors;
   c) contacting said phosphorylated Smad2 polypeptide with said FAST1 DNA binding polypeptide in the presence or absence of said compound under conditions where binding of said Smad2 polypeptide to said FAST1 DNA binding polypeptide can take place; and
   d) detecting binding of said Smad2 polypeptide to said FAST1 DNA binding polypeptide, wherein increased or decreased binding in the presence of said compound indicates said compound enhances or inhibits, respectively, the binding of said Smad2 polypeptide to said FAST1 DNA binding polypeptide.

* * * * *

UNITED STATES PATENT AND TRADEMARK OFFICE
CERTIFICATE OF CORRECTION

PATENT NO.   : 6,824,971 B1
DATED        : November 30, 2004
INVENTOR(S)  : Nikola Pavletich, Yigong Shi and Joan Massague It is certified that error appears in the above-identified patent and that said Letters Patent is hereby corrected as shown below:

Column 1,
Line 23, please delete the word "a".

Column 2,
Line 6, please delete the word "a".

Column 3,
Line 56, please delete the comma after "steps".
Line 57, please insert -- and -- after "substance;".

Column 4,
Line 10, please delete the comma after "steps".
Line 29, please delete the comma after "steps".

Column 5,
Line 10, please delete the period after "of".
Line 27, "shows" should read -- show --.
Line 45, please insert -- and -- after "residues".
Line 63, "a" should read -- an --.

Column 10,
Line 48, please delete the space between "an" and "d".

Column 15,
Line 16, please delete "a".

Column 24,
Line 1, please delete the period after "that".

Column 28,
Line 54, "This" should read -- These --.
Line 67, "Kinase" should not be capitalized.

Column 33,
Line 55, please delete the period after "distinct".

Column 34,
Line 54, "orthorphosphate" should read -- orthophosphate --.

Column 38,
Line 26, please delete the period after "requires".
Line 35, please delete "a".

UNITED STATES PATENT AND TRADEMARK OFFICE
CERTIFICATE OF CORRECTION

PATENT NO. : 6,824,971 B1
DATED : November 30, 2004
INVENTOR(S) : Nikola Pavletich, Yigong Shi and Joan Massague It is certified that error appears in the above-identified patent and that said Letters Patent is hereby corrected as shown below:

<u>Column 40,</u>
Line 11, "mediates" should read -- mediate --.

Signed and Sealed this

Twenty-second Day of March, 2005

JON W. DUDAS
*Director of the United States Patent and Trademark Office*